(12) United States Patent
Maranga et al.

(10) Patent No.: US 12,060,567 B2
(45) Date of Patent: Aug. 13, 2024

(54) ENGINEERED UNTRANSLATED REGIONS (UTR) FOR AAV PRODUCTION

(71) Applicant: VOYAGER THERAPEUTICS, INC., Cambridge, MA (US)

(72) Inventors: Luis Maranga, Acton, MA (US); Sylvain Cecchini, Westborough, MA (US); David Dismuke, Cary, NC (US)

(73) Assignee: Voyager Therapeutics, Inc., Lexington, MA (US)

( * ) Notice: Subject to any disclaimer, the term of this patent is extended or adjusted under 35 U.S.C. 154(b) by 901 days.

(21) Appl. No.: 17/251,482

(22) PCT Filed: Jun. 13, 2019

(86) PCT No.: PCT/US2019/036922
§ 371 (c)(1),
(2) Date: Dec. 11, 2020

(87) PCT Pub. No.: WO2019/241486
PCT Pub. Date: Dec. 19, 2019

(65) Prior Publication Data
US 2021/0301305 A1 Sep. 30, 2021

Related U.S. Application Data

(60) Provisional application No. 62/684,410, filed on Jun. 13, 2018, provisional application No. 62/691,743, filed on Jun. 29, 2018, provisional application No. 62/741,746, filed on Oct. 5, 2018, provisional application No. 62/741,779, filed on Oct. 5, 2018.

(51) Int. Cl.
*C12N 15/86* (2006.01)
*C07K 14/005* (2006.01)
*C12N 7/00* (2006.01)

(52) U.S. Cl.
CPC ............ *C12N 15/86* (2013.01); *C07K 14/005* (2013.01); *C12N 7/00* (2013.01); *C12N 2750/14122* (2013.01); *C12N 2750/14143* (2013.01); *C12N 2750/14151* (2013.01); *C12N 2840/10* (2013.01)

(58) Field of Classification Search
CPC ................. C12N 15/86; C12N 7/00; C12N 2750/14122; C12N 2750/14143; C12N 2750/14151; C12N 2840/10; C07K 14/005
See application file for complete search history.

(56) References Cited

U.S. PATENT DOCUMENTS

2012/0295960 A1   11/2012   Palfi et al.

FOREIGN PATENT DOCUMENTS

AU   2013254897 B2 *   1/2016   .......... C07K 14/005
WO   2007046703 A2      4/2007
WO   2017181162 A1     10/2017

OTHER PUBLICATIONS

J.R. Babendure et al: "Control of mammalian translation by mRNA structure near caps", RNA, vol. 12, No. 5, Jan. 1, 2006 (Jan. 1, 2006), pp. 851-861.
Tamas Virag et al: "Producing Recombinant Adeno-Associated Virus in Foster Cells: Overcoming Production Limitations Using a Baculovirus-Insect Cell Expression Strategy", Human Gene Therapy, vol. 20, No. 8, Aug. 1, 2009 (Aug. 1, 2009), pp. 807-817.
M. Kozak: "Circumstances and mechanisms of inhibition of translation by secondary structure in eucaryotic mRNAs.", Molecular and Cellular Biology, vol. 9, No. 11, Nov. 1, 1989 (Nov. 1, 1989), pp. 5134-5142.
International Search Report received in corresponding PCT application No. PCT/US2019/036922 dated Oct. 14, 2019.

* cited by examiner

*Primary Examiner* — Brian Whiteman
*Assistant Examiner* — Stephanie L Sullivan
(74) *Attorney, Agent, or Firm* — Nelson Mullins Riley & Scarborough LLP; Jane E. Remillard, Esq.; Christopher L. Frank

(57) ABSTRACT

The present disclosure describes methods and systems for use in the production of recombinant adeno-associated virus (rAAV) particles. In certain embodiments, the production process and system include engineered untranslated regions (UTR) which allow for the controlled expression of AAV capsid proteins, such as VP1, VP2 and VP3. In certain embodiments, the production process and system include engineered untranslated regions (UTR) which allow for the controlled expression of non-structural AAV replication proteins, such as Rep78 and Rep52.

20 Claims, 13 Drawing Sheets

Specification includes a Sequence Listing.

SEQUENCE LISTING

```
<160> NUMBER OF SEQ ID NOS: 72

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atacgactcg acgaagactt gatcaaccgt cggctttatg gct          43

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atacgactcg acgaagactt gatcaaccat cggctttatg gct          43

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atacgactcg acgaagactt gatcaaccgt aggctttatg gct          43

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atacgactcg acgaagactt gatcctgact cggctttatg gct          43

<210> SEQ ID NO 5
<211> LENGTH: 43
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 5
atacgactcg acgaagactt agttaaccgt cggctttatg gct                        43

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atacgactcg acgaagactt agttaaccgt ccgctttatg gct                        43

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atacgactcg acgaagactt agttaactgt ccgctttatg gct                        43

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atacgactcg acgaagacct gccatctaag gcagtttatg gct                        43

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atacgactct gccagctcat ctaagagctg gcagtttatg gct                        43

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atacgactct gcctgctcat ctaagagctg gcagtttatg gct                        43

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atacctgcca gctcttcgat ctaacgaaga gctggcagtt tatggct         47

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atacctgcct gctcttcgat ctaacgaaga gctggcagtt tatggct         47

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atacctgcct gctcatcgat ctaacgaaga gctggcagtt tatggct         47

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atacctgcca tctaaggcag gactcgacga agactttatg gct             43

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atacctgcca gctcatctaa gagctggcag gactttatg gct              43

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atacctgcct gctcatctaa gagctggcag gactttatg gct              43

<210> SEQ ID NO 17
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 17
atacgactcg acgaagactt gatc                                              24

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atacgactcg acgaagactt gatcctgact                                        30

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atacgactcg acgaagactt                                                   20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atacgactcg acgaagac                                                     18

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaccgtcggc                                                              10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aaccatcggc                                                              10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 23
aaccgtaggc                                                          10

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agttaaccgt cggc                                                     14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agttaaccgt ccgc                                                     14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agttaactgt ccgc                                                     14

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ctgccagctc                                                          10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctgcctgctc                                                          10

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 29
ctgccagctc ttcg                                                      14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctgcctgctc ttcg                                                      14

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctgcctgctc atcg                                                      14

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gagctggcag                                                           10

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgaagagctg gcag                                                      14

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gactcgacga agactttatg gct                                            23

<210> SEQ ID NO 35
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 35 gactttatg gct                                                                              13

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atacgactcg acgaagactt gatcaaccgt cggcttt                                                   37

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atacgactcg acgaagactt gatcaaccat cggcttt                                                   37

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atacgactcg acgaagactt gatcaaccgt aggcttt                                                   37

<210> SEQ ID NO 39
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atacgactcg acgaagactt gatcctgact cggcttt                                                   37

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atacgactcg acgaagactt agttaaccgt cggcttt                                                   37

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
atacgactcg acgaagactt agttaaccgt ccgcttt                              37
```

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
atacgactcg acgaagactt agttaactgt ccgcttt                              37
```

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
atacgactcg acgaagacct gccatctaag gcagttt                              37
```

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
atacgactct gccagctcat ctaagagctg gcagttt                              37
```

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
atacgactct gcctgctcat ctaagagctg gcagttt                              37
```

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
atacctgcca gctcttcgat ctaacgaaga gctggcagtt t                         41
```

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
atacctgcct gctcttcgat ctaacgaaga gctggcagtt t              41
```

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

```
atacctgcct gctcatcgat ctaacgaaga gctggcagtt t              41
```

<210> SEQ ID NO 49
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
atacctgcca tctaaggcag gactcgacga agacttt                   37
```

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
atacctgcca gctcatctaa gagctggcag gactttt                   37
```

<210> SEQ ID NO 51
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

```
atacctgcct gctcatctaa gagctggcag gactttt                   37
```

<210> SEQ ID NO 52
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
gacctttaat tcaacccaac acaatatatt atagttaaat aagaattatt atcaaatcat   60
ttgtatatta attaaaatac tatactgtaa attacatttt atttacaatc             110
```

<210> SEQ ID NO 53
<211> LENGTH: 2208
<212> TYPE: DNA
<213> ORGANISM: Adeno-associated virus 2

<400> SEQUENCE: 53

```
atggctgccg acggttatct acccgattgg ctcgaggaca ctctctctga aggaataaga   60
```

| | | |
|---|---|---|
| cagtggtgga agctcaaacc tggcccacca ccaccaaagc ccgcagagcg gcataaggac | 120 | |
| gacagcaggg gtcttgtgct tcctgggtac aagtacctcg gacccttcaa cggactcgac | 180 | |
| aagggagagc cggtcaacga ggcagacgcc gcggccctcg agcacgacaa agcctacgac | 240 | |
| cggcagctcg acagcggaga caacccgtac ctcaagtaca accacgccga cgcggagttt | 300 | |
| caggagcgcc ttaaagaaga tacctctttt gggggcaacc tcggacgagc agtcttccag | 360 | |
| gcgaaaaaga gggttcttga acctctgggc ctggttgagg aacctgttaa gacggctccg | 420 | |
| ggaaaaaaga ggccggtaga gcactctcct gtggagccag actcctcctc gggaaccgga | 480 | |
| aaggcgggcc agcagcctgc aagaaaaaga ttgaattttg gtcagactgg agacgcagac | 540 | |
| tcagtacctg accccagcc tctcggacag ccaccagcag cccctctgg tctgggaact | 600 | |
| aatacgatgg ctacaggcag tggcgcacca atggcagaca taacgagggg cgccgacgga | 660 | |
| gtgggtaatt cctcgggaaa ttggcattgc gattccacat ggatgggcga cagagtcatc | 720 | |
| accaccagca cccgaacctg ggccctgccc acctacaaca accacctcta caaacaaatt | 780 | |
| tccagccaat caggagcctc gaacgacaat cactactttg gctacagcac cccttggggg | 840 | |
| tattttgact tcaacagatt ccactgccac ttttcaccac gtgactggca agactcatc | 900 | |
| aacaacaact ggggattccg acccaagaga ctcaacttca gctctttaa cattcaagtc | 960 | |
| aaagaggtca cgcagaatga cggtacgacg acgattgcca ataaccttac cagcacggtt | 1020 | |
| caggtgtttta ctgactcgga gtaccagctc ccgtacgtcc tcggctcggc gcatcaagga | 1080 | |
| tgcctcccgc cgttccagc agacgtcttc atggtgccac agtatggata cctcacctg | 1140 | |
| aacaacggga gtcaggcagt aggacgctct tcattttact gcctggagta ctttcctct | 1200 | |
| cagatgctgc gtaccggaaa caactttacc ttcagctaca cttttgagga cgttcctttc | 1260 | |
| cacagcagct acgctcacag ccagagtctg gaccgtctca tgaatcctct catcgaccag | 1320 | |
| tacctgtatt acttgagcag aacaaacact ccaagtggaa ccaccacgca gtcaaggctt | 1380 | |
| cagttttctc aggccggagc gagtgacatt cgggaccagt ctaggaactg gcttcctgga | 1440 | |
| ccctgttacc gccagcagcg agtatcaaag acatctgcgg ataacaacaa cagtgaatac | 1500 | |
| tcgtggactg gagctaccaa gtaccacctc aatggcagag actctctggt gaatccgggc | 1560 | |
| ccggccatgg caagccacaa ggacgatgaa gaaaagtttt tccctcagag cggggttctc | 1620 | |
| atctttggga agcaaggctc agagaaaaca aatgtggaca ttgaaaaggt catgattaca | 1680 | |
| gacgaagagg aaatcaggac aaccaatccc gtggctacgg agcagtatgg ttctgtatct | 1740 | |
| accaacctcc agagaggcaa cagacaagca gctaccgcag atgtcaacac acaaggcgtt | 1800 | |
| cttccaggca tggtctggca ggacagagat gtgtaccttc aggggcccat ctgggcaaag | 1860 | |
| attccacaca cggacggaca ttttcacccc tctcccctca tgggtggatt cggacttaaa | 1920 | |
| caccctcctc cacagattct catcaagaac accccggtac ctgcgaatcc ttcgaccacc | 1980 | |
| ttcagtgcgg caaagtttgc ttccttcatc acacagtact ccacgggaca ggtcagcgtg | 2040 | |
| gagatcgagt gggagctgca gaaggaaaac agcaaacgct ggaatcccga aattcagtac | 2100 | |
| acttccaact acaacaagtc tgttaatgtg gactttactg tggacactaa tggcgtgtat | 2160 | |
| tcagagcctc gcccccattgg caccagatac ctgactcgta atctgtaa | 2208 | |

<210> SEQ ID NO 54
<211> LENGTH: 2355
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
ttacagatta cgagtcaggt atctggtgcc aatggggcga ggctctgaat acacgccatt      60
agtgtccaca gtaaagtcca cattaacaga cttgttgtag ttggaagtgt actgaatttc     120
gggattccag cgtttgctgt tttccttctg cagctcccac tcgatctcca cgctgacctg     180
tcccgtggag tactgtgtga tgaaggaagc aaactttgcc gcactgaagg tggtcgaagg     240
attcgcaggt accggggtgt tcttgatgag aatctgtgga ggagggtgtt taagtccgaa     300
tccacccatg aggggagagg ggtgaaaatg tccgtccgtg tgtggaatct ttgcccagat     360
gggcccctga aggtacacat ctctgtcctg ccagaccatg cctggaagaa cgccttgtgt     420
gttgacatct gcggtagctg cttgtctgtt gcctctctgg aggttggtag atacagaacc     480
atactgctcc gtagccacgg gattggttgt cctgatttcc tcttcgtctg taatcatgac     540
cttttcaatg tccacatttg ttttctctga gccttgcttc ccaaagatga gaacccgct     600 ctgaggaaaa aacttttctt catcgtcctt gtggcttgcc atggccgggc ccggattcac     660
cagagagtct ctgccattga ggtggtactt ggtagctcca gtccacgagt attcactgtt     720
gttgttatcc gcagatgtct ttgatactcg ctgctggcgg taacagggtc caggaagcca     780
gttcctagac tggtcccgaa tgtcactcgc tccggcctga gaaaactgaa gccttgactg     840
cgtggtggtt ccacttggag tgtttgttct gctcaagtaa tacaggtact ggtcgatgag     900
aggattcatg agacggtcca gactctggct gtgagcgtag ctgctgtgga aggaacgtc     960 ctcaaaagtg tagctgaagg taaagttgtt tccggtacgc agcatctgag aaggaaagta    1020
ctccaggcag taaaatgaag agcgtcctac tgcctgactc ccgttgttca gggtgaggta    1080
tccatactgt ggcaccatga agacgtctgc tgggaacggc gggaggcatc cttgatgcgc    1140
cgagccgagg acgtacggga gctggtactc cgagtcagta aacacctgaa ccgtgctggt    1200
aaggttattg gcaatcgtcg tcgtaccgtc attctgcgtg acctctttga cttgaatgtt    1260
aaagagcttg aagttgagtc tcttgggtcg gaatcccag ttgttgttga tgagtctttg    1320
ccagtcacgt ggtgaaaagt ggcagtggaa tctgttgaag tcaaaatacc cccaagggg t    1380 gctgtagcca aagtagtgat tgtcgttcga ggctcctgat tggctggaaa tttgtttgta    1440
gaggtggttg ttgtaggtgg gcagggccca ggttcgggtg ctggtggtga tgactctgtc    1500
gcccatccat gtggaatcgc aatgccaatt tcccgaggaa ttacccactc cgtcggcgcc    1560
ctcgttattg tctgccattg gtgcgccact gcctgtagcc atcgtattag ttcccagacc    1620
agagggggct gctggtggct gtccgagagg ctggggtca ggtactgagt ctgcgtctcc    1680
agtctgacca aaattcaatc ttttcttgc aggctgctgg cccgcctttc cggttcccga    1740
ggaggagtct ggctccacag gagagtgctc taccggcctc ttttttcccg gagccgtctt    1800
aacaggttcc tcaaccaggc ccagaggttc aagaaccctc tttttcgcct ggaagactgc    1860
tcgtccgagg ttgcccccaa aagaggtatc ttctttaagg cgctcctgaa actccgcgtc    1920
ggcgtggttg tacttgaggt acgggttgtc tccgctgtcg agctgccggt cgtaggcttt    1980
gtcgtgctcg agggccgcgg cgtctgcctc gttgaccggc tctcccttgt cgagtccgtt    2040
gaagggtccg aggtacttgt acccaggaag cacaagaccc ctgctgtcgt ccttatgccg    2100
ctctgcgggc tttggtggtg gtgggccagg tttgagcttc caccactgtc ttattccttc    2160
agagagagtg tcctcgagcc aatcgggtag ataaccgtcg gcagccataa actgccagct    2220
cttagatgag ctggcagagt cgtatgattg taaataaaat gtaatttaca gtatagtatt    2280
```

```
ttaattaata tacaaatgat ttgataataa ttcttattta actataatat attgtgttgg    2340
gttgaattaa aggtc                                                     2355

<210> SEQ ID NO 55
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atcatggaga taattaaaat gataaccatc tcgcaaataa ataagtattt tactgttttc      60
gtaacagttt tgtaataaaa aaacctataa at                                   92

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atacctgcct gctcttcgat ctaacgaaga gctggcagtt tatggcc                   47

<210> SEQ ID NO 57
<211> LENGTH: 1866
<212> TYPE: DNA
<213> ORGANISM: Adeno-associated virus

<400> SEQUENCE: 57
atggccgggt tttacgagat tgtgattaag gtccccagcg accttgacga gcatctgccc      60
ggcatttctg acagctttgt gaactgggtg gccgagaagg agtgggagtt gccgccagat     120
tctgacatgg atctgaatct gattgagcag gcaccectga ccgtggccga aagctgcag     180 cgcgactttc tgacggagtg cgccgtgtgt agtaaggccc cggaggccct tttctttgtg     240
caatttgaga agggagagag ctacttccac atgcacgtgc tcgtggaaac caccggggtg     300
aaatccatgg tttttgggacg tttcctgagt cagattcgcg aaaaactgat tcagagaatt     360
taccgcggga tcgagccgac tttgccaaac tggttcgcgg tcacaaagac cagaaacggc     420
gccggaggcg gaacaaggt ggtggacgag tgctacatcc ccaattactt gctccccaaa     480
acccagcctg agctccagtg gcgtggact aatatggaac agtatttaag cgcctgttttg     540 aatctcacgg agcgtaaacg gttggtggcg cagcatctga cgcacgtgtc gcagacgcag     600
gagcagaaca aagagaatca gaatcccaat tctgacgcgc cggtgatcag atcaaaaact     660
tcagccaggt acatggagct ggtcgggtgg ctcgtggaca aggggattac ctcggagaag     720
cagtggatcc aggaggacca ggcctcatac atctccttca atgcggcctc caactcgcgg     780
tcccaaatca aggctgcctt ggacaatgcg ggaaagatta tgagcctgac taaaaccgcc     840
cccgactacc tggtgggcca gcagcccgtg gaggacattt ccagcaatcg gatttataaa     900
attttggaac taaacgggta cgatcccaa tatgcggctt ccgtctttct gggatgggcc     960
acgaaaaagt tcggcaagag gaacaccatc tggctgtttg gcctgcaac taccgggaag     1020 accaacatcg cggaggccat agcccacact gtgcccttct acgggtgcgt aaactggacc     1080
aatgagaact ttccttcaa cgactgtgtc gacaagatgg tgatctggtg ggaggagggg     1140
```

```
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agacttttc cggtgggcaa aggatcacgt ggttgaggtg    1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                              1866

<210> SEQ ID NO 58
<211> LENGTH: 2038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atcatggaga taattaaaat gataaccatc tcgcaaataa ataagtattt tactgttttc     60
gtaacagttt tgtaataaaa aaacctataa ataataatta aaatgagact taatttgaat   120
tatttacaat catacctgcc tgctcttcga tctaacgaag agctggcagt ttatggccgg   180
gttttacgag attgtgatta aggtccccag cgaccttgac gagcatctgc ccggcatttc   240
tgacagcttt gtgaactggg tggccgagaa ggagtgggag ttgccgccag attctgacat   300
ggatctgaat ctgattgagc aggcacccct gaccgtggcc gagaagctgc agcgcgactt   360
tctgacggag tggcgccgtg tgagtaaggc cccggaggcc cttttctttg tgcaatttga   420
gaagggagag agctacttcc acatgcacgt gctcgtggaa accaccgggg tgaaatccat   480
ggttttggga cgtttcctga gtcagattcg cgaaaaactg attcagagaa tttaccgcgg   540
gatcgagccg actttgccaa actggttcgc ggtcacaaag accagaaacg cgccggagg    600 cgggaacaag gtggtggacg agtgctacat ccccaattac ttgctcccca aacccagcc    660 tgagctccag tgggcgtgga ctaatatgga acagtattta agcgcctgtt tgaatctcac   720
ggagcgtaaa cggttggtgg cgcagcatct gacgcacgtg tcgcagacgc aggagcagaa   780
caaagagaat cagaatccca attctgacgc gccggtgatc agatcaaaaa cttcagccag   840
gtacatggag ctggtcgggt ggctcgtgga caagggatt acctcggaga agcagtggat    900
ccaggaggac caggcctcat acatctcctt caatgcggcc tccaactcgc ggtcccaaat   960
caaggctgcc ttggacaatg cgggaaagat tatgagcctg actaaaaccg cccccgacta  1020
cctggtgggc cagcagcccg tggaggacat ttccagcaat cggatttata aaattttgga  1080
actaaacggg tacgatcccc aatatgcggc ttccgtcttt ctgggatggg ccacgaaaaa  1140
gttcggcaag aggaacacca tctggctgtt tgggcctgca actaccggga agaccaacat  1200
cgcggaggcc atagcccaca ctgtgcccct ctacgggtgc gtaaactgga ccaatgagaa  1260
```

```
ctttcccttc aacgactgtg tcgacaagat ggtgatctgg tgggaggagg ggaagatgac    1320
cgccaaggtc gtggagtcgg ccaaagccat tctcggagga agcaaggtgc gcgtggacca    1380
gaaatgcaag tcctcggccc agatagaccc gactcccgtg atcgtcacct ccaacaccaa    1440
catgtgcgcc gtgattgacg ggaactcaac gaccttcgaa caccagcagc cgttgcaaga    1500
ccggatgttc aaatttgaac tcacccgccg tctggatcat gactttggga aggtcaccaa    1560
gcaggaagtc aaagactttt tccggtgggc aaaggatcac gtggttgagg tggagcatga    1620
attctacgtc aaaaagggtg gagccaagaa aagacccgcc cccagtgacg cagatataag    1680
tgagcccaaa cgggtgcgcg agtcagttgc gcagccatcg acgtcagacg cggaagcttc    1740
gatcaactac gcagacaggt accaaaacaa atgttctcgt cacgtgggca tgaatctgat    1800
gctgtttccc tgcagacaat gcgagagaat gaatcgaat tcaaatatct gcttcactca    1860
cggacagaaa gactgtttag agtgctttcc cgtgtcagaa tctcaacccg tttctgtcgt    1920
caaaaaggcg tatcagaaac tgtgctacat tcatcatatc atgggaaagg tgccagacgc    1980
ttgcactgcc tgcgatctgg tcaatgtgga tttggatgac tgcatctttg aacaataa     2038
```

<210> SEQ ID NO 59
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
ttaacacttt aaccttataa tacacatgct gagaatacta attatcgtaa tgatgatagt    60
atcctatagg aattaatctt atataatgat tagaagctt                           99
```

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
acacaccggt ggaggcacgt cctt                                           24
```

<210> SEQ ID NO 61
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
tgagcacggt aaccttataa tacacctgcc gagaatacta attatcgtaa tgatgatagt    60
atcctctcgg aagtaatctt atataatgtt tagaagctt                           99
```

<210> SEQ ID NO 62
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tgagcacggt gaccttagaa tacacctgcc gagtaagctc attgtcgtaa tgatgatagt     60
atcctctcgg catcagtcta gcctgaggct tagccgctt                           99

<210> SEQ ID NO 63
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgagcacggt gaccttagaa ggcacctgcc gagtaggctc attgtcgtcc tgatgatagt     60
agcctctcgg catgagtctc gcctgctgcg gagccgctt                           99

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gggggatcct gtttagatgg ctgccgacgg ttatctaccc g                        41

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gggggatcct gtttagatgt tggccgacgg ttatctaccc g                        41

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gggggatcct gttttatgt tggccgacgg ttatctaccc g                         41

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
actcgacgaa gacttgatca cccgggggat cctgttttta tgttg                    45

<210> SEQ ID NO 68
<211> LENGTH: 50
<212> TYPE: PRT
<213> ORGANISM: Artificial Sequence
<220> FEATURE:
<223> OTHER INFORMATION: Description of Artificial Sequence: Synthetic

```
                    polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 68

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Gly Gly Ser Gly Gly Gly Gly Ser Gly Gly Gly Gly Ser
1               5                   10                  15

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Gly Gly Ser
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
```

```
<221> NAME/KEY: MOD_RES
<222> LOCATION: (4)..(4)
<223> OTHER INFORMATION: Any amino acid

<400> SEQUENCE: 72

Asp Xaa Glu Xaa Asn Pro Gly Pro
1               5
```

ENGINEERED UNTRANSLATED REGIONS (UTR) FOR AAV PRODUCTION

CROSS REFERENCE TO RELATED APPLICATIONS

This application is a 35 U.S.C. § 371 U.S. National Stage Entry of International Application No. PCT/US2019/036922, filed Jun. 13, 2019 and entitled ENGINEERED UNTRANSLATED REGIONS (UTR) FOR AAV PRODUCTION, which claims priority to U.S. Provisional Patent Application No. 62/684,410, filed Jun. 13, 2018, entitled UNTRANSLATED REGION (UTR) REGULATORY CONSTRUCTS, and U.S. Provisional Patent Application No. 62/691,743, filed Jun. 29, 2018, entitled UNTRANSLATED REGION (UTR) REGULATORY CONSTRUCTS, and U.S. Provisional Patent Application No. 62/741,746, filed Oct. 5, 2018, entitled UNTRANSLATED REGION (UTR) REGULATORY CONSTRUCTS FOR AAV CAP SEQUENCES, and U.S. Provisional Patent Application No. 62/741,779, filed Oct. 5, 2018, entitled UNTRANSLATED REGION (UTR) REGULATORY CONSTRUCTS FOR AAV REP SEQUENCES, the contents of which are each incorporated herein by reference in their entirety.

REFERENCE TO SEQUENCE LISTING

The present application is being filed along with a Sequence Listing in electronic format. The Sequence Listing is provided as a file entitled 20571511US371_SL.txt, created on Dec. 11, 2020, which is 29,228 bytes in size. The information in the electronic format of the sequence listing is incorporated herein by reference in its entirety.

FIELD OF THE DISCLOSURE

The present disclosure describes methods and systems for use in the production of recombinant adeno-associated virus (rAAV) particles. In certain embodiments, the production process and system include engineered untranslated regions (UTR) which allow for the controlled expression of AAV capsid proteins, such as VP1, VP2 and VP3. In certain embodiments, the production process and system include engineered untranslated regions (UTR) which allow for the controlled expression of non-structural AAV replication proteins, such as Rep78 and Rep52.

BACKGROUND

AAVs have emerged as one of the most widely studied and utilized viral vectors for gene transfer to mammalian cells. See, e.g., Tratschin et al., *Mol. Cell Biol.*, 5(11):3251-3260 (1985) and Grimm et al., *Hum. Gene Ther.*, 10(15):2445-2450 (1999), the contents of which are herein incorporated by reference in their entirety. Adeno-associated viral (AAV) vectors are promising candidates for therapeutic gene delivery and have proven safe and efficacious in clinical trials. The design and production of improved AAV particles for this purpose is an active field of study.

With the advent of development in the AAV field, there remains a need for improved systems and methods for producing AAV vectors (such as AAV particles) and corresponding gene therapy production materials such as Baculoviral Expression Vectors (BEVs).

SUMMARY

The present disclosure presents viral expression constructs which include an expression control sequence and a protein-coding nucleotide sequence. In some embodiments, the viral expression construct includes an expression control sequence operably linked to a protein-coding nucleotide sequence. In some embodiments, the expression control sequence includes an engineered polynucleotide. In some embodiments, the engineered polynucleotide is an engineered untranslated region (UTR). In some embodiments, the engineered UTR polynucleotide functions as a 5' UTR.

In some embodiments, the protein-coding nucleotide sequence encodes a structural capsid protein. In some embodiments, the protein-coding nucleotide sequence encodes VP1, VP2, VP3 or a combination thereof. In some embodiments, the protein-coding nucleotide sequence encodes a non-structural replication protein. In some embodiments, the protein-coding nucleotide sequence encodes Rep78, Rep68, Rep52 and Rep40 or a combination thereof.

In some embodiments, the expression control sequence includes a promoter. In some embodiments, the expression control sequence includes a late insect promoter or a very-later insect promoter. In some embodiments, the expression control sequence includes a promoter selected from Op-EI, EI, ΔEI, EI-1, pH, PIO, polH (polyhedron), ΔpolH, Dmhsp70, Hr1, Hsp70, 4×Hsp27 EcRE+minimal Hsp70, IE, IE-1, ΔIE-1, ΔIE, p10, Δp10, p5, p19, p35, p40, p6.9, and variations or derivatives thereof. In some embodiments, the expression control sequence includes a promoter selected from polH, p10, p6.9, and variations or derivatives thereof. In some embodiments, the expression control sequence includes a p10 promoter. In some embodiments, the expression control sequence includes a polH promoter.

In some embodiments, the engineered UTR includes a hairpin structure. In some embodiments, the engineered UTR includes a hairpin structure of the present disclosure. In some embodiments, the hairpin structure includes a 5' flanking region (i.e. upstream region), a stem region, a loop region, and a 3' flanking region (i.e. downstream region). In some embodiments, the hairpin structure includes a 5' flanking region, a stem region, a loop region, a stem-complement region, and a 3' flanking region.

In some embodiments, the hairpin structure is encoded by a hairpin sequence. In some embodiments, the hairpin sequence includes a leader sequence. In some embodiments, the 5' flanking region (i.e. upstream region) is encoded by a 5' flanking sequence. In some embodiments, the 3' flanking region (i.e. downstream region) is encoded by a 3' flanking sequence. In some embodiments, the stem region is encoded by a stem sequence. In some embodiments, the loop region is encoded by a loop sequence. In some embodiments, the stem-complement region is encoded by a stem-complement sequence.

In some embodiments, an expression control sequence includes a start codon for translation of a protein-coding nucleotide sequence. In some embodiments, the expression control sequence includes an engineered UTR which includes a start codon for translation of a protein-coding nucleotide sequence. In some embodiments, the engineered UTR includes a hairpin structure and a start codon for translation of a protein-coding nucleotide sequence. In some embodiments, the hairpin structure is located 5' of the start codon. In some embodiments, the start codon is included in the hairpin structure. In some embodiments, the start codon is included in the loop region of the hairpin structure. In some embodiments, the start codon is included in the stem-complement region of the hairpin structure. In some embodiments, the start codon is included in the 3' flanking (i.e. downstream) region of the hairpin structure. In some embodiments, the distance between the 3' end of the loop region and the start codon is from 1-30 nucleotides. In some embodiments, the distance between the 3' end of the stem-complement region and the start codon is from 1-30 nucleotides. In some embodiments, the start codon is ATG or ACG. In some embodiments, the start codon is CTG, TTG, or GTG.

In some embodiments, the expression control sequence includes an engineered UTR which includes a Kozak nucleotide sequence or modified Kozak nucleotide sequence of the present disclosure. In some embodiments, the Kozak nucleotide sequence or modified Kozak nucleotide sequence comprises an ATG start codon. In certain embodiments, the modified Kozak nucleotide sequence comprises an ACG start codon.

In some embodiments, the engineered 5' UTR includes a hairpin structure selected from the hairpin structures presented in Table 1. In some embodiments, the engineered 5' UTR includes a hairpin structure encoded by a hairpin nucleotide sequence selected from SEQ ID NO: 1-16. In some embodiments, the engineered 5' UTR includes a hairpin structure encoded by a nucleotide sequence having at least 60% identity, at least 65% identity, at least 70% identity, at least 75% identity, at least 80% identity, at least 85% identity, at least 90% identity or at least 95% identity to SEQ ID NO: 1-16.

In some embodiments, the engineered 5' UTR includes a Hairpin 9 structure, or a component thereof. In some embodiments, the engineered 5' UTR includes a hairpin structure encoded by a hairpin nucleotide sequence comprising SEQ ID NO: 9. In some embodiments, the viral expression constructs include an expression control sequence which includes a Hairpin 9 structure, and a protein-coding nucleotide sequence which encodes a structural capsid protein (such as VP1, VP2, VP3 or a combination thereof). In some embodiments, the viral expression construct includes an expression control sequence which includes a p10 promoter and a Hairpin 9 structure, and a protein-coding nucleotide sequence which encodes a structural capsid protein (such as VP1, VP2, VP3 or a combination thereof).

In some embodiments, the engineered 5' UTR includes a Hairpin 12 structure, or a component thereof. In some embodiments, the engineered 5' UTR includes a hairpin structure encoded by a hairpin nucleotide sequence comprising SEQ ID NO: 12. In some embodiments, the viral expression construct includes an expression control sequence which includes a Hairpin 12 structure, and a protein-coding nucleotide sequence which encodes a non-structural replication protein (such as Rep78, Rep68, Rep52 and Rep40 or a combination thereof). In some embodiments, the viral expression constructs includes an expression control sequence which includes a polH promoter and a Hairpin 12 structure, and a protein-coding nucleotide sequence which encodes a non-structural replication protein (such as Rep78, Rep68, Rep52 and Rep40 or a combination thereof).

In some embodiments, the engineered 5' UTR includes a hairpin structure which includes a 5' flanking region (i.e. upstream region) encoded by a nucleotide sequence selected from atacgact, atac, and SEQ ID NO: 17-20. In some embodiments, the engineered 5' UTR includes a hairpin structure which includes an upstream region encoded by a nucleotide sequence having at least 60% identity, at least 65% identity, at least 70% identity, at least 75% identity, at least 80/o identity, at least 85% identity, at least 90% identity or at least 95% identity to a nucleotide sequence selected from atacgact, atac, and SEQ ID NO: 17-20.

In some embodiments, the engineered 5' UTR includes a hairpin structure which includes a 3' flanking region (i.e. downstream region) encoded by a nucleotide sequence selected from tttatggct, attatggct, tatatggct, ttaatggct, taaatggct, ataatggct, and SEQ ID NO: 34-35. In some embodiments, the engineered 5' UTR includes a hairpin structure which includes an downstream region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from tttatggct, attatggct, tatatggct, ttaatggct, taaatggct, ataatggct, and SEQ ID NO: 34-35.

In some embodiments, the engineered 5' UTR includes a hairpin structure which includes a stem region encoded by a nucleotide sequence selected from cggc, ctgcc and SEQ ID NO: 21-31. In some embodiments, the engineered 5' UTR includes a hairpin structure which includes an stem region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from cggc, ctgcc and SEQ ID NO: 21-31.

In some embodiments, the engineered 5' UTR includes a hairpin structure which includes a stem complement region encoded by a nucleotide sequence selected from ggcag and SEQ ID NO: 32-33. In some embodiments, the engineered 5' UTR includes a hairpin structure which includes an stem complement region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from ggcag and SEQ ID NO: 32-33.

In some embodiments, the stem sequence and the stem-complement sequence are 100% complementary (i.e. zero mismatches). In some embodiments, the stem sequence and the stem-complement sequence include zero, one, two, three, four or five mismatches. In some embodiments, the stem sequence and the stem-complement sequence include one mismatch. In some embodiments, the stem sequence and the stem-complement sequence include two mismatches. In some embodiments, the stem sequence and the stem-complement sequence include three mismatches. In some embodiments, the stem sequence and the stem-complement sequence include 1-10 mismatches.

In some embodiments, the engineered 5' UTR includes a hairpin structure which includes a loop region encoded by a nucleotide sequence selected from tttatggct and atctaa. In some embodiments, the engineered 5' UTR includes a hairpin structure which includes a loop region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from tttatggct and atctaa.

In some embodiments, the engineered 5' UTR includes a hairpin structure which includes a leader sequence selected from SEQ ID NO: 36-51. In some embodiments, the engineered 5' UTR includes a hairpin structure which includes a leader sequence selected from SEQ ID NO: 59-63. In some embodiments, the engineered 5' UTR includes a hairpin structure which includes a leader sequence having at least 60% identity, at least 65% identity, at least 70% identity, at least 75% identity, at least 80% identity, at least 85% identity, at least 90% identity or at least 95% identity to a nucleotide sequence selected from SEQ ID NO: 36-51. In some embodiments, the engineered 5' UTR includes a hairpin structure which includes a leader sequence having at least 60% identity, at least 65% identity, at least 70% identity, at least 75% identity, at least 80% identity, at least 85% identity, at least 90% identity or at least 95% identity to a nucleotide sequence selected from SEQ ID NO: 59-63.

In some embodiments the length of the engineered 5' UTR polynucleotide is from 20-200 nucleotides, from 20-100 nucleotides, from 20-50 nucleotides or from 15 to 150 nucleotides.

In some embodiments, the engineered UTR improves the stability and protein production capability of corresponding viral production constructs. In some embodiments, the engineered UTR modulates the expression of one or more protein-coding nucleotide sequences. In some embodiments, the engineered UTR modulates ratios of proteins encoded by the protein-coding nucleotide sequences. In some embodiments, the engineering of the UTR includes changing the strength, length, sequence or tertiary structure of the UTR.

In some embodiments the engineered polynucleotide includes a start codon (e.g. ATG or ACG) and a 5' UTR sequence which will down-regulate the expression of a VP1 capsid protein relative to VP3. In some embodiments the engineered polynucleotide includes a start codon (e.g. ACG or ATG) and a 5' UTR sequence which will up-regulate the expression of a VP1 capsid protein relative to VP3.

In some embodiments the engineered polynucleotide includes a start codon (e.g. ATG or ACG) and a 5' UTR sequence which will down-regulate the expression of a VP2 capsid protein relative to VP3. In some embodiments the engineered polynucleotide includes a start codon (e.g. ACG or ATG) and a 5' UTR sequence which will up-regulate the expression of a VP2 capsid protein relative to VP3.

In some embodiments the engineered polynucleotide includes a start codon (e.g. ATG or ACG) and a 5' UTR sequence which will down-regulate the expression of a Rep78 capsid protein relative to Rep52. In some embodiments the engineered polynucleotide includes a start codon (e.g. ATG or ACG) and a 5' UTR sequence which will up-regulate the expression of a Rep78 capsid protein relative to Rep52.

In some embodiments the engineered polynucleotide includes a start codon (e.g. ATG or ACG) and a 5' UTR sequence which will down-regulate the expression of a Rep52 capsid protein relative to Rep78. In some embodiments the engineered polynucleotide includes a start codon (e.g. ATG or ACG) and a 5' UTR sequence which will up-regulate the expression of a Rep52 capsid protein relative to Rep78.

The present disclosure presents a method of altering the ratio of structural capsid proteins (i.e. VP proteins) expressed from a protein-coding nucleotide sequence which encodes structural capsid proteins (such as VP1, VP2, VP3, or a combination thereof). In some embodiments, the method includes the use of an engineered polynucleotide which includes a start codon and a 5' UTR sequence which will down-regulate the expression of a VP1 and/or VP2 capsid proteins relative to VP3. In some embodiments, the method includes the use of an engineered polynucleotide which includes a start codon and a 5' UTR sequence which will up-regulate the expression of a VP1 and/or VP2 capsid proteins relative to VP3.

In some embodiments, the method results in a VP1:VP2:VP3 expression ratio of 0-3:0-3:10. In some embodiments, the method results in a VP1:VP2:VP3 expression ratio of 0.5-2:0.5-2:10. In some embodiments, the method results in a VP1:VP2:VP3 expression ratio of about 1:1:10. In some embodiments, the method results in a VP1:VP3 expression ratio of 0-3:10, 0.5-2:10, or about 1:10. In some embodiments, the method results in a VP2:VP3 expression ratio of 0-3:10, 0.5-2:10, or about 1:10.

The present disclosure presents a method of altering the ratio of non-structural replication proteins (i.e. Rep proteins) expressed from a protein-coding nucleotide sequence which encodes non-structural replications proteins (such as Rep78, Rep52, or a combination thereof). In some embodiments, the method includes the use of an engineered polynucleotide which includes a start codon and a 5' UTR sequence which will down-regulate the expression of a Rep52 capsid proteins relative to Rep78. In some embodiments, the method includes the use of an engineered polynucleotide which includes a start codon and a 5' UTR sequence which will up-regulate the expression of a Rep52 capsid proteins relative to Rep78. In some embodiments, the method includes the use of an engineered polynucleotide which includes a start codon and a 5' UTR sequence which will down-regulate the expression of a Rep78 capsid proteins relative to Rep52. In some embodiments, the method includes the use of an engineered polynucleotide which includes a start codon and a 5' UTR sequence which will up-regulate the expression of a Rep78 capsid proteins relative to Rep52.

In some embodiments, the method results in a ratio of p5 Rep proteins (Rep78 and Rep68) to p19 Rep proteins (Rep52 and Rep40) below 1:1. In some embodiments, the method results in a p5:p19 ratio of 1:1-33, 1:1-30, 1:1-25, 1:1-20, 1:1-15, 1:1-10, 1:1-6, 1:1-5, 1:1-4, 1:1-3 or 1:1-2.

The details of various embodiments of the disclosure are set forth in the description below. Other features, objects, and advantages of the disclosure will be apparent from the description, drawings, and the claims. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

BRIEF DESCRIPTION OF THE FIGURES

The foregoing and other objects, features and advantages will be apparent from the following description of particular embodiments of the present disclosure, as illustrated in the accompanying figures. The figures are not necessarily to scale or comprehensive, with emphasis instead being placed upon illustrating the principles of various embodiments of the present disclosure.

FIG. 4 discloses SEQ ID NOS 64-66, respectively, in order of appearance.

DETAILED DESCRIPTION

I. Adeno-Associated Viruses (AAVs)

Overview

Figure 1:
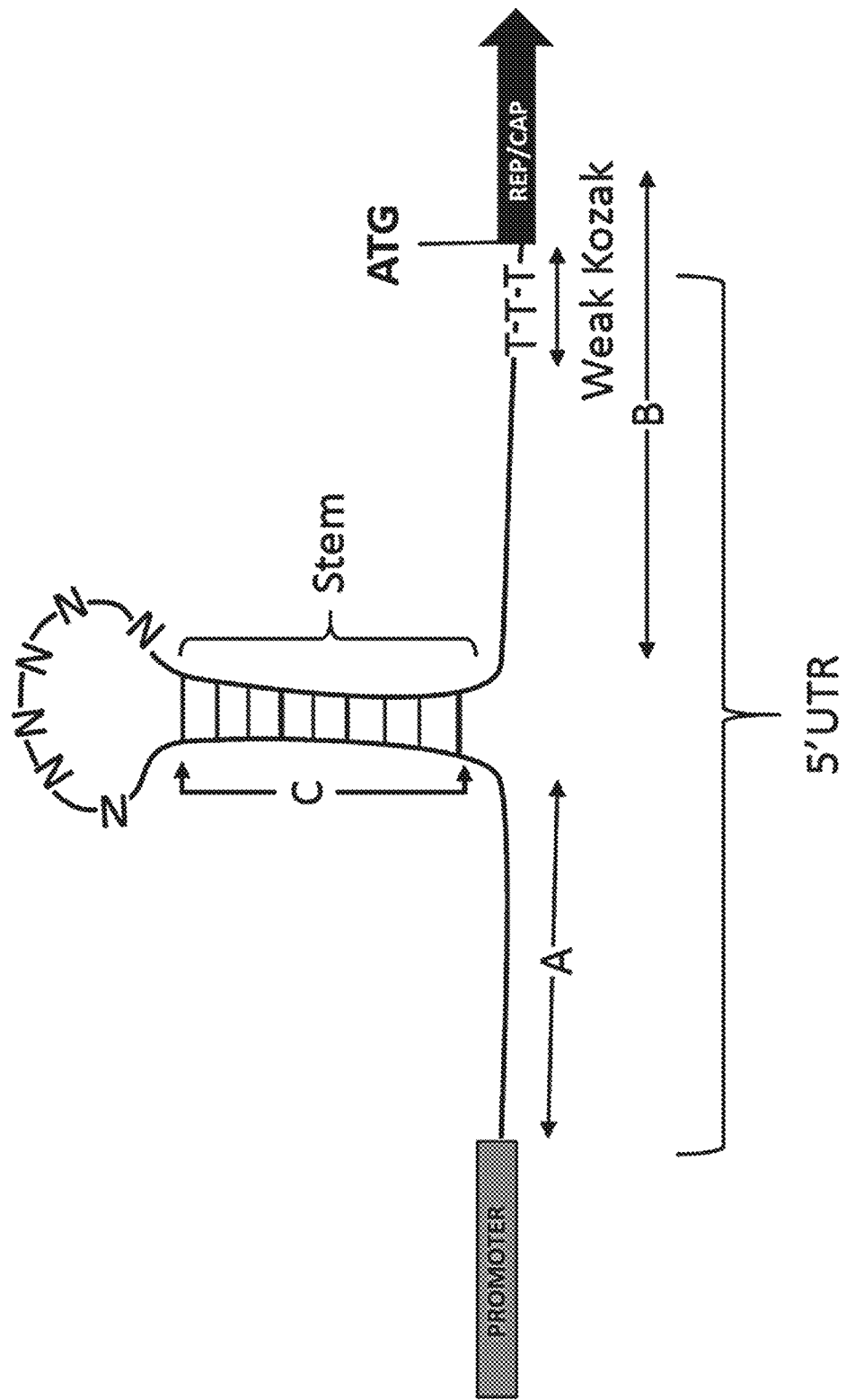
FIG. 1 is a general illustration of one embodiment of an engineered polynucleotide (e.g., 5' UTR) of the present disclosure.

Adeno-associated viruses (AAV) are small non-enveloped icosahedral capsid viruses of the Parvoviridae family characterized by a single stranded DNA viral genome. Parvoviridae family viruses consist of two subfamilies: Parvovirinae, which infect vertebrates, and Densovirinae, which infect invertebrates. The Parvoviridae family includes the Dependovirus genus which includes AAV, capable of replication in vertebrate hosts including, but not limited to, human, primate, bovine, canine, equine, and ovine species.

The parvoviruses and other members of the Parvoviridae family are generally described in Kenneth I. Bems, "Parvoviridae: The Viruses and Their Replication," Chapter 69 in Fields Virology (3d Ed. 1996), the contents of which are incorporated by reference in their entirety.

AAV have proven to be useful as a biological tool due to their relatively simple structure, their ability to infect a wide range of cells (including quiescent and dividing cells) without integration into the host genome and without replicating, and their relatively benign immunogenic profile. The genome of the virus may be manipulated to contain a minimum of components for the assembly of a functional recombinant virus, or viral particle, which is loaded with or engineered to target a particular tissue and express or deliver a desired payload.

AAV Viral Genomes

The wild-type AAV viral genome is a linear, single-stranded DNA (ssDNA) molecule approximately 5,000 nucleotides (nt) in length. Inverted terminal repeats (ITRs) traditionally cap the viral genome at both the 5' and the 3' end, providing origins of replication for the viral genome. While not wishing to be bound by theory, an AAV viral genome typically includes two ITR sequences. These ITRs have a characteristic T-shaped hairpin structure defined by a self-complementary region (145 nt in wild-type AAV) at the 5' and 3' ends of the ssDNA which form an energetically stable double stranded region. The double stranded hairpin structures include multiple functions including, but not limited to, acting as an origin for DNA replication by functioning as primers for the endogenous DNA polymerase complex of the host viral replication cell.

The wild-type AAV viral genome further includes nucleotide sequences for two open reading frames, one for the four non-structural Rep proteins (Rep78, Rep68, Rep52, Rep40, encoded by Rep genes) and one for the three capsid, or structural, proteins (VP1, VP2, VP3, encoded by capsid genes or Cap genes). The Rep proteins are important for replication and packaging, while the capsid proteins are assembled to create the protein shell of the AAV, or AAV capsid. Alternative splicing and alternate initiation codons and promoters result in the generation of four different Rep proteins from a single open reading frame and the generation of three capsid proteins from a single open reading frame. Though it varies by AAV serotype, as a non-limiting example, for AAV9/hu.14 (SEQ ID NO: 123 of U.S. Pat. No. 7,906,111, the contents of which are herein incorporated by reference in their entirety) VP1 refers to amino acids 1-736, VP2 refers to amino acids 138-736, and VP3 refers to amino acids 203-736. In other words, VP1 is the full-length capsid sequence, while VP2 and VP3 are shorter components of the whole. As a result, changes in the sequence in the VP3 region, are also changes to VP1 and VP2, however, the percent difference as compared to the parent sequence will be greatest for VP3 since it is the shortest sequence of the three. Though described here in relation to the amino acid sequence, the nucleic acid sequence encoding these proteins can be similarly described. Together, the three capsid proteins assemble to create the AAV capsid protein. While not wishing to be bound by theory, the AAV capsid protein typically includes a molar ratio of 1:1:10 of VP1:VP2:VP3. As used herein, an "AAV serotype" is defined primarily by the AAV capsid. In some instances, the ITRs are also specifically described by the AAV serotype (e.g., AAV2/9).

For use as a biological tool, the wild-type AAV viral genome can be modified to replace the rep/cap sequences with a nucleic acid sequence including a payload region with at least one ITR region. Typically, in recombinant AAV viral genomes there are two ITR regions. The rep/cap sequences can be provided in trans during production to generate AAV particles.

In addition to the encoded heterologous payload, AAV vectors may include the viral genome, in whole or in part, of any naturally occurring and/or recombinant AAV serotype nucleotide sequence or variant. AAV variants may have sequences of significant homology at the nucleic acid (genome or capsid) and amino acid levels (capsids), to produce constructs which are generally physical and functional equivalents, replicate by similar mechanisms, and assemble by similar mechanisms. See Chiorini et al., J. Vir. 71: 6823-33(1997); Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 8635-47 (2000), the contents of each of which are incorporated herein by reference in their entirety.

In certain embodiments, AAV particles, viral genomes and/or payloads of the present disclosure, and the methods of their use, may be as described in WO2017189963, the contents of which are herein incorporated by reference in their entirety.

AAV particles of the present disclosure may be formulated in any of the gene therapy formulations of the disclosure including any variations of such formulations apparent to those skilled in the art. The reference to "AAV particles", "AAV particle formulations" and "formulated AAV particles" in the present application refers to the AAV particles which may be formulated and those which are formulated without limiting either.

In certain embodiments, AAV particles of the present disclosure are recombinant AAV (rAAV) viral particles which are replication defective, lacking sequences encoding functional Rep and Cap proteins within their viral genome. These defective AAV particles may lack most or all parental coding sequences and essentially carry only one or two AAV ITR sequences and the nucleic acid of interest (i.e. payload) for delivery to a cell, a tissue, an organ or an organism.

In certain embodiments, the viral genome of the AAV particles of the present disclosure includes at least one control element which provides for the replication, transcription and translation of a coding sequence encoded therein. Not all of the control elements need always be present as long as the coding sequence is capable of being replicated, transcribed and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

According to the present disclosure, AAV particles for use in therapeutics and/or diagnostics include a virus that has been distilled or reduced to the minimum components necessary for transduction of a nucleic acid payload or cargo of interest. In this manner, AAV particles are engineered as vehicles for specific delivery while lacking the deleterious replication and/or integration features found in wild-type viruses.

AAV particles of the present disclosure may be produced recombinantly and may be based on adeno-associated virus (AAV) parent or reference sequences. As used herein, a "vector" is any molecule or moiety which transports, transduces or otherwise acts as a carrier of a heterologous molecule such as the nucleic acids described herein.

In addition to single stranded AAV viral genomes (e.g., ssAAVs), the present disclosure also provides for self-complementary AAV (scAAVs) viral genomes. scAAV vector genomes contain DNA strands which anneal together to form double stranded DNA. By skipping second strand synthesis, scAAVs allow for rapid expression in the cell.

In certain embodiments, the AAV viral genome of the present disclosure is a scAAV. In certain embodiments, the AAV viral genome of the present disclosure is a ssAAV.

Methods for producing and/or modifying AAV particles are disclosed in the art, such as pseudotyped AAV particles (PCT Patent Publication Nos. WO200028004; WO200123001; WO2004112727; WO 2005005610 and WO 2005072364, the content of each of which is incorporated herein by reference in its entirety).

AAV particles may be modified to enhance the efficiency of delivery. Such modified AAV particles can be packaged efficiently and be used to successfully infect the target cells at high frequency and with minimal toxicity. In certain embodiments the capsids of the AAV particles are engineered according to the methods described in US Publication Number US 20130195801, the contents of which are incorporated herein by reference in their entirety.

In certain embodiments, the AAV particles including a payload region encoding a polypeptide or protein of the present disclosure, and may be introduced into mammalian cells.

Inverted Terminal Repeats (ITRs)

The AAV particles of the present disclosure include a viral genome with at least one ITR region and a payload region. In certain embodiments, the viral genome has two ITRs. These two ITRs flank the payload region at the 5' and 3' ends. The ITRs function as origins of replication including recognition sites for replication. ITRs include sequence regions which can be complementary and symmetrically arranged. ITRs incorporated into viral genomes of the present disclosure may be included of naturally occurring polynucleotide sequences or recombinantly derived polynucleotide sequences.

The ITRs may be derived from the same serotype as the capsid, or a derivative thereof. The ITR may be of a different serotype than the capsid. In certain embodiments, the AAV particle has more than one ITR In a non-limiting example, the AAV particle has a viral genome including two ITRs. In certain embodiments, the ITRs are of the same serotype as one another. In another embodiment, the ITRs are of different serotypes. Non-limiting examples include zero, one or both of the ITRs having the same serotype as the capsid. In certain embodiments both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In certain embodiments, the ITRs are 140-142 nucleotides in length. Non-limiting examples of ITR length are 102, 130, 140, 141, 142, 145 nucleotides in length, and those having at least 95% identity thereto.

In certain embodiments, each ITR may be 141 nucleotides in length. In certain embodiments, each ITR may be 130 nucleotides in length. In certain embodiments, each ITR may be 119 nucleotides in length.

In certain embodiments, the AAV particles include two ITRs and one ITR is 141 nucleotides in length and the other ITR is 130 nucleotides in length. In certain embodiments, the AAV particles include two ITRs and both ITR are 141 nucleotides in length.

Promoters

In certain embodiments, the payload region of the viral genome includes at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the polypeptides of the present disclosure in a target cell may require a specific promoter, including but not limited to, a promoter that is species specific, inducible, tissue-specific, or cell cycle-specific (see Parr et al., *Nat. Med.* 3:1145-9 (1997); the contents of which are herein incorporated by reference in their entirety).

In certain embodiments, the promoter is deemed to be efficient when it drives expression of the polypeptide(s) encoded in the payload region of the viral genome of the AAV particle. In certain embodiments, the promoter is a promoter deemed to be efficient when it drives expression in the cell being targeted. In certain embodiments, the promoter is a promoter having a tropism for the cell being targeted. In certain embodiments, the promoter is a promoter having a tropism for a viral production cell.

In certain embodiments, the promoter drives expression of the payload for a period of time in targeted cells or tissues. Expression driven by a promoter may be for a period of 1-31 days (or any value or range therein), 1-23 months (or any value or range therein), 2-10 years (or any value or range therein), or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter can be a weak promoter for sustained expression of a payload in nervous (e.g. CNS) cells or tissues.

In certain embodiments, the promoter drives expression of the polypeptides of the present disclosure for at least 1-11 months (or any individual value therein), 2-65 years (or any individual value therein), or more than 65 years.

Promoters may be naturally occurring or non-naturally occurring. Non-limiting examples of promoters include viral promoters, plant promoters and mammalian promoters. In certain embodiments, the promoters may be human promoters. In certain embodiments, the promoter may be truncated or mutated.

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons or subtypes of neurons, astrocytes, or oligodendrocytes.

Non-limiting examples of muscle-specific promoters include mammalian muscle creatine kinase (MCK) promoter, mammalian desmin (DES) promoter, mammalian troponin 1 (TNNI2) promoter, and mammalian skeletal alpha-actin (ASKA) promoter (see, e.g. U.S. Patent Publication US 20110212529, the contents of which are herein incorporated by reference in their entirety)

Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In certain embodiments, the promoter may be less than 1 kb. The promoter may have a length of 200-800 nucleotides (or any value or range therein), or more than 800 nucleotides. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In certain embodiments, the promoter may be a combination of two or more components of the same or different starting or parental promoters such as, but not limited to, CMV and CBA. Each component may have a length of 200-800 nucleotides (or any value or range therein), or more than 800 nucleotides. Each component may have a length between 200-300, 200400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. In certain embodiments, the promoter is a combination of a 382 nucleotide CMV-enhancer sequence and a 260 nucleotide CBA-promoter sequence.

In certain embodiments, the viral genome includes a ubiquitous promoter. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3).

Yu et al. (Molecular Pain 2011, 7:63; the contents of which are herein incorporated by reference in their entirety) evaluated the expression of eGFP under the CAG, EF1α, PGK and UBC promoters in rat DRG cells and primary DRG cells using lentiviral vectors and found that UBC showed weaker expression than the other 3 promoters and only 10-12% glial expression was seen for all promoters. Soderblom et al. (E. Neuro 2015; the contents of which are herein incorporated by reference in its entirety) evaluated the expression of eGFP in AAV8 with CMV and UBC promoters and AAV2 with the CMV promoter after injection in the motor cortex. Intranasal administration of a plasmid containing a UBC or EF1α promoter showed a sustained airway expression greater than the expression with the CMV promoter (See e.g., Gill et al., Gene Therapy 2001, Vol. 8, 1539-1546; the contents of which are herein incorporated by reference in their entirety). Husain et al. (Gene Therapy 2009; the contents of which are herein incorporated by reference in its entirety) evaluated an HβH construct with a hGUSB promoter, a HSV-1LAT promoter and an NSE promoter and found that the HβH construct showed weaker expression than NSE in mouse brain. Passini and Wolfe (J. Virol. 2001, 12382-12392, the contents of which are herein incorporated by reference in its entirety) evaluated the long term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NFL and NFH promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH, NFL is a 650-nucleotide promoter and NFH is a 920 nucleotide promoter which are both absent in the liver but NFH is abundant in the sensory proprioceptive neurons, brain and spinal cord and NFH is present in the heart. SCN8A is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. *Identification of evolutionary conserved, functional noncoding elements in the promoter region of the sodium channel gene SCN8A*. Mamm Genome (2007) 18:723-731; and Raymond et al. *Expression of Alternatively Spliced Sodium Channel α-subunit genes*, Journal of Biological Chemistry (2004) 279(44) 46234-46241; the contents of each of which are herein incorporated by reference in their entireties).

Any of the promoters taught by the aforementioned Yu, Soderblom, Gill, Husain, Passini, Xu, Drews or Raymond may be used in the present disclosures.

In certain embodiments, the promoter is not cell specific.

In certain embodiments, the promoter is an ubiquitin c (UBC) promoter. The UBC promoter may have a size of 300-350 nucleotides. As a non-limiting example, the UBC promoter is 332 nucleotides. In certain embodiments, the promoter is a β-glucuronidase (GUSB) promoter. The GUSB promoter may have a size of 350-400 nucleotides. As a non-limiting example, the GUSB promoter is 378 nucleotides. In certain embodiments, the promoter is a neurofilament light (NFL) promoter. The NFL promoter may have a size of 600-700 nucleotides. As a non-limiting example, the NFL promoter is 650 nucleotides. In certain embodiments, the promoter is a neurofilament heavy (NFH) promoter. The NFH promoter may have a size of 900-950 nucleotides. As a non-limiting example, the NFH promoter is 920 nucleotides. In certain embodiments, the promoter is a SCN8A promoter. The SCN8A promoter may have a size of 450-500 nucleotides. As a non-limiting example, the SCN8A promoter is 470 nucleotides.

In certain embodiments, the promoter is a frataxin (FXN) promoter. In certain embodiments, the promoter is a phosphoglycerate kinase 1 (PGK) promoter. In certain embodiments, the promoter is a chicken β-actin (CBA) promoter, or variant thereof. In certain embodiments, the promoter is a CB6 promoter. In certain embodiments, the promoter is a minimal CB promoter. In certain embodiments, the promoter is a cytomegalovirus (CMV) promoter. In certain embodiments, the promoter is a H1 promoter. In certain embodiments, the promoter is a CAG promoter. In certain embodiments, the promoter is a GFAP promoter. In certain embodiments, the promoter is a synapsin promoter. In certain embodiments, the promoter is an engineered promoter. In certain embodiments, the promoter is a liver or a skeletal muscle promoter. Non-limiting examples of liver promoters include human α-1-antitrypsin (hAAT) and thyroxine binding globulin (TBG). Non-limiting examples of skeletal muscle promoters include Desmin, MCK or synthetic C5-12. In certain embodiments, the promoter is a RNA pol III promoter. As a non-limiting example, the RNA pol III promoter is U6. As a non-limiting example, the RNA pol III promoter is H1. In certain embodiments, the promoter is a cardiomyocyte-specific promoter. Non-limiting examples of cardiomyocyte-specific promoters include αMHC, cTnT, and CMV-MLC2k. In certain embodiments, the viral genome includes two promoters. As a non-limiting example, the promoters are an EF1α promoter and a CMV promoter.

In certain embodiments, the viral genome includes an enhancer element, a promoter and/or a 5' UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5' UTR/intron may be, but is not limited to, SV40, and CBA-MVM. As a non-limiting example, the enhancer, promoter and/or intron used in combination may be: (1) CMV enhancer, CMV promoter, SV40 5' UTR intron; (2) CMV enhancer, CBA promoter, SV 40 5' UTR intron; (3) CMV enhancer, CBA promoter, CBA-MVM 5' UTR intron; (4) UBC promoter; (5) GUSB promoter; (6) NSE promoter; (7) Synapsin promoter; (8) MeCP2 promoter and (9) GFAP promoter.

In certain embodiments, the viral genome includes an engineered promoter.

In another embodiment, the viral genome includes a promoter from a naturally expressed protein.

Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genomes of the AAV particles of the present disclosure to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'. In certain embodiments, the 5' UTR in the viral genome includes a Kozak sequence. In certain embodiments, the 5' UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-α, possess two or more overlapping UUAUUUA(U/A)(U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, (e.g., payload regions of viral genomes), one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In certain embodiments, the 3' UTR of the viral genome may include an oligo(dT) sequence for templated addition of a poly-A tail.

In certain embodiments, the viral genome may include at least one miRNA seed, binding site or full sequence. MicroRNAs (or miRNA or miR) are 19-25 nucleotide noncoding RNAs that bind to the sites of nucleic acid targets and down-regulate gene expression either by reducing nucleic acid molecule stability or by inhibiting translation. A microRNA sequence includes a "seed" region, i.e., a sequence in the region of positions 2-8 of the mature microRNA, which sequence has perfect Watson-Crick complementarity to the miRNA target sequence of the nucleic acid.

In certain embodiments, the viral genome may be engineered to include, alter or remove at least one miRNA binding site, sequence or seed region.

Any UTR from any gene known in the art may be incorporated into the viral genome of the AAV particle. These UTRs, or portions thereof, may be placed in the same orientation as in the gene from which they were selected, or they may be altered in orientation or location. In certain embodiments, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In certain embodiments, the viral genome of the AAV particle includes at least one artificial UTRs which is not a variant of a wild type UTR.

In certain embodiments, the viral genome of the AAV particle includes UTRs which have been selected from a family of transcripts whose proteins share a common function, structure, feature or property.

Polyadenylation Sequence

In certain embodiments, the viral genome of the AAV particles of the present disclosure include at least one polyadenylation sequence. The viral genome of the AAV particle may include a polyadenylation sequence between the 3' end of the payload coding sequence and the 5' end of the 3' ITR.

In certain embodiments, the polyadenylation sequence or "polyA sequence" may range from absent to about 500 nucleotides in length. The polyadenylation sequence may be, but is not limited to, 1-500 nucleotides in length (or any value or range therein).

In certain embodiments, the polyadenylation sequence is 127 nucleotides in length. In certain embodiments, the polyadenylation sequences is 477 nucleotides in length. In certain embodiments, the polyadenylation sequence is 552 nucleotides in length.

Linkers

Viral genomes of the present disclosure may be engineered with one or more spacer or linker regions to separate coding or non-coding regions.

In certain embodiments, the payload region of the AAV particle may optionally encode one or more linker sequences. In some cases, the linker may be a peptide linker that may be used to connect the polypeptides encoded by the payload region. Some peptide linkers may be cleaved after expression to separate polypeptide domains, allowing assembly of mature protein fragments. Linker cleavage may be enzymatic. In some cases, linkers include an enzymatic cleavage site to facilitate intracellular or extracellular cleavage. Some payload regions encode linkers that interrupt polypeptide synthesis during translation of the linker sequence from an mRNA transcript. Such linkers may facilitate the translation of separate protein domains (e.g., heavy and light chain antibody domains) from a single transcript. In some cases, two or more linkers are encoded by a payload region of the viral genome.

In certain embodiments, payload regions encode linkers including furin cleavage sites. Furin is a calcium dependent serine endoprotease that cleaves proteins just downstream of a basic amino acid target sequence (Arg-X-(Arg/Lys)-Arg) (Thomas, G., 2002. Nature Reviews Molecular Cell Biology 3(10): 753-66; the contents of which are herein incorporated by reference in its entirety). Furin is enriched in the trans-golgi network where it is involved in processing cellular precursor proteins. Furin also plays a role in activating a number of pathogens. This activity can be taken advantage of for expression of polypeptides of the disclosure.

In certain embodiments, payload regions encode linkers including 2A peptides. 2A peptides are small "self-cleaving" peptides (18-22 amino acids) derived from viruses such as foot-and-mouth disease virus (F2A), porcine teschovirus-1 (P2A), Thoseaasigna virus (T2A), or equine rhinitis A virus (E2A). The 2A designation refers specifically to a region of picornavirus polyproteins that lead to a ribosomal skip at the glycyl-prolyl bond in the C-terminus of the 2A peptide (Kim, J. H. et al., 2011. PLoS One 6(4): e18556; the contents of which are herein incorporated by reference in its entirety). This skip results in a cleavage between the 2A peptide and its immediate downstream peptide. As opposed to IRES linkers, 2A peptides generate stoichiometric expression of proteins flanking the 2A peptide and their shorter length can be advantageous in generating viral expression vectors.

In certain embodiments, payload regions encode linkers including IRES. Internal ribosomal entry site (IRES) is a nucleotide sequence (>500 nucleotides) that allows for initiation of translation in the middle of an mRNA sequence (Kim, J. H. et al., 2011. PLoS One 6(4): e18556; the contents of which are herein incorporated by reference in its entirety). Use of an IRES sequence ensures co-expression of genes before and after the IRES, though the sequence following the IRES may be transcribed and translated at lower levels than the sequence preceding the IRES sequence.

In certain embodiments, the payload region may encode one or more linkers including cathepsin, matrix metalloproteinases or legumain cleavage sites. Such linkers are described e.g. by Cizeau and Macdonald in International Publication No. WO2008052322, the contents of which are herein incorporated in their entirety. Cathepsins are a family of proteases with unique mechanisms to cleave specific proteins. Cathepsin B is a cysteine protease and cathepsin D is an aspartyl protease. Matrix metalloproteinases are a family of calcium-dependent and zinc-containing endopeptidases. Legumain is an enzyme catalyzing the hydrolysis of (-Asn-Xaa-) bonds of proteins and small molecule substrates.

In certain embodiments, payload regions may encode linkers that are not cleaved. Such linkers may include a simple amino acid sequence, such as a glycine rich sequence. In some cases, linkers may include flexible peptide linkers including glycine and serine residues. The linker may include flexible peptide linkers of different lengths, e.g. nxG4S, (SEQ ID NO: 68) where n=1-10, and the length of the encoded linker varies between 5 and 50 amino acids. In a non-limiting example, the linker may be 5×G4S (SEQ ID NO: 69). These flexible linkers are small and without side chains so they tend not to influence secondary protein structure while providing a flexible linker between antibody segments (George, R. A., et al., 2002. Protein Engineering 15(11): 871-9; Huston, J. S. et al., 1988. PNAS 85:5879-83; and Shan. D. et al., 1999. Journal of Immunology. 162(11): 6589-95; the contents of each of which are herein incorporated by reference in their entirety). Furthermore, the polarity of the serine residues improves solubility and prevents aggregation problems.

In certain embodiments, payload regions of the present disclosure may encode small and unbranched serine-rich peptide linkers, such as those described by Huston et al. in U.S. Pat. No. 5,525,491, the contents of which are herein incorporated in their entirety. Polypeptides encoded by the payload region of the present disclosure, linked by serine-rich linkers, have increased solubility.

In certain embodiments, payload regions of the present disclosure may encode artificial linkers, such as those described by Whitlow and Filpula in U.S. Pat. No. 5,856,456 and Ladner et al. in U.S. Pat. No. 4,946,778, the contents of each of which are herein incorporated by their entirety.

In certain embodiments, the payload region encodes at least one G4S3 (3×G4S) linker (SEQ ID NO: 70). In certain embodiments, the payload region encodes at least one G4S linker (SEQ ID NO: 71). In certain embodiments, the payload region encodes at least one furin site. In certain embodiments, the payload region encodes at least one T2A linker. In certain embodiments, the payload region encodes at least one F2A linker. In certain embodiments, the payload region encodes at least one P2A linker. In certain embodiments, the payload region encodes at least one IRES sequence. In certain embodiments, the payload region encodes at least one G4S5 (5×G4S) linker (SEQ ID NO: 69). In certain embodiments, the payload region encodes at least one furin and one 2A linker. In certain embodiments, the payload region encodes at least one hinge region. As a non-limiting example, the hinge is a IgG hinge.

In certain embodiments, the linker region may be 1-50, 1-100, 50-100, 50-150, 100-150, 100-200, 150-200, 150-250, 200-250, 200-300, 250-300, 250-350, 300-350, 300-400, 350-400, 350-450, 400-450, 400-500, 450-500, 450-550, 500-550, 500-600, 550-600, 550-650, or 600-650 nucleotides in length. The linker region may have a length of 1-650 nucleotides (or any value or range therein) or greater than 650. In certain embodiments, the linker region may be 12 nucleotides in length. In certain embodiments, the linker region may be 18 nucleotides in length. In certain embodiments, the linker region may be 45 nucleotides in length. In certain embodiments, the linker region may be 54 nucleotides in length. In certain embodiments, the linker region may be 66 nucleotides in length. In certain embodiments, the linker region may be 75 nucleotides in length. In certain embodiments, the linker region may be 78 nucleotides in length. In certain embodiments, the linker region may be 87 nucleotides in length. In certain embodiments, the linker region may be 108 nucleotides in length. In certain embodiments, the linker region may be 153 nucleotides in length. In certain embodiments, the linker region may be 198 nucleotides in length. In certain embodiments, the linker region may be 623 nucleotides in length.

Introns

In certain embodiments, the vector genome includes at least one element to enhance the transgene target specificity and expression (See e.g., Powell et al. *Viral Expression Cassette Elements to Enhance Transgene Target Specificity and Expression in Gene Therapy,* 2015; the contents of which are herein incorporated by reference in its entirety) such as an intron. Non-limiting examples of introns include, MVM (67-97 bps), FIX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In certain embodiments, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

Stuffer Sequences

In certain embodiments, the viral genome includes at least one element to improve packaging efficiency and expression, such as a stuffer or filler sequence. Non-limiting examples of stuffer sequences include albumin and/or alpha-1 antitrypsin. Any known viral, mammalian, or plant sequence may be manipulated for use as a stuffer sequence.

In certain embodiments, the stuffer or filler sequence may be from about 100-3500 nucleotides in length. The stuffer sequence may have a length of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000.

miRNA

In certain embodiments, the viral genome includes at least one sequence encoding a miRNA to reduce the expression of the transgene in a specific tissue. miRNAs and their targeted tissues are well known in the art. As a non-limiting example, a miR-122 miRNA may be encoded in the viral genome to reduce the expression of the viral genome in the liver.

Payload

AAV particles of the present disclosure can include, or be produced using, at least one payload construct which includes at least one payload region. In certain embodiments, the payload construct includes an expression control sequence operably linked to a payload region. In certain embodiments, the payload region may be located within a viral genome, such as the viral genome of a payload construct. At the 5 and/or the 3' end of the payload region there may be at least one inverted terminal repeat (ITR). Within the payload region, there may be a promoter region, an intron region and a coding region.

In certain embodiments, a payload construct of the present disclosure can be a bacmid, also known as a baculovirus plasmid.

In certain embodiments, the payload region of the AAV particle includes one or more nucleic acid sequences encoding a polypeptide or protein of interest.

In certain embodiments, the AAV particle includes a viral genome with a payload region comprising nucleic acid sequences encoding more than one polypeptide of interest. In certain embodiments, a viral genome encoding one or more polypeptides may be replicated and packaged into a viral particle. A target cell transduced with a viral particle comprising the vector genome may express each of the one or more polypeptides in the single target cell.

Where the AAV particle payload region encodes a polypeptide, the polypeptide may be a peptide, polypeptide or protein. As a non-limiting example, the payload region may encode at least one therapeutic protein of interest. The AAV viral genomes encoding polypeptides described herein may be useful in the fields of human disease, viruses, infections veterinary applications and a variety of in vivo and in vitro settings.

In certain embodiments, administration of the formulated AAV particles (which include the viral genome) to a subject will increase the expression of a protein in a subject. In certain embodiments, the increase of the expression of the protein will reduce the effects and/or symptoms of a disease or ailment associated with the polypeptide encoded by the payload.

In certain embodiments, the AAV particle includes a viral genome with a payload region comprising a nucleic acid sequence encoding a protein of interest (i.e. a payload protein, therapeutic protein).

In certain embodiments, the payload region comprises a nucleic acid sequence encoding a protein including but not limited to an antibody, Aromatic L-Amino Acid Decarboxylase (AADC), ApoE2, Frataxin, survival motor neuron (SMN) protein, glucocermbrosidase, N-sulfoglucosamine sulfohydrolase, N-acetyl-alpha-glucosaminidase, iduronate 2-sulfatase, alpha-L-iduronidase, palmitoyl-protein thioesterase 1, tripeptidyl peptidase 1, battenin, CLN5, CLN6 (linclin), MFSD8, CLN8, aspartoacylase (ASPA), progranulin (GRN), MeCP2, beta-galactosidase (GLB1) and/or gigaxonin (GAN).

In certain embodiments, the AAV particle includes a viral genome with a payload region comprising a nucleic acid sequence encoding any of the disease-associated proteins (and fragment or variants thereof) described in any one of the following International Publications: WO2016073693, WO2017023724, WO2018232055, WO2016077687, WO2016077689, WO2018204786, WO2017201258, WO2017201248, WO2018204803, WO2018204797, WO2017189959, WO2017189963, WO2017189964, WO2015191508, WO2016094783, WO20160137949, WO2017075335; the contents of which are each herein incorporated by reference in their entirety.

Amino acid sequences encoded by payload regions of the viral genomes of the disclosure may be translated as a whole polypeptide, a plurality of polypeptides or fragments of polypeptides, which independently may be encoded by one or more nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

In certain embodiments a "polypeptide variant" is provided. The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and in certain embodiments, they will be at least about 80%, or at least about 90% identical (homologous) to a native or reference sequence.

The present disclosure comprises the use of formulated AAV particles whose vector genomes encode modulatory polynucleotides, e.g., RNA or DNA molecules as therapeutic agents. Accordingly, the present disclosure provides vector genomes which encode polynucleotides which are processed into small double stranded RNA (dsRNA) molecules (small interfering RNA, siRNA, miRNA, pre-miRNA) targeting a gene of interest. The present disclosure also provides methods of their use for inhibiting gene expression and protein production of an allele of the gene of interest, for treating diseases, disorders, and/or conditions.

In certain embodiments, the AAV particle includes a viral genome with a payload region comprising a nucleic acid sequence encoding or including one or more modulatory polynucleotides. In certain embodiments, the AAV particle includes a viral genome with a payload region comprising a nucleic acid sequence encoding a modulatory polynucleotide of interest. In certain embodiments of the present disclosure, modulatory polynucleotides, e.g., RNA or DNA molecules, are presented as therapeutic agents. RNA interference mediated gene silencing can specifically inhibit targeted gene expression.

In certain embodiments, the payload region comprises a nucleic acid sequence encoding a modulatory polynucleotide which interferes with a target gene expression and/or a target protein production. In certain embodiments, the gene expression or protein production to be inhibited/modified may include but are not limited to superoxide dismutase 1 (SOD1), chromosome 9 open reading frame 72 (C9ORF72), TAR DNA binding protein (TARDBP), ataxin-3 (ATXN3), huntingtin (HTT), amyloid precursor protein (APP), apolipoprotein E (ApoE), microtubule-associated protein tau (MAPT), alpha-synuclein (SNCA), voltage-gated sodium channel alpha subunit 9 (SCN9A), and/or voltage-gated sodium channel alpha subunit 10 (SCN10A).

In certain embodiments, the AAV particle includes a viral genome with a payload region comprising a nucleic acid sequence encoding any of the modulatory polynucleotides, RNAi molecules, siRNA molecules, dsRNA molecules, and/or RNA duplexes described in any one of the following International Publications: WO2016073693, WO2017023724, WO2018232055, WO2016077687, WO2016077689, WO2018204786, WO2017201258, WO2017201248, WO2018204803, WO2018204797, WO2017189959, WO2017189963, WO2017189964, WO2015191508, WO2016094783, WO20160137949, WO2017075335; the contents of which are each herein incorporated by reference in their entirety.

In certain embodiments, a nucleic acid sequence encoding such siRNA molecules, or a single strand of the siRNA molecules, is inserted into adeno-associated viral vectors and introduced into cells, specifically cells in the central nervous system.

AAV particles have been investigated for siRNA delivery because of several unique features. Non-limiting examples of the features include (i) the ability to infect both dividing and non-dividing cells; (ii) a broad host range for infectivity, including human cells; (iii) wild-type AAV has not been associated with any disease and has not been shown to replicate in infected cells; (iv) the lack of cell-mediated immune response against the vector and (v) the non-integrative nature in a host chromosome thereby reducing potential for long-term expression. Moreover, infection with AAV particles has minimal influence on changing the pattern of cellular gene expression (Stilwell and Samulski et al., Biotechniques, 2003, 34, 148).

In certain embodiments, the encoded siRNA duplex of the present disclosure contains an antisense strand and a sense strand hybridized together forming a duplex structure, wherein the antisense strand is complementary to the nucleic acid sequence of the targeted gene of interest, and wherein the sense strand is homologous to the nucleic acid sequence of the targeted gene of interest. In other aspects, there are 0, for 2 nucleotide overhangs at the 3'end of each strand.

The payloads of the formulated AAV particles of the present disclosure may encode one or more agents which are subject to RNA interference (RNAi) induced inhibition of gene expression. Provided herein are encoded siRNA duplexes or encoded dsRNA that target a gene of interest (referred to herein collectively as "siRNA molecules"). Such siRNA molecules, e.g., encoded siRNA duplexes, encoded dsRNA or encoded siRNA or dsRNA precursors can reduce or silence gene expression in cells, for example, astrocytes or microglia, cortical, hippocampal, entorhinal, thalamic, sensory or motor neurons.

RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2-nucleotide 3' overhangs and that match the nucleic acid sequence of the target gene. These short RNA species may be naturally produced in vivo by Dicer-mediated cleavage of larger dsRNAs and they are functional in mammalian cells.

Naturally expressed small RNA molecules, known as microRNAs (miRNAs), elicit gene silencing by regulating the expression of mRNAs. The miRNAs containing RNA Induced Silencing Complex (RISC) targets mRNAs presenting a perfect sequence complementarity with nucleotides 2-7 in the 5' region of the miRNA which is called the seed region, and other base pairs with its 3' region. miRNA mediated down regulation of gene expression may be caused by cleavage of the target mRNAs, translational inhibition of the target mRNAs, or mRNA decay. miRNA targeting sequences are usually located in the 3' UTR of the target mRNAs. A single miRNA may target more than 100 transcripts from various genes, and one mRNA may be targeted by different miRNAs.

siRNA duplexes or dsRNA targeting a specific mRNA may be designed as a payload of an AAV particle and introduced into cells for activating RNAi processes. Elbashir et al. demonstrated that 21-nucleotide siRNA duplexes (termed small interfering RNAs) were capable of effecting potent and specific gene knockdown without inducing immune response in mammalian cells (Elbashir S M et al., Nature, 2001, 411, 494-498). Since this initial report, post-transcriptional gene silencing by siRNAs quickly emerged as a powerful tool for genetic analysis in mammalian cells and has the potential to produce novel therapeutics.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases it requires higher concentration of the ss-siRNA to achieve the effective gene silencing potency of the corresponding duplex.

In certain embodiments, the siRNA molecules may be encoded in a modulatory polynucleotide which also comprises a molecular scaffold. As used herein a "molecular scaffold" is a framework or starting molecule that forms the sequence or structural basis against which to design or make a subsequent molecule.

In certain embodiments, the modulatory polynucleotide which comprises the payload (e.g., siRNA, miRNA or other RNAi agent described herein) includes molecular scaffold which comprises a leading 5' flanking sequence which may be of any length and may be derived in whole or in part from wild type microRNA sequence or be completely artificial. A 3' flanking sequence may mirror the 5' flanking sequence in size and origin. In certain embodiments, one or both of the 5' and 3' flanking sequences are absent.

In certain embodiments, the molecular scaffold may comprise one or more linkers known in the art. The linkers may separate regions or one molecular scaffold from another. As a non-limiting example, the molecular scaffold may be polycistronic.

In certain embodiments, the modulatory polynucleotide is designed using at least one of the following properties: loop variant, seed mismatch/bulge/wobble variant, stem mismatch, loop variant and basal stem mismatch variant, seed mismatch and basal stem mismatch variant, stem mismatch and basal stem mismatch variant, seed wobble and basal stem wobble variant, or a stem sequence variant.

Genome Size

In certain embodiments, the AAV particle which includes a payload described herein may be single stranded or double stranded vector genome. The size of the vector genome may be small, medium, large or the maximum size. Additionally, the vector genome may include a promoter and a polyA tail.

In certain embodiments, the vector genome which includes a payload described herein may be a small single stranded vector genome. A small single stranded vector genome may be 2.1 to 3.5 kb in size such as about 2.1, 2.2, 2.3, 2.4, 2.5, 2.6, 2.7, 2.8, 2.9, 3.0, 3.1, 3.2, 3.3, 3.4, and 3.5 kb in size. As a non-limiting example, the small single stranded vector genome may be 3.2 kb in size. As another non-limiting example, the small single stranded vector genome may be 2.2 kb in size. Additionally, the vector genome may include a promoter and a polyA tail.

In certain embodiments, the vector genome which includes a payload described herein may be a small double stranded vector genome. A small double stranded vector genome may be 1.3 to 1.7 kb in size such as about 1.3, 1.4, 1.5, 1.6, and 1.7 kb in size. As a non-limiting example, the small double stranded vector genome may be 1.6 kb in size. Additionally, the vector genome may include a promoter and a polyA tail.

In certain embodiments, the vector genome which includes a payload described herein e.g., polynucleotide, siRNA or dsRNA, may be a medium single stranded vector genome. A medium single stranded vector genome may be 3.6 to 4.3 kb in size such as about 3.6, 3.7, 3.8, 3.9, 4.0, 4.1, 4.2 and 4.3 kb in size. As a non-limiting example, the medium single stranded vector genome may be 4.0 kb in size. Additionally, the vector genome may include a promoter and a polyA tail.

In certain embodiments, the vector genome which includes a payload described herein may be a medium double stranded vector genome. A medium double stranded vector genome may be 1.8 to 2.1 kb in size such as about 1.8, 1.9, 2.0, and 2.1 kb in size. As a non-limiting example, the medium double stranded vector genome may be 2.0 kb in size. Additionally, the vector genome may include a promoter and a polyA tail.

In certain embodiments, the vector genome which includes a payload described herein may be a large single stranded vector genome. A large single stranded vector genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded vector genome may be 4.7 kb in size. As another non-limiting example, the large single stranded vector genome may be 4.8 kb in size. As yet another non-limiting example, the large single stranded vector genome may be 6.0 kb in size. Additionally, the vector genome may include a promoter and a polyA tail.

In certain embodiments, the vector genome which includes a payload described herein may be a large double stranded vector genome. A large double stranded vector genome may be 2.2 to 3.0 kb in size such as about 2.2, 2.3, 2.4, 2.5, 2.6, 2.7, 2.8, 2.9 and 3.0 kb in size. As a non-limiting example, the large double stranded vector genome may be 2.4 kb in size. Additionally, the vector genome may include a promoter and a polyA tail.

AAV Serotypes

AAV particles of the present disclosure may include or be derived from any natural or recombinant AAV serotype. According to the present disclosure, the AAV particles may utilize or be based on a serotype or include a peptide selected from any of the following: VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/rl1.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVth8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61

AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-FL, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV Clv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, AAVrh20, AAVrh32/33, AAVrh39, AAVrh46, AAVrh73, AAVrh74, AAVhu.26, or variants or derivatives thereof.

The AAV-DJ sequence may include two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may include three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In certain embodiments, the AAV may be a serotype generated by the AAV9 capsid library with mutations in amino acids 390-627 (VP1 numbering) The serotype and corresponding nucleotide and amino acid substitutions may be, but is not limited to, AAV9.1 (G1594C; D532H), AAV6.2 (T1418A and T1436X; V473D and 1479K), AAV9.3 (T1238A; F413Y), AAV9.4 (T1250C and A1617C; F417S), AAV9.5 (A1235G, A1314T, A1642G, C1760T; Q412R, T548A, A587V), AAV9.6 (T1231 A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V6061), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T5821), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T4921, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K5281), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In any of the DNA and RNA sequences referenced and/or described herein, the single letter symbol has the following description: A for adenine; C for cytosine; G for guanine; T for thymine; U for Uracil; W for weak bases such as adenine or thymine; S for strong nucleotides such as cytosine and guanine; M for amino nucleotides such as adenine and cytosine; K for keto nucleotides such as guanine and thymine; R for purines adenine and guanine; Y for pyrimidine cytosine and thymine; B for any base that is not A (e.g., cytosine, guanine, and thymine); D for any base that is not C (e.g., adenine, guanine, and thymine); H for any base that is not G (e.g., adenine, cytosine, and thymine); V for any base that is not T (e.g., adenine, cytosine, and guanine); N for any nucleotide (which is not a gap); and Z is for zero.

In any of the amino acid sequences referenced and/or described herein, the single letter symbol has the following description; G (Gly) for Glycine; A (Ala) for Alanine; L (Leu) for Leucine; M (Met) for Methionine; F (Phe) for Phenylalanine; W (Trp) for Tryptophan; K (Lys) for Lysine; Q (Gln) for Glutamine; E (Glu) for Glutamic Acid; S (Ser) for Serine; P (Pro) for Proline; V (Val) for Valine; I (Ile) for Isoleucine; C (Cys) for Cysteine; Y (Tyr) for Tyrosine; H (His) for Histidine; R (Arg) for Arginine; N (Asn) for Asparagine; D (Asp) for Aspartic Acid; T (Thr) for Threonine; B (Asx) for Aspartic acid or Asparagine; J (Xle) for Leucine or Isoleucine; O (Pyl) for Pyrrolysine; U (Sec) for Selenocysteine; X (Xaa) for any amino acid; and Z (Glx) for Glutamine or Glutamic acid.

In certain embodiments, the AAV serotype may be, or may include a sequence, insert, modification or mutation as described in Patent Publications WO2015038958, WO2017100671, WO2016134375, WO2017083722, WO2017015102, WO2017058892, WO2017066764, U.S. Pat. Nos. 9,624,274, 9,475,845, US20160369298, US20170145405, the contents of which are herein incorporated by reference in their entirety.

In certain embodiments, the AAV may be a serotype generated by Cre-recombination-based AAV targeted evolution (CREATE) as described by Deverman et al., (Nature Biotechnology 34(2):204-209 (2016)), the contents of which are herein incorporated by reference in their entirety. In certain embodiments, the AAV serotype may be as described in Jackson et al (Frontiers in Molecular Neuroscience 9:154 (2016)), the contents of which are herein incorporated by reference in their entirety.

In certain embodiments, the AAV serotype is selected for use due to its tropism for cells of the central nervous system. In certain embodiments, the cells of the central nervous system are neurons. In another embodiment, the cells of the central nervous system are astrocytes.

In certain embodiments, the AAV serotype is selected for use due to its tropism for cells of the muscle(s).

In certain embodiments, the initiation codon for translation of the AAV VP1 capsid protein may be CTG, TTG, or GTG as described in U.S. Pat. No. 8,163,543, the contents of which are herein incorporated by reference in its entirety.

The present disclosure refers to structural capsid proteins (including VP1, VP2 and VP3) which are encoded by capsid (Cap) genes. These capsid proteins form an outer protein structural shell (i.e. capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins.

Where the Met/AA-clipping is incomplete, a mixture of one or more (one, two or three) VP capsid proteins including the viral capsid may be produced, some of which may include a Met1/AA1 amino acid (Met+/AA+) and some of which may lack a Met1/AA1 amino acid as a result of Met/AA-clipping (Met-/AA-). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. *Hum Gene Ther Methods.* 2017 Oct. 28(5):255-267; Hwang, et al. N-Terminal Acetylation of Cellular Proteins Creates Specific Degradation Signals. *Science.* 2010 Feb. 19. 327(5968): 973-977; the contents of which are each incorporated herein by reference in their entirety.

According to the present disclosure, references to capsid proteins is not limited to either clipped (Met-/AA-) or unclipped (Met+/AA+) and may, in context, refer to independent capsid proteins, viral capsids included of a mixture of capsid proteins, and/or polynucleotide sequences (or fragments thereof) which encode, describe, produce or result in capsid proteins of the present disclosure. A direct reference to a "capsid protein" or "capsid polypeptide" (such as VP1, VP2 or VP2) may also include VP capsid proteins which include a Met1/AA1 amino acid (Met+/AA+) as well as corresponding VP capsid proteins which lack the Met1/AA1 amino acid as a result of Met/AA-clipping (Met-/AA-).

Further according to the present disclosure, a reference to a specific SEQ ID NO: (whether a protein or nucleic acid) which includes or encodes, respectively, one or more capsid proteins which include a Met1/AA1 amino acid (Met+/AA+) should be understood to teach the VP capsid proteins which lack the Met1/AA1 amino acid as upon review of the sequence, it is readily apparent any sequence which merely lacks the first listed amino acid (whether or not Met1/AA1).

As a non-limiting example, reference to a VP1 polypeptide sequence which is 736 amino acids in length and which includes a "Met1" amino acid (Met+) encoded by the AUG/ATG start codon may also be understood to teach a VP1 polypeptide sequence which is 735 amino acids in length and which does not include the "Met1" amino acid (Met-) of the 736 amino acid Met+sequence. As a second non-limiting example, reference to a VP1 polypeptide sequence which is 736 amino acids in length and which includes an "AA1" amino acid (AA1+) encoded by any NNN initiator codon may also be understood to teach a VP1 polypeptide sequence which is 735 amino acids in length and which does not include the "AA1" amino acid (AA1-) of the 736 amino acid AA1+ sequence.

References to viral capsids formed from VP capsid proteins (such as reference to specific AAV capsid serotypes), can incorporate VP capsid proteins which include a Met1/AA1 amino acid (Met+/AA1+), corresponding VP capsid proteins which lack the Met1/AA1 amino acid as a result of Met/AA1-clipping (Met-/AA1-), and combinations thereof (Met+/AA1+ and Met-/AA1-).

As a non-limiting example, an AAV capsid serotype can include VP1 (Met+/AA1+), VP1 (Met-/AA1-), or a combination of VP1 (Met+/AA1+) and VP1 (Met-/AA1-). An AAV capsid serotype can also include VP3 (Met+/AA1+), VP3 (Met-/AA1-), or a combination of VP3 (Met+/AA1+) and VP3 (Met-/AA1-); and can also include similar optional combinations of VP2 (Met+/AA1) and VP2 (Met-/AA1-).

Introduction into Cells

The encoded siRNA molecules (e.g., siRNA duplexes) of the present disclosure may be introduced into cells by being encoded by the vector genome of an AAV particle. These AAV particles are engineered to facilitate the entry into cells that are not readily amendable to transfection/transduction. Also, some synthetic viral vectors possess an ability to integrate the shRNA into the cell genome, thereby leading to stable siRNA expression and long-term knockdown of a target gene. In this manner, viral vectors are engineered as vehicles for specific delivery while lacking the deleterious replication and/or integration features found in wild-type virus.

In certain embodiments, the encoded siRNA molecule is introduced into a cell by transfecting, infecting or transducing the cell with an AAV particle comprising nucleic acid sequences capable of producing the siRNA molecule when transcribed in the cell. In certain embodiments, the siRNA molecule is introduced into a cell by injecting into the cell or tissue an AAV particle comprising a nucleic acid sequence capable of producing the siRNA molecule when transcribed in the cell.

In certain embodiments, prior to transfection/transduction, an AAV particle comprising a nucleic acid sequence encoding the siRNA molecules of the present disclosure may be transfected into cells.

Other methods for introducing AAV particles comprising the nucleic acid sequence for the siRNA molecules described herein may include photochemical internalization as described in U.S. Patent publication No. 20120264807; the content of which is herein incorporated by reference in its entirety.

In certain embodiments, the formulations described herein may contain at least one AAV particle comprising the nucleic acid sequence encoding the siRNA molecules described herein. In certain embodiments, the siRNA molecules may target the gene of interest at one target site. In another embodiment, the formulation comprises a plurality of AAV particles, each AAV particle comprising a nucleic acid sequence encoding a siRNA molecule targeting the gene of interest at a different target site. The gene of interest may be targeted at 2, 3, 4, 5 or more than 5 sites.

In certain embodiments, the AAV particles from any relevant species, such as, but not limited to, human, pig, dog, mouse, rat or monkey may be introduced into cells.

In certain embodiments, the formulated AAV particles may be introduced into cells or tissues which are relevant to the disease to be treated.

In certain embodiments, the formulated AAV particles may be introduced into cells which have a high level of endogenous expression of the target sequence.

In another embodiment, the formulated AAV particles may be introduced into cells which have a low level of endogenous expression of the target sequence.

In certain embodiments, the cells may be those which have a high efficiency of AAV transduction.

In certain embodiments, formulated AAV particles comprising a nucleic acid sequence encoding the siRNA molecules of the present disclosure may be used to deliver siRNA molecules to the central nervous system (e.g., U.S. Pat. No. 6,180,613; the contents of which is herein incorporated by reference in its entirety).

In some aspects, the formulated AAV particles comprising a nucleic acid sequence encoding the siRNA molecules of the present disclosure may further comprise a modified capsid including peptides from non-viral origin. In other aspects, the AAV particle may contain a CNS specific chimeric capsid to facilitate the delivery of encoded siRNA duplexes into the brain and the spinal cord. For example, an alignment of cap nucleotide sequences from AAV variants exhibiting CNS tropism may be constructed to identify variable region (VR) sequence and structure.

In certain embodiments, the formulated AAV particle comprising a nucleic acid sequence encoding the siRNA molecules of the present disclosure may encode siRNA molecules which are polycistronic molecules. The siRNA molecules may additionally comprise one or more linkers between regions of the siRNA molecules.

In certain embodiments, a formulated AAV particle may comprise at least one of the modulatory polynucleotides encoding at least one of the siRNA sequences or duplexes described herein.

In certain embodiments, an expression vector may comprise, from ITR to ITR recited 5' to 3', an ITR, a promoter, an intron, a modulatory polynucleotide, a polyA sequence and an ITR.

In certain embodiments, the encoded siRNA molecule may be located downstream of a promoter in an expression vector such as, but not limited to, CMV, U6, H1, CBA or a CBA promoter with a SV40 intron. Further, the encoded siRNA molecule may also be located upstream of the polyadenylation sequence in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In certain embodiments, the encoded siRNA molecule may be located upstream of the polyadenylation sequence in an expression vector. Further, the encoded siRNA molecule may be located downstream of a promoter such as, but not limited to, CMV, U6, CBA or a CBA promoter with a SV40 intron in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In certain embodiments, the encoded siRNA molecule may be located in a scAAV.

In certain embodiments, the encoded siRNA molecule may be located in an ssAAV.

In certain embodiments, the encoded siRNA molecule may be located near the 5' end of the flip ITR in an expression vector. In another embodiment, the encoded siRNA molecule may be located near the 3' end of the flip ITR in an expression vector. In yet another embodiment, the encoded siRNA molecule may be located near the 5' end of the flop ITR in an expression vector. In yet another embodiment, the encoded siRNA molecule may be located near the 3' end of the flop ITR in an expression vector. In certain embodiments, the encoded siRNA molecule may be located between the 5' end of the flip ITR and the 3' end of the flop ITR in an expression vector. In certain embodiments, the encoded siRNA molecule may be located between (e.g., half-way between the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the encoded siRNA molecule may be located with the first 1-5%, 1-10%, 1-15%, 1-20%, 1-25%, 5-10%, 5-15, 5-20%, 5-25%, 10-15%, 10-20%, 10-25%, 15-20%, 15-25%, or 20-25% downstream from the 5' or 3' end of an ITR (e.g., Flip or Flop ITR) in an expression vector.

In certain embodiments, AAV particle comprising the nucleic acid sequence for the siRNA molecules of the present disclosure may be formulated for CNS delivery. Agents that cross the brain blood barrier may be used. For example, some cell penetrating peptides that can target siRNA molecules to the brain blood barrier endothelium may be used to formulate the siRNA duplexes targeting the gene of interest.

In certain embodiments, the formulated AAV particle comprising a nucleic acid sequence encoding the siRNA molecules of the present disclosure may be administered directly to the CNS. As a non-limiting example, the vector comprises a nucleic acid sequence encoding the siRNA molecules targeting the gene of interest.

In specific embodiments, compositions of formulated AAV particles comprising a nucleic acid sequence encoding the siRNA molecules of the present disclosure may be administered in a way which facilitates the vectors or siRNA molecule to enter the central nervous system and penetrate into motor neurons.

In certain embodiments, the formulated AAV particle may be administered to a subject (e.g., to the CNS of a subject via intrathecal administration) in a therapeutically effective amount for the siRNA duplexes or dsRNA to target the motor neurons and astrocytes in the spinal cord and/or brain stem. As a non-limiting example, the siRNA duplexes or dsRNA may reduce the expression of a protein or mRNA.

II. AAV Production

General Viral Production Process

Viral production cells for the production of rAAV particles generally include mammalian cell types. However, mammalian cells present several complications to the large-scale production of rAAV particles, including general low yield of viral-particles-per-replication-cell as well as high risks for undesirable contamination from other mammalian biomaterials in the viral production cell. As a result, insect cells have become an alternative vehicle for large-scale production of rAAV particles.

AAV production systems using insect cells also present a range of complications. For example, high-yield production of rAAV particles often requires a lower expression of Rep78 compared to Rep52. Controlling the relative expression of Rep78 and Rep52 in insect cells thus requires carefully designed control mechanisms within the Rep operon. These control mechanisms can include individually engineered insect cell promoters, such as ΔIE1 promoters for Rep78 and PolH promoters for Rep52, or the division of the Rep-encoding nucleotide sequences onto independently engineered sequences or constructs. However, implementation of these control mechanisms often leads to reduced rAAV particle yield or to structurally unstable virions.

In another example, production of rAAV particles requires VP1, VP2 and VP3 proteins which assemble to form the AAV capsid. High-yield production of rAAV particles requires adjusted ratios of VP1, VP2 and VP3, which should generally be around 1:1:10, respectively, but can vary from 1-2 for VP1 and/or 1-2 for VP2, relative to 10 VP3 copies. This ratio is important for the quality of the capsid, as too much VP1 destabilizes the capsid and too little VP1 will decrease the infectivity of the virus.

Wild type AAV use a deficient splicing method to control VP1 expression; a weak start codon (ACG) with special surrounding ("Kozak" sequence) to control VP2; and a standard start codon (ATG) for VP3 expression. However, in some baculovirus systems, the mammalian splicing sequences are not always recognized and unable to properly control the production of VP1, VP2 and VP3. Consequently, neighboring nucleotides and the ACG start sequence from VP2 can be used to drive capsid protein production. Unfortunately, for most of the AAV serotypes, this method creates a capsid with a lower ratio of VP1 compared to VP2 (<1 relative to 10 VP3 copies). To more effectively control the production of VP proteins, non-canonical or start codons have been used, like TTG, GTG or CTG. However, these start codons are considered suboptimal by those in the art relative to the wild type ATG or ACG start codons (See, WO2007046703 and WO2007148971, the contents of which are incorporated herein by reference in their entirety).

In another example, production of rAAV particles using a baculovirus/Sf9 system generally requires the widely used bacmid-based Baculovirus Expression Vector System (BEVs), which are not optimized for large-scale AAV production. Aberrant proteolytic degradation of viral proteins in the bacmid-based BEVs is an unexpected issue, precluding the reliable large-scale production of AAV capsid proteins using the baculovirus/Sf9 system.

There is continued need for methods and systems which allow for effective and efficient large scale (commercial) production of rAAV particles in mammalian and insect cells.

The details of one or more embodiments of the present disclosure are set forth in the accompanying description below. Other features, objects, and advantages of the present disclosure will be apparent from the description, drawings, and the claims. In the description, the singular forms also include the plural unless the context clearly dictates otherwise. Unless defined otherwise, all technical and scientific terms used herein have the same meaning as commonly understood by one of ordinary skill in the art to which this present disclosure belongs. In the case of conflict with disclosures incorporated by reference, the present express description will control.

In certain embodiments, the constructs, polynucleotides, polypeptides, vectors, serotypes, capsids formulations, or particles of the present disclosure may be, may include, may be modified by, may be used by, may be used for, may be used with, or may be produced with any sequence, element, construct, system, target or process described in one of the following International Publications: WO2016073693, WO2017023724, WO2018232055, WO2016077687, WO2016077689, WO2018204786, WO2017201258, WO2017201248, WO2018204803, WO2018204797, WO2017189959, WO2017189963, WO2017189964, WO2015191508, WO2016094783, WO20160137949, WO2017075335; the contents of which are each herein incorporated by reference in their entirety.

AAV production of the present disclosure includes processes and methods for producing AAV particles and viral vectors which can contact a target cell to deliver a payload, e.g. a recombinant viral construct, which includes a nucleotide encoding a payload molecule. In certain embodiments, the viral vectors are adeno-associated viral (AAV) vectors such as recombinant adeno-associated viral (rAAV) vectors. In certain embodiments, the AAV particles are adeno-associated viral (AAV) particles such as recombinant adeno-associated viral (rAAV) particles.

The present disclosure provides methods of producing AAV particles or viral vectors by (a) contacting a viral production cell with one or more viral expression constructs encoding at least one chimeric capsid protein, and one or more payload construct vectors, wherein said payload construct vector includes a payload construct encoding a payload molecule selected from the group consisting of a transgene, a polynucleotide encoding protein, and a modulatory nucleic acid; (b) culturing said viral production cell under conditions such that at least one AAV particle or viral vector is produced, and (c) isolating said at least one AAV particle or viral vector.

In these methods a viral expression construct may encode at least one structural protein and/or at least one non-structural protein. The structural protein may include any of the native or wild type capsid proteins VP1, VP2 and/or VP3 or a chimeric protein. The non-structural protein may include any of the native or wild type Rep78, Rep68, Rep52 and/or Rep40 proteins or a chimeric protein.

In certain embodiments, contacting occurs via transient transfection, viral transduction and/or electroporation.

In certain embodiments, the viral production cell is selected from the group consisting of a mammalian cell and an insect cell. In certain embodiments, the insect cell includes a *Spodoptera frugiperda* insect cell. In certain embodiments, the insect cell includes a Sf9 insect cell. In certain embodiments, the insect cell includes a Sf21 insect cell.

The payload construct vector of the present disclosure may include at least one inverted terminal repeat (ITR) and may include mammalian DNA.

Also provided are AAV particles and viral vectors produced according to the methods described herein.

The AAV particles of the present disclosure may be formulated as a pharmaceutical composition with one or more acceptable excipients.

In certain embodiments, an AAV particle or viral vector may be produced by a method described herein.

In certain embodiments, the AAV particles may be produced by contacting a viral production cell (e.g., an insect cell or a mammalian cell) with at least one viral expression construct encoding at least one capsid protein and at least one payload construct vector. The viral production cell may be contacted by transient transfection, viral transduction and/or electroporation. The payload construct vector may include a payload construct encoding a payload molecule such as, but not limited to, a transgene, a polynucleotide encoding protein, and a modulatory nucleic acid. The viral production cell can be cultured under conditions such that at least one AAV particle or viral vector is produced, isolated (e.g., using temperature-induced lysis, mechanical lysis and/or chemical lysis) and/or purified (e.g., using filtration, chromatography and/or immunoaffinity purification). As a non-limiting example, the payload construct vector may include mammalian DNA.

In certain embodiments, the AAV particles are produced in an insect cell (e.g., *Spodoptera frugiperda* (Sf9) cell) using the method described herein. As a non-limiting example, the insect cell is contacted using viral transduction which may include baculoviral transduction.

In another embodiment, the AAV particles are produced in a mammalian cell using the method described herein. As a non-limiting example, the mammalian cell is contacted using transient transfection.

In certain embodiments, the viral expression construct may encode at least one structural protein and at least one non-structural protein. As a non-limiting example, the structural protein includes VP1, VP2 and/or VP3. As another non-limiting example, the non-structural protein includes Rep78, Rep68, Rep52 and/or Rep40.

In certain embodiments, the AAV particle production method described herein produces greater than $10^1$, greater than $10^2$, greater than $10^3$, greater than $10^4$ or greater than $10^5$ AAV particles in a viral production cell.

In certain embodiments, a process of the present disclosure includes production of viral particles in a viral production cell using a viral production system which includes at least one viral expression construct and at least one payload construct. The at least one viral expression construct and at least one payload construct can be co-transfected (e.g. dual transfection, triple transfection) into a viral production cell. The transfection is completed using standard molecular biology techniques known and routinely performed by a person skilled in the art. The viral production cell provides the cellular machinery necessary for expression of the proteins and other biomaterials necessary for producing the AAV particles, including Rep proteins which replicate the payload construct and Cap proteins which assemble to form a capsid that encloses the replicated payload constructs. The resulting AAV particle is extracted from the viral production cells and processed into a pharmaceutical preparation for administration.

Once administered, the AAV particles contacts a target cell and enters the cell in an endosome. The AAV particle releases from the endosome and subsequently contacts the nucleus of the target cell to deliver the payload construct. The payload construct, e.g. recombinant viral construct, is delivered to the nucleus of the target cell wherein the payload molecule encoded by the payload construct may be expressed.

In certain embodiments, the process for production of viral particles utilizes seed cultures of viral production cells that include one or more baculoviruses (e.g., a Baculoviral Expression Vector (BEV) or a baculovirus infected insect cell (BIIC) that has been transfected with a viral expression construct and a payload construct vector). In certain embodiments, the seed cultures are harvested, divided into aliquots and frozen, and may be used at a later time point to initiate an infection of a naïve population of production cells.

Large scale production of AAV particles may utilize a bioreactor. The use of a bioreactor allows for the precise measurement and/or control of variables that support the growth and activity of viral production cells such as mass, temperature, mixing conditions (impellor RPM or wave oscillation). $CO_2$ concentration, $O_2$ concentration, gas sparge rates and volumes, gas overlay rates and volumes, pH, Viable Cell Density (VCD), cell viability, cell diameter, and/or optical density (OD). In certain embodiments, the bioreactor is used for batch production in which the entire culture is harvested at an experimentally determined time point and AAV particles are purified. In another embodiment, the bioreactor is used for continuous production in which a portion of the culture is harvested at an experimentally determined time point for purification of AAV particles, and the remaining culture in the bioreactor is refreshed with additional growth media components.

AAV viral particles can be extracted from viral production cells in a process which includes cell lysis, clarification, sterilization and purification. Cell lysis includes any process that disrupts the structure of the viral production cell, thereby releasing AAV particles. In certain embodiments cell lysis may include thermal shock, chemical, or mechanical lysis methods. Clarification can include the gross purification of the mixture of lysed cells, media components, and AAV particles. In certain embodiments, clarification includes centrifugation and/or filtration, including but not limited to depth end, tangential flow, and/or hollow fiber filtration.

The end result of viral production is a purified collection of AAV particles which include two components: (1) a payload construct (e.g. a recombinant viral genome construct) and (2) a viral capsid.

In certain embodiments, a viral production system or process of the present disclosure includes steps for producing baculovirus infected insect cells (BIICs) using Viral Production Cells (VPC) and plasmid constructs. Viral Production Cells (VPCs) from a Cell Bank (CB) are thawed and expanded to provide a target working volume and VPC concentration. The resulting pool of VPCs is split into a Rep/Cap VPC pool and a Payload VPC pool. One or more Rep/Cap plasmid constructs (viral expression constructs) are processed into Rep/Cap Bacmid polynucleotides and transfected into the Rep/Cap VPC pool. One or more Payload plasmid constructs (payload constructs) are processed into Payload Bacmid polynucleotides and transfected into the Payload VPC pool. The two VPC pools are incubated to produce P1 Rep/Cap Baculoviral Expression Vectors (BEVs) and P1 Payload BEVs. The two BEV pools are expanded into a collection of Plaques, with a single Plaque being selected for Clonal Plaque (CP) Purification (also referred to as Single Plaque Expansion). The process can include a single CP Purification step or can include multiple CP Purification steps either in series or separated by other processing steps. The one-or-more CP Purification steps provide a CP Rep/Cap BEV pool and a CP Payload BEV pool. These two BEV pools can then be stored and used for future production steps, or they can be then transfected into VPCs to produce a Rep/Cap BIIC pool and a Payload BIIC pool.

In certain embodiments, a viral production system or process of the present disclosure includes steps for producing AAV particles using Viral Production Cells (VPC) and baculovirus infected insect cells (BIICs). Viral Production Cells (VPCs) from a Cell Bank (CB) are thawed and expanded to provide a target working volume and VPC concentration. The working volume of Viral Production Cells is seeded into a Production Bioreactor and can be further expanded to a working volume of 200-2000 L with a target VPC concentration for BIIC infection. The working volume of VPCs in the Production Bioreactor is then co-infected with Rep/Cap BIICs and Payload BIICs, with a target VPC:BIIC ratio and a target BIIC:BIIC ratio. VCD infection can also utilize BEVs. The co-infected VPCs are incubated and expanded in the Production Bioreactor to produce a bulk harvest of AAV particles and VPCs.

Viral Expression Construct

The viral production system of the present disclosure includes one or more viral expression constructs which can be transfected/transduced into a viral production cell. In certain embodiments, the viral expression includes a protein-coding nucleotide sequence and at least one expression control sequence for expression in a viral production cell. In certain embodiments, the viral expression includes a protein-coding nucleotide sequence operably linked to least one expression control sequence for expression in a viral production cell. In certain embodiments, the viral expression construct contains parvoviral genes under control of one or more promoters. Parvoviral genes can include nucleotide sequences encoding non-structural AAV replication proteins, such as Rep genes which encode Rep52, Rep40, Rep68 or Rep78 proteins. Parvoviral genes can include nucleotide sequences encoding structural AAV proteins, such as Cap genes which encode VP1, VP2 and VP3 proteins.

In certain embodiments, a viral expression construct can include a Rep52-coding region; a Rep52-coding region is a nucleotide sequence which includes a Rep52 nucleotide sequence encoding a Rep52 protein. In certain embodiments, a viral expression construct can include a Rep78-coding region; a Rep78-coding region is a nucleotide sequence which includes a Rep78 nucleotide sequence encoding a Rep78 protein. In certain embodiments, a viral expression construct can include a Rep40-coding region; a Rep40-coding region is a nucleotide sequence which includes a Rep40 nucleotide sequence encoding a Rep40 protein. In certain embodiments, a viral expression construct can include a Rep68-coding region; a Rep68-coding region is a nucleotide sequence which includes a Rep68 nucleotide sequence encoding a Rep68 protein.

In certain embodiments, a viral expression construct can include a VP-coding region; a VP-coding region is a nucleotide sequence which includes a VP nucleotide sequence encoding VP1, VP2, VP3, or a combination thereof. In certain embodiments, a viral expression construct can include a VP1-coding region; a VP1-coding region is a nucleotide sequence which includes a VP1 nucleotide sequence encoding a VP1 protein. In certain embodiments, a viral expression construct can include a VP2-coding region; a VP2-coding region is a nucleotide sequence which includes a VP2 nucleotide sequence encoding a VP2 protein. In certain embodiments, a viral expression construct can include a VP3-coding region; a VP3-coding region is a nucleotide sequence which includes a VP3 nucleotide sequence encoding a VP3 protein.

Structural VP proteins, VP1, VP2, and VP3, and non-structural proteins, Rep52 and Rep78, of the viral expression construct can be encoded in a single open reading frame regulated by utilization of both alternative splice acceptor and non-canonical translational initiation codons. Both Rep78 and Rep52 can be translated from a single transcript: Rep78 translation initiates at a first start codon (AUG or non-AUG) and Rep52 translation initiates from a Rep52 start codon (e.g. AUG) within the Rep78 sequence. Rep78 and Rep52 can also be translated from separate transcripts with independent start codons. The Rep52 initiation codons within the Rep78 sequence can be mutated, modified or removed, such that processing of the modified Rep78 sequence will not produce Rep52 proteins.

VP1, VP2 and VP3 can be transcribed and translated from a single transcript wherein both in-frame and out-of-frame ATG triplets preventing translation initiation at a position between the VP1 and VP2 start codons are eliminated. In certain embodiments, VP1 can be transcribed and translated independently from VP2 and VP3 from a transcript which encodes only for VP1, and not for VP2 or VP3. As use herein, the terms "encodes only for VP1" or "encodes for VP1, but not VP2 or VP3" refer to a nucleotide sequence or transcript which encodes for a VP1 capsid protein and which lacks the necessary codons within the VP1 sequence (deleted or mutated) for transcription or translation of VP2 and VP3 from the same sequence, or which includes additional codons within the VP1 sequence which prevent transcription or translation of VP2 and VP3 from the same sequence.

The viral production system of the present disclosure is not limited by the viral expression vector used to introduce the parvoviral functions into the virus replication cell. The presence of the viral expression construct in the virus replication cell need not be permanent. The viral expression constructs can be introduced by any means known, for example by chemical treatment of the cells, electroporation, or infection.

Viral expression constructs of the present disclosure may include any compound or formulation, biological or chemical, which facilitates transformation, transfection, or transduction of a cell with a nucleic acid. Exemplary biological viral expression constructs include plasmids, linear nucleic acid molecules, and recombinant viruses including baculovirus. Exemplary chemical vectors include lipid complexes. Viral expression constructs are used to incorporate nucleic acid sequences into virus replication cells in accordance with the present disclosure. (O'Reilly, David R, Lois K. Miller, and Verne A. Luckow. Baculovirus expression vectors: a laboratory manual. Oxford University Press, 1994); Maniatis et al., eds. Molecular Cloning. CSH Laboratory, NY, N.Y. (1982); and Philiport and Scluber, eds. Liposomes as tools in Basic Research and Industry. CRC Press, Ann Arbor, Mich. (1995), the contents of each of which are herein incorporated by reference in its entirety.

In certain embodiments, the viral expression construct is an AAV expression construct which includes one or more nucleotide sequences encoding non-structural AAV replication proteins, structural AAV capsid proteins, or a combination thereof.

In certain embodiments, the viral expression construct of the present disclosure may be a plasmid vector. In certain embodiments, the viral expression construct of the present disclosure may be a baculoviral construct.

The present disclosure is not limited by the number of viral expression constructs employed to produce AAV particles or viral vectors. In certain embodiments, one, two, three, four, five, six, or more viral expression constructs can be employed to produce AAV particles in viral production cells in accordance with the present disclosure. In one non-limiting example, five expression constructs may individually encode AAV VP1, AAV VP2, AAV VP3, Rep52, Rep78, and with an accompanying payload construct comprising a payload polynucleotide and at least one AAV ITR. In another embodiment, expression constructs may be employed to express, for example, Rep52 and Rep40, or Rep78 and Rep 68. Expression constructs may include any combination of VP1, VP2, VP3, Rep52/Rep40, and Rcp78/Rep68 coding sequences.

In certain embodiments of the present disclosure, a viral expression construct may be used for the production of an AAV particles in insect cells. In certain embodiments, modifications may be made to the wild type AAV sequences of the capsid and/or rep genes, for example to improve attributes of the viral particle, such as increased infectivity or specificity, or to enhance production yields.

In certain embodiments, the viral expression construct can include one or more expression control sequence between protein-coding nucleotide sequences. In certain embodiments, an expression control region can include an IRES sequence region which includes an IRES nucleotide sequence encoding an internal ribosome entry sight (IRES). The internal ribosome entry sight (IRES) can be selected from the group consisting or: FMDV-IRES from Foot-and-Mouth-Disease virus, EMCV-IRES from Encephalomyocarditis virus, and combinations thereof.

In certain embodiments, an expression control region can include a 2A sequence region which comprises a 2A nucleotide sequence encoding a viral 2A peptide. A viral 2A sequence is a relatively short (approximately 20 amino acids) sequence which contains a consensus sequence of: Asp-Val/Ile-Glu-X-Asn-Pro-Gly-Pro (SEQ ID NO: 72). The sequence allows for co-translation of multiple polypeptides within a single open reading frame (ORF). As the ORF is translated, glycine and proline residues with the 2A sequence prevent the formation of a normal peptide bond, which results in ribosomal "skipping" and "self-cleavage" within the polypeptide chain. The viral 2A peptide can be selected from the group consisting of: F2A from Foot-and-Mouth-Disease virus, T2A from *Thosea asigna* virus, E2A from Equine rhinitis A virus, P2A from porcine teschovirus-1, BmCPV2A from cytoplasmic polyhedrosis virus, BmIFV 2A from *B. mori* flacherie virus, and combinations thereof.

In certain embodiments, the viral expression construct may contain a nucleotide sequence which includes start codon region, such as a sequence encoding AAV capsid proteins which include one or more start codon regions. In certain embodiments, the start codon region can be within an expression control sequence. The start codon can be ATG or a non-ATG codon (i.e., a suboptimal start codon where the start codon of the AAV VP1 capsid protein is a non-ATG).

In certain embodiments, the viral expression construct used for AAV production may contain a nucleotide sequence encoding the AAV capsid proteins where the initiation codon of the AAV VP1 capsid protein is a non-ATG, i.e., a suboptimal initiation codon, allowing the expression of a modified ratio of the viral capsid proteins in the production system, to provide improved infectivity of the host cell. In a non-limiting example, a viral construct vector may contain a nucleic acid construct comprising a nucleotide sequence encoding AAV VP1, VP2, and VP3 capsid proteins, wherein the initiation codon for translation of the AAV VP1 capsid protein is CTG, TTG, or GTG, as described in U.S. Pat. No. 8,163,543, the contents of which are herein incorporated by reference in its entirety.

In certain embodiments, the viral expression construct of the present disclosure may be a plasmid vector or a baculoviral construct that encodes the parvoviral rep proteins for expression in insect cells. In certain embodiments, a single coding sequence is used for the Rep78 and Rep52 proteins, wherein start codon for translation of the Rep78 protein is a suboptimal start codon, selected from the group consisting of ACG, TTG, CTG and GTG, that effects partial exon skipping upon expression in insect cells, as described in U.S. Pat. No. 8,512,981, the contents of which are herein incorporated by reference in their entirety, for example to promote less abundant expression of Rep78 as compared to Rep52, which may in that it promotes high vector yields.

In certain embodiments, the viral expression construct may be a plasmid vector or a baculoviral construct for the expression in insect cells that contains repeating codons with differential codon biases, for example to achieve improved ratios of Rep proteins, e.g. Rep78 and Rep52 thereby improving large scale (commercial) production of viral expression construct and/or payload construct vectors in insect cells, as taught in U.S. Pat. No. 8,697,417, the contents of which are herein incorporated by reference in their entirety.

In another embodiment, improved ratios of rep proteins may be achieved using the method and constructs described in U.S. Pat. No. 8,642,314, the contents of which are herein incorporated by reference in their entirety.

In certain embodiments, the viral expression construct may encode mutant parvoviral Rep polypeptides which have one or more improved properties as compared with their corresponding wild type Rep polypeptide, such as the preparation of higher virus titers for large scale production. Alternatively, they may be able to allow the production of better-quality viral particles or sustain more stable production of virus. In a non-limiting example, the viral expression construct may encode mutant Rep polypeptides with a mutated nuclear localization sequence or zinc finger domain, as described in Patent Application US 20130023034, the contents of which are herein incorporated by reference in their entirety.

In certain embodiments, the viral expression construct may encode the components of a Parvoviral capsid with incorporated Gly-Ala repeat region, which may function as an immune invasion sequence, as described in US Patent Application 20110171262, the contents of which are herein incorporated by reference in its entirety.

In certain embodiments of the present disclosure, a viral expression construct may be used for the production of AAV particles in insect cells. In certain embodiments, modifications may be made to the wild type AAV sequences of the capsid and/or rep genes, for example to improve attributes of the viral particle, such as increased infectivity or specificity, or to enhance production yields.

In certain embodiments, a VP-coding region encodes one or more AAV capsid proteins of a specific AAV serotype. The AAV serotypes for VP-coding regions can be the same or different. In certain embodiments, a VP-coding region can be codon optimized. In certain embodiments, a VP-coding region or nucleotide sequence can be codon optimized for a mammal cell. In certain embodiments, a VP-coding region or nucleotide sequence can be codon optimized for an insect cell. In certain embodiments, a VP-coding region or nucleotide sequence can be codon optimized for a *Spodoptera frugiperda* cell. In certain embodiments, a VP-coding region or nucleotide sequence can be codon optimized for Sf9 or Sf21 cell lines.

In certain embodiments, a nucleotide sequence encoding one or more VP capsid proteins can be codon optimized to have a nucleotide homology with the reference nucleotide sequence of less than 100%. In certain embodiments, the nucleotide homology between the codon-optimized VP nucleotide sequence and the reference VP nucleotide sequence is less than 100%, less than 99%, less than 98%, less than 97%, less than 96%, less than 95%, less than 94%, less than 93%, less than 92%, less than 91%, less than 90%, less than 89%, less than 88%, less than 87%, less than 86%, less than 85%, less than 84%, less than 83%, less than 82%, less than 81%, less than 80%, less than 78%, less than 76%, less than 74%, less than 72%, less than 70%, less than 68%, less than 66%, less than 64%, less than 62%, less than 60%, less than 55%, less than 50%, and less than 40%.

In certain embodiments, viral expression constructs may be used that are taught in U.S. Pat. Nos. 8,512,981, 8,163,543, 8,697,417, 8,642,314, US Patent Publication Nos. US20130296532, US20110119777, US20110136227, US20110171262, US20130023034, International Patent Application Nos. PCT/NL2008/050613, PCT/NL2009/050076, PCT/NL2009/050352, PCT/NL2011/050170, PCT/NL2012/050619 and U.S. patent application Ser. No. 14/149,953, the contents of each of which are herein incorporated by reference in their entirety.

In certain embodiments, the viral expression construct of the present disclosure may be derived from viral expression constructs taught in U.S. Pat. Nos. 6,468,524, 6,984,517, 7,479,554, 6,855,314, 7,271,002, 6,723,551, US Patent Publication No. 20140107186, U.S. patent application Ser. Nos. 09/717,789, 11/936,394, 14/004,379, European Patent Application EP1082413, EP2500434, EP 2683829, EP1572893 and International Patent Application PCT/US99/11958, PCT/US01/09123, PCT/EP2012/054303, and PCT/US2002/035829 the contents of each of which are herein incorporated by reference in its entirety.

In certain embodiments, the viral expression construct may include sequences from Simian species. In certain embodiments, the viral expression construct may contain sequences, including but not limited to capsid and rep sequences from International Patent Applications PCT/US1997/015694, PCT/US2000/033256, PCT/US2002/019735, PCT/US2002/033645, PCT/US2008/013067, PCT/US2008/013066, PCT/US2008/013065, PCT/US2009/062548, PCT/US2009/001344, PCT/US2010/036332, PCT/US2011/061632, PCT/US2013/041565, U.S. application Ser. Nos. 13/475,535, 13/896,722, 10/739,096, 14/073,979, US Patent Publication Nos. US20010049144, US20120093853, US20090215871, US20040136963, US20080219954, US20040171807, US20120093778, US20080090281, US20050069866, US20100260799, US20100247490, US20140044680, US20100254947, US20110223135, US20130309205, US20120189582, US20130004461, US20130315871, U.S. Pat. Nos. 6,083,716, 7,838,277, 7,344,872, 8,603,459, 8,105,574, 7,247,472, 8,231,880, 8,524,219, 8,470,310, European Patent Application Nos. EP2301582, EP2286841, EP1944043, EP1453543, EP1409748, EP2463362, EP2220217, EP2220241, EP2220242, EP2350269, EP2250255, EP2435559, EP2643465, EP1409748, EP2325298, EP1240345, the contents of each of which is herein incorporated by reference in its entirety.

In certain embodiments, viral expression constructs of the present disclosure may include one or more nucleotide sequence from one or more viral construct described in in International Application No. PCT/US2002/025096, PCT/US2002/033629, PCT/US2003/012405, U.S. application Ser. Nos. 10/291,583, 10/420,284, U.S. Pat. No. 7,319,002, US Patent Publication No. US20040191762, US20130045186, US20110263027, US20110151434, US20030138772, US20030207259, European Application No. EP2338900, EP1456419, EP1310571, EP1359217, EP1427835, EP2338900, EP1456419, EP1310571, EP1359217 and U.S. Pat. Nos. 7,235,393 and 8,524,446.

In certain embodiments, the viral expression constructs of the present disclosure may include sequences or compositions described in International Patent Application No. PCT/US1999/025694, PCT/US1999/010096, PCT/US2001/013000, PCT/US2002/25976, PCT/US2002/033631, PCT/

US2002/033630, PCT/US2009/041606, PCT/US2012/025550, U.S. Pat. Nos. 8,637,255, 8,637,255, 7,186,552, 7,105,345, 6,759,237, 7,056,502, 7,198,951, 8,318,480, 7,790,449, 7,282,199, US Patent Publication No. US20130059289, US20040057933, US20040057932, US20100278791, US20080050345, US20080050343, US20080008684, US20060204479, US20040057931, US20040052764, US20030013189, US20090227030, US20080075740, US20080075737, US20030228282, US20130323226, US20050014262, U.S. application Ser. Nos. 14/136,331, 09/076,369, 10/738,609, European Application No. EP2573170, EP1127150, EP2341068, EP1845163, EP1127150, EP1078096, EP1285078, EP1463805, EP2010178940, US20140004143, EP2359869, EP1453547, EP2341068, and EP2675902, the contents of each of which are herein incorporated by reference in their entirety.

In certain embodiments, viral expression construct of the present disclosure may include one or more nucleotide sequence from one or more of those described in U.S. Pat. Nos. 7,186,552, 7,105,345, 6,759,237, 7,056,502, 7,198,951, 8,318,480, 7,790,449, 7,282,199, US Patent Publication No. US20130059289, US20040057933, US20040057932, US20100278791, US20080050345, US20080050343, US20080008684, US20060204479, US20040057931, US20140004143, US20090227030, US20080075740, US20080075737, US20030228282, US20040052764, US20030013189, US20050014262, US20130323226, U.S. patent application Ser. Nos. 14/136, 331, 10/738,609, European Patent Application Nos. EP1127150, EP2341068, EP1845163, EP1127150, EP1078096, EP1285078, EP2573170, EP1463805, EP2675902, EP2359869, EP1453547, EP2341068, the contents of each of which are incorporated herein by reference in their entirety.

In certain embodiments, the viral expression constructs of the present disclosure may include constructs of modified AAVs, as described in International Patent Application No. PCT/US1995/014018, PCT/US2000/026449, PCT/US2004/028817, PCT/US2006/013375, PCT/US2007/010056, PCT/US2010/032158, PCT/US2010/050135, PCT/US2011/033596, U.S. patent application Ser. Nos. 12/473,917, 08/331,384, 09/670,277, U.S. Pat. Nos. 5,871,982, 5,856, 152, 6,251,677, 6,387,368, 6,399,385, 7,906,111, European Patent Application No. EP2000103600, European Patent Publication No. EP797678, EP1046711, EP1668143, EP2359866, EP2359865, EP2357010, EP1046711, EP1218035, EP2345731, EP2298926, EP2292780, EP2292779, EP1668143, US20090197338, EP2383346, EP2359867, EP2359866, EP2359865, EP2357010, EP1866422, US20090317417, EP2016174, US Patent Publication Nos. US20110236353, US20070036760, US20100186103, US20120137379, and US20130281516, the contents of each of which are herein incorporated by reference in their entirety.

In certain embodiments, the viral expression constructs of the present disclosure may include one or more constructs described in International Application Nos. PCT/US1999/004367, PCT/US2004/010965, PCT/US2005/014556, PCT/US2006/009699, PCT/US2010/032943, PCT/US2011/033628, PCT/US2011/033616, PCT/US2012/034355, U.S. Pat. No. 8,394,386, EP1742668, US Patent Publication Nos. US20080241189, US20120046349, US20130195801, US20140031418, EP2425000, US20130101558, EP1742668, EP2561075, EP2561073, EP2699688, the contents of each of which is herein incorporated by reference in its entirety.

Expression Control
Expression Control Regions

The viral expression constructs of the present disclosure can include one or more expression control regions encoded by expression control sequences. In certain embodiments, the expression control sequences are for expression in a viral production cell, such as an insect cell. In certain embodiments, the expression control sequences are operably linked to a protein-coding nucleotide sequence. In certain embodiments, the expression control sequences are operably linked to a VP coding nucleotide sequence or a Rep coding nucleotide sequence.

Herein, the terms "coding nucleotide sequence", "protein-encoding gene" or "protein-coding nucleotide sequence" refer to a nucleotide sequence that encodes or is translated into a protein product, such as structural AAV capsid proteins (VP proteins) or non-structural AAV replication proteins (Rep proteins). "Operably linked" means that the expression control sequence is positioned relative to the coding sequence such that it can promote the expression of the encoded gene product.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, untranslated regions (UTRs), internal ribosome entry sites (IRES), transcription terminators, a start codon in front of a protein-encoding gene, splicing signal for introns, and stop codons. The term "expression control sequence" is intended to include, at a minimum, a sequence whose presence are engineered to influence expression of a nucleotide sequence, and can also include additional advantageous components. For example, leader sequences and fusion partner sequences can be expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of an mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

In certain embodiments, the expression control sequence can include one or more promoters. Promoters can include, but are not limited to, baculovirus major late promoters, insect virus promoters, non-insect virus promoters, vertebrate virus promoters, nuclear gene promoters, chimeric promoters from one or more species including virus and non-virus elements, and/or synthetic promoters. In certain embodiments, a promoter can be selected from: Op-EI, EI, ΔEI, EI-1, pH, PIO, polH (polyhedron), ΔpolH, Dmhsp70, Hr1, Hsp70, 4×Hsp27 EcRE+minimal Hsp70, IE, IE-1, ΔIE-1, ΔIE, p10, Δp10 (modified variations or derivatives of p10), p5, p19, p35, p40, p6.9, and variations or derivatives thereof. In certain embodiments, a promoter can be selected from tissue-specific promoters, cell-type-specific promoters, cell-cycle-specific promoters, and variations or derivatives thereof. In certain embodiments, a promoter can be selected from: CMV promoter, an alpha 1-antitrypsin (al-AT) promoter, a thyroid hormone-binding globulin promoter, a thyroxine-binding globlin (LPS) promoter, an HCR-ApoCII hybrid promoter, an HCR-hAAT hybrid promoter, an albumin promoter, an apolipoprotein E promoter, an α1-AT+ EaIb promoter, a tumor-selective E2F promoter, a mononuclear blood IL-2 promoter, and variations or derivatives thereof. In certain embodiments, the promoter is a low-expression promoter sequence. In certain embodiments, the promoter is an enhanced-expression promoter sequence. In certain embodiments, the promoter can include Rep or Cap promoters as described in US Patent Application 20110136227, the contents of which are herein incorporated by reference in its entirety.

In certain embodiments, a viral expression construct can include the same promoter in all nucleotide sequences. In certain embodiments, a viral expression construct can include the same promoter in two or more nucleotide sequences. In certain embodiments, a viral expression construct can include a different promoter in two or more nucleotide sequences. In certain embodiments, a viral expression construct can include a different promoter in all nucleotide sequences.

In certain embodiments the viral expression construct encodes elements to improve expression in certain cell types. In a further embodiment, the expression construct may include polh and/or ΔIE-1 insect transcriptional promoters, CMV mammalian transcriptional promoter, and/or p10 insect specific promoters for expression of a desired gene in a mammalian or insect cell.

More than one expression control sequence can be operably linked to a given nucleotide sequence. For example, a promoter sequence, a translation initiation sequence, and a stop codon can be operably linked to a nucleotide sequence.

In certain embodiments, the viral expression construct may contain a nucleotide sequence which includes start codon region, such as a sequence encoding AAV capsid proteins which include one or more start codon regions. In certain embodiments, the start codon region can be within an expression control sequence.

The translational start site of eukaryotic mRNA is controlled in part by a nucleotide sequence referred to as a Kozak sequence as described in Kozak, M *Cell*. 1986 Jan. 31:44(2):283-92 and Kozak, M. J Cell Biol. 1989 February; 108(2):229-41 the contents of each of which are herein incorporated by reference in their entirety. Both naturally occurring and synthetic translational start sites of the Kozak form can be used in the production of polypeptides by molecular genetic techniques. Kozak, M. *Mamm Genome*. 1996 August; 7(8):563-74 the contents of which are herein incorporated by reference in their entirety. Splice sites are sequences on an mRNA which facilitate the removal of parts of the mRNA sequences after the transcription (formation) of the mRNA. Typically, the splicing occurs in the nucleus, prior to mRNA transport into a cell's cytoplasm.

The method of the present disclosure is not limited by the use of specific expression control sequences. However, when a certain stoichiometry of VP products are achieved (close to 1:1:10 for VP1, VP2, and VP3, respectively) and also when the levels of Rep52 or Rep40 (also referred to as the p19 Reps) are significantly higher than Rep78 or Rep68 (also referred to as the p5 Reps), improved yields of AAV in production cells (such as insect cells) may be obtained. In certain embodiments, the p5/p19 ratio is below 0.6 more, below 0.4, or below 0.3, but always at least 0.03. These ratios can be measured at the level of the protein or can be implicated from the relative levels of specific mRNAs.

In certain embodiments, AAV particles are produced in viral production cells (such as mammalian or insect cells) wherein all three VP proteins are expressed at a stoichiometry approaching, about or which is 1:1:10 (VP1:VP2:VP3).

In certain embodiments, AAV particles are produced in viral production cells (such as mammalian or insect cells) wherein all three VP proteins are expressed at a stoichiometry approaching, about or which is 2:2:10 (VP1:VP2:VP3).

In certain embodiments, AAV particles are produced in viral production cells (such as mammalian or insect cells) wherein all three VP proteins are expressed at a stoichiometry approaching, about or which is 2:0:10 (VP1:VP2:VP3).

In certain embodiments, AAV particles are produced in viral production cells (such as mammalian or insect cells) wherein all three VP proteins are expressed at a stoichiometry approaching, about or which is 1-2:0-2:10 (VP1:VP2:VP3).

In certain embodiments, AAV particles are produced in viral production cells (such as mammalian or insect cells) wherein all three VP proteins are expressed at a stoichiometry approaching, about or which is 1-2:1-2:10 (VP1:VP2:VP3).

In certain embodiments, AAV particles are produced in viral production cells (such as mammalian or insect cells) wherein all three VP proteins are expressed at a stoichiometry approaching, about or which is 2-3:0-3:10 (VP1:VP2:VP3).

In certain embodiments, AAV particles are produced in viral production cells (such as mammalian or insect cells) wherein all three VP proteins are expressed at a stoichiometry approaching, about or which is 2-3:2-3:10 (VP1:VP2:VP3).

In certain embodiments, AAV particles are produced in viral production cells (such as mammalian or insect cells) wherein all three VP proteins are expressed at a stoichiometry approaching, about or which is 3:3:10 (VP1:VP2:VP3).

In certain embodiments, AAV particles are produced in viral production cells (such as mammalian or insect cells) wherein all three VP proteins are expressed at a stoichiometry approaching, about or which is 3-5:0-5:10 (VP1:VP2:VP3).

In certain embodiments, AAV particles are produced in viral production cells (such as mammalian or insect cells) wherein all three VP proteins are expressed at a stoichiometry approaching, about or which is 3-5:3-5:10 (VP1:VP2:VP3).

In certain embodiments, the expression control regions are engineered to produce a VP1:VP2:VP3 ratio selected from the group consisting of: about or exactly 1:0:10; about or exactly 1:1:10; about or exactly 2:1:10; about or exactly 2:1:10; about or exactly 2:2:10; about or exactly 3:0:10; about or exactly 3:1:10; about or exactly 3:2:10; about or exactly 3:3:10; about or exactly 4:0:10; about or exactly 4:1:10; about or exactly 4:2:10; about or exactly 4:3:10, about or exactly 4:4:10; about or exactly 5:5:10; about or exactly 1-2:0-2:10; about or exactly 1-2:1-2:10; about or exactly 1-3:0-3:10; about or exactly 1-3:1-3:10; about or exactly 1-4:0-4:10; about or exactly 1-4:1-4:10; about or exactly 1-5:1-5:10; about or exactly 2-3:0-3:10; about or exactly 2-3:2-3:10; about or exactly 2-4:2-4:10; about or exactly 2-5:2-5:10; about or exactly 3-4:34:10; about or exactly 3-5:3-5:10; and about or exactly 4-5:4-5:10.

In certain embodiments of the present disclosure, Rep52 or Rep78 is transcribed from the baculoviral derived polyhedron promoter, (polh). Rep52 or Rep78 can also be transcribed from a weaker promoter, for example a deletion mutant of the IE-1 promoter, the ΔIE-1 promoter, has about 20% of the transcriptional activity of that IE-1 promoter. A promoter substantially homologous to the ΔIE-1 promoter may be used. In respect to promoters, a homology of at least 50%, 60%, 70%, 80%, 90% or more, is considered to be a substantially homologous promoter.

Engineered Untranslated Regions (UTRs)

The present disclosure presents engineered untranslated regions (UTRs), including engineered UTR polynucleotides that function as a 5' UTR. Engineering the features in untranslated regions (UTRs) can improve the stability and protein production capability of the viral production constructs of the present disclosure.

The present disclosure presents viral expression constructs which include an engineered untranslated region (UTR) of the present disclosure. In some embodiments, the viral expression construct includes an engineered untranslated region (UTR) of the present disclosure. In some embodiments, the viral expression construct includes an engineered 5' UTR of the present disclosure.

Natural 5' UTRs include features which play important roles in translation initiation. They harbor signatures such as a Kozak sequences which are known to be involved in the process by which the ribosome initiates translation of many genes. The present disclosure provides engineered polynucleotide sequences which include at least one 5' UTR function. Such "engineered 5' UTR polynucleotides" or "engineered 5' UTRs" may also include the start codon of the protein whose expression is being driven, e.g., a structural AAV capsid protein (VP1, VP2 or VP3) or a non-structural AAV replication protein (Rep78 or Rep52).

According to the present disclosure, the engineered 5' UTR polynucleotides may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides). Non-UTR sequences may be incorporated into the engineered 5' UTRs. For example, introns or portions of introns sequences may be incorporated into the polynucleotides of the disclosure. Incorporation of intronic sequences may also increase AAV serotype protein (e.g., capsid) production.

Leader sequences may be included in the engineered polynucleotides. Such leader sequences may derive from or be identical to all or a portion of any AAV serotype selected from those taught herein.

"Features", when referring to polynucleotides, are defined as distinct nucleic acid sequence-based components of a molecule. Features of the polynucleotides of the present disclosure include local conformational shape, loops, half-loops, domains, half-domains, sites, termini or any combination thereof.

As used herein when referring to polynucleotides the term "local conformational shape" means a polynucleotide based structural manifestation which is located within a definable region of the polynucleotide.

As used herein the term "turn" as it relates to nucleic acid conformation means a bend which alters the direction of the backbone of a polynucleotide and may involve one, two, three or more nucleoside residues.

As used herein when referring to polynucleotides the term "loop" refers to a structural feature which may serve to reverse the direction of the backbone of a polynucleotide such that two regions at a distance of the polynucleotide are brought together spatially. Loops may be open or closed. Closed loops or "cyclic" loops may include 2, 3, 4, 5, 6, 7, 8, 9, 10 or more nucleotides.

As used herein the term "half-loop" refers to a portion of an identified loop having at least half the number of nucleic acid resides as the loop from which it is derived. It is understood that loops may not always contain an even number nucleic acid residues. Therefore, in those cases where a loop contains or is identified to include an odd number, a half-loop of the odd-numbered loop will include the whole number portion or next whole number portion of the loop (number of amino acids of the loop/2+/−0.5 amino acids). For example, a loop identified as a 7-nucleotide loop could produce half-loops of 3 nucleotides or 4 nucleotides (7/2=3.5+/−0.5 being 3 or 4).

As used herein the term "domain" refers to a motif of a polynucleotide having one or more identifiable structural or functional characteristics or properties (e.g., binding capacity, serving as a site for interactions).

As used herein the term "half-domain" means a portion of an identified domain having at least half the number of nucleic acid residues as the domain from which it is derived. It is understood that domains may not always contain an even number of nucleic acid residues. Therefore, in those cases where a domain contains or is identified to include an odd number, a half-domain of the odd-numbered domain will include the whole number portion or next whole number portion of the domain (number of nucleotides of the domain/2+/−0.5 nucleotides). For example, a domain identified as a 7-nucleotide domain could produce half-domains of 3 nucleotides or 4 nucleotides (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the nucleotides that include any of the domain types herein need not be contiguous along the backbone of the polynucleotide (i.e., nonadjacent nucleotides may fold structurally to produce a domain, half-domain or subdomain).

As used herein the terms "site" as it pertains to polynucleotides is used synonymously with "nucleic acid residue" and/or "nucleotide." A site represents a position within a polynucleotide that may be modified, manipulated, altered, derivatized or varied.

As used herein the terms "termini" or "terminus" refers to an extremity of a polynucleotide. Such extremity is not limited only to the first or final site of the polynucleotide but may include additional nucleotides in the terminal regions. The polynucleotides of the present disclosure may be characterized as having both a 5' and a 3' terminus.

Once any of the features have been identified or defined as a desired component of a polynucleotide of the disclosure, any of several manipulations and/or modifications of these features may be performed by moving, swapping, inverting, deleting, randomizing or duplicating. Furthermore, it is understood that manipulation of features may result in the same outcome as a modification to the molecules of the disclosure.

Modifications and manipulations can be accomplished by methods known in the art such as, but not limited to random or site directed mutagenesis. The resulting modified molecules may then be tested for activity using in vitro or in vivo assays such as those described herein or any other suitable screening assay known in the art.

According to the present disclosure, the polynucleotides may include a consensus sequence which is discovered through rounds of experimentation. As used herein a "consensus" sequence is a single sequence which represents a collective population of sequences allowing for variability at one or more sites.

In some embodiments, variants of the polynucleotides of the disclosure may be generated. These variants may have the same or a similar activity as the reference polynucleotide. Alternatively, the variant may have an altered activity (e.g., increased or decreased) relative to a reference polynucleotide. Generally, variants of a particular polynucleotides of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide as determined by sequence alignment programs and parameters described herein and known to those skilled in the art. Such tools for alignment include those of the BLAST suite (Stephen F. Altschul, Thomas L. Madden, Alejandro A. Schäffer, Jinghui Zhang, Zheng Zhang, Webb Miller, and David J. Lipman (1997). "Gapped BLAST and PSI-BLAST: a new generation of protein database search programs", Nucleic Acids Res. 25:3389-3402.) Other tools are described herein, specifically in the definition of "identity."

The engineered polynucleotides of the present disclosure may be incorporated into a vector or plasmid alone or in combination with other polynucleotide sequences or features such as those disclosed in International Publications WO2007046703 and WO2007148971 (disclosing alternative start codons and AAV vectors produced in insect cells); WO2009104964 (disclosing optimization of expression of AAV proteins in insect cells and involving alteration of promoter strength, enhancer elements, temperature control); and WO2015137802 (disclosing alternative start codons, removal of start codons and AAV vectors produced in insect cells), the contents of each of which are incorporated herein by reference in their entirety.

5' UTR Scaffolds

An embodiment of a 5' UTR of the present disclosure is presented in FIG. 1. The figure illustrates a promoter 5' (upstream) of a 5' UTR which includes an "A" region (a 5' flanking region) which is 5' (upstream) of a hairpin, a "B" region (a 3' flanking region which can include a start codon and kozak nucleotides around the start codon) which is 3' (downstream) from the stem loop, a "C" region representing the stem of a stem-loop structure, and a loop (which can range from 4-16 nucleotides). In the figure, the Kozak shown is TTT. The promoter and 5' UTR are associated with either a CAP gene (which encodes the structural capsid proteins VP1, VP2 and/or VP3) or a REP gene (which encodes the non-structural replication proteins Rep78 and Rep52).

The engineered 5' UTRs of the disclosure may have varied G:C content or percentage. In some embodiments, the 5' flanking region of the 5' UTRs have a varied G:C content. In some embodiments, the stem of the 5' UTRs has a varied G:C content. In some embodiments, the 3' flanking region of the 5' UTRs has a varied G:C content. In some embodiments, the G:C content of the engineered 5' UTR is 10-80%, 20-70%, 25%-65%, or 30%-60%. In some embodiments, the G:C content of the engineered 5' UTR is about 25%, about 30%, 34%, about 35%, about 40%, about 45%, about 50%, about 55%, 58%, about 60%, 62% or about 65%.

In some embodiments, the engineered 5' UTR includes or consists of between 80-120 nucleotides, between 90-110 nucleotides, between 95-105 nucleotides, between 98-100 nucleotides, or about 99 nucleotides. In some embodiments, the engineered 5' UTR includes or consists of 24 nucleotides.

In some embodiments, the engineered 5' UTR is derived from AAV2. In some embodiments, the engineered 5' UTR is derived from AAV2. In some embodiments, the engineered 5' UTR is derived from AAVRh10. In some embodiments, the engineered 5' UTR is derived from AAVPHP.B.

In some embodiments, the engineered 5' UTR includes or consists of between 98-100 nucleotides, and includes a G:C content of about 25%, about 30%, 34%, about 35%, about 40%, about 45%, about 50%, about 55%, 58%, about 60%, 62% or about 65%.

In some embodiments, the engineered 5' UTR includes a hairpin structure. In some embodiments, the engineered 5' UTR includes a hairpin structure encoded by a hairpin nucleotide sequence. In some embodiments, the hairpin nucleotide sequence includes a leader sequence. In some embodiments, the hairpin nucleotide sequence includes a leader sequence and a start codon (e.g. ATG). In some embodiments, the hairpin nucleotide sequence includes a leader sequence, and a start codon (e.g. ATG) within a kozak sequence or modified kozak sequence.

In some embodiments, the engineered 5' UTR includes a hairpin structure having a 5' flanking region (i.e. upstream region) encoded by a 5' flanking sequence. In some embodiments, the 5' flanking sequence may be of any length and may be derived in whole or in part from wild type AAV sequence or be completely artificial.

In some embodiments, the engineered 5' UTR includes a hairpin structure having a 3' flanking region (i.e. downstream region) encoded by a 3' flanking sequence. In some embodiments, the 3' flanking sequence may be of any length and may be derived in whole or in part from wild type AAV sequence or be completely artificial.

The 5' flanking sequence and 3' flanking sequence can have the same size and origin, a different size, a different origin, or a different size and origin. Either flanking sequence may be absent. The 5' flanking sequence can include or consist of 2-50, 2-40, 2-30, 2-20, or 2-15 nucleotides. The 3' flanking sequence can include or consist of 2-50, 2-40, 2-30, 2-20, or 2-15 nucleotides. The 3' flanking sequence may optionally contain the start codon of an AAV protein or proteins as well as other sequences such as a Kozak or modified Kozak sequence.

In some embodiments, the engineered 5' UTR includes a hairpin structure which includes a step-loop structure. In some embodiments, the hairpin structure includes a stem region and a loop region. In some embodiments, the hairpin structure includes a stem region, a loop region, and a stem-complement region. The stem-loop structure can include a stem region encoded by a stem sequence. The stem-loop structure can include a loop region encoded by a loop sequence. The stem-loop structure can include a stem-complement region encoded by a stem-complement sequence. Forming the stem of the stem-loop structure of the hairpin are paired or substantially paired nucleobases of between 2 and 50 pairs. The stem may contain one or more mismatches, bulges or loops. In some embodiments, the stem sequence and the stem-complement sequence are 100% complementary (i.e. zero mismatches). In some embodiments, the stem sequence and the stem-complement sequence include zero, one, two, three, four or five mismatches.

In some embodiments, the engineered 5' UTR includes a hairpin structure presented in Table 1. In Table 1, the name includes the parental serotype (e.g., AAV2), the hairpin number (e.g., HP1 etc.), the characteristics of the hairpin are given where the parent serotype is given, followed by the length of the hairpin, the number of mismatches (where position is an uppercase letter in the sequence), the location of the canonical start codon (e.g., ATG) and the Kozak sequence. The position of the loop portion of the hairpin is underlined in the sequence with the canonical ATG start codon in bold. The sequence of each hairpin is given in Table 1 as well as the resulting VP1:VP2:VP3 incorporation ratio relative to VP3 having a value of 10.

TABLE 1

| Name | Design | Characteristic | Hairpin Sequence | Ratio (VP1:VP2:VP3) |
|---|---|---|---|---|
| AAV2-HP1 | 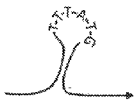 | AAV2<br>HP: 10 bp<br>0 mismatch<br>ATG in the loop<br>Kozak: TTT | atacgactcgacgaagacttgatc<br>aaccgtcggctttatggct<br>(SEQ ID NO: 1) | |
| AAV2-HP2 | 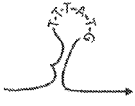 | AAV2<br>HP: 10 bp<br>1 mismatch(Base)<br>ATG in the loop<br>Kozak: TTT | atacgactcgacgaagacttgatc<br>aaccAtcggctttatggct<br>(SEQ ID NO: 2) | |
| AAV2-HP3 | 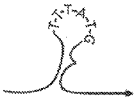 | AAV2<br>HP: 10 bp<br>1 mismatch(loop)<br>ATG in the loop<br>Kozak: TTT | atacgactcgacgaagacttgatc<br>aaccgtAggctttatggct<br>(SEQ ID NO: 3) | |
| AAV2-HP4 |  | AAV2<br>HP: 4 bp<br>0 mismatch<br>ATG in the loop<br>Kozak: TTT | atacgactcgacgaagacttgatc<br>ctgactcggctttatggct<br>(SEQ ID NO: 4) | |
| AAV2-HP5 |  | AAV2<br>HP: 14 bp<br>1 mismatch<br>ATG in the loop<br>Kozak: TTT | atacgactcgacgaagacttagTt<br>aaccgtcggctttatggct<br>(SEQ ID NO: 5) | |
| AAV2-HP6 | 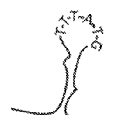 | AAV2<br>HP: 14 bp<br>2 mismatches<br>ATG in the loop<br>Kozak: TTT | atacgactcgacgaagacttagTt<br>aaccgtcCgctttatggct<br>(SEQ ID NO: 6) | 34.6<br>0<br>10 |
| AAV2-HP7 | 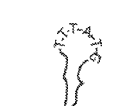 | AAV2<br>HP: 14 bp<br>3 mismatches<br>ATG in the loop<br>Kozak: TTT | atacgactcgacgaagacttagTt<br>aacTgtcCgctttatggct<br>(SEQ ID NO: 7) | 19.1<br>0<br>10 |
| AAV2-HP8 |  | AAV2<br>HP: 5 bp<br>0 mismatch<br>3 bp from ATG<br>Kozak: TTT | atacgactcgacgaagacctgcca<br>tctaaggcagtttatggct<br>(SEQ ID NO: 8) | 2.6<br>1.3<br>10 |
| AAV2-HP9 | 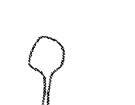 | AAV2<br>HP: 10 bp<br>0 mismatch<br>3 bp from ATG<br>Kozak: TTT | atacgactctgccagctcatctaag<br>agctggcagtttatggct<br>(SEQ ID NO: 9) | 0.3<br>0.2<br>10 |
| AAV2-HP10 | 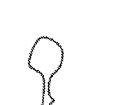 | AAV2<br>HP: 10 bp<br>1 mismatch<br>3 bp from ATG<br>Kozak: TTT | atacgactctgccTgctcatctaag<br>agctggcagtttatggct<br>(SEQ ID NO: 10) | 9.2<br>0.6<br>10 |
| AAV2-HP11 | | | atacctgccagctcttcgatctaac<br>gaagagctggcagtttatggct<br>(SEQ ID NO: 11) | |

TABLE 1-continued

| Name | Design | Characteristic | Hairpin Sequence | Ratio (VP1:VP2:VP3) |
|------|--------|----------------|------------------|---------------------|
| AAV2-HP12 | 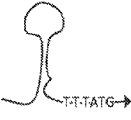 | AAV2<br>HP: 14 pb<br>1 mismatch<br>3 bp from ATG<br>Kozak: TTT | atacctgccTgctcttcgatctaacg<br>aagagctggcagtttatggct<br>(SEQ ID NO: 12) | 9.8<br>0.4<br>10 |
| AAV2-HP13 | 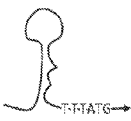 | AAV2<br>HP: 14 pb<br>2 mismatches<br>3 bp from ATG<br>Kozak: TTT | atacctgccTgctcAtcgatctaac<br>gaagagctggcagtttatggct<br>(SEQ ID NO: 13) | 7.7<br>1.0<br>10 |
| AAV2-HP14 | 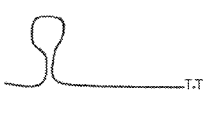 | AAV2<br>HP: 5 bp<br>0 mismatch<br>17 bp from ATG<br>Kozak: TTT | atacctgccatctaaggcaggactc<br>gacgaagactttatggct<br>(SEQ ID NO: 14) | ND |
| AAV2-HP15 | 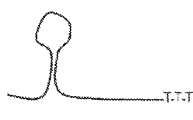 | AAV2<br>HP: 14 bp<br>0 mismatch<br>17 bp from the ATG<br>Kozak: TTT | atacctgccagctcatctaagagct<br>ggcaggacttttatggct<br>(SEQ ID NO: 15) | 25.1<br>0<br>10 |
| AAV2-HP16 | 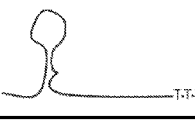 | AAV2<br>HP: 14 bp<br>1 mismatch<br>17 pb from ATG<br>Kozak: TTT | atacctgccTgctcatctaagagct<br>ggcaggacttttatggct<br>(SEQ ID NO: 16) | 17.7<br>0.3<br>10 |

In some embodiments, the engineered 5' UTR includes a hairpin structure, or a component thereof, which is encoded by a hairpin nucleotide sequence selected from SEQ ID NO: 1-16. In some embodiments, the engineered 5' UTR includes a hairpin structure, or a component thereof, encoded by a nucleotide sequence having at least 60% identity, at least 65% identity, at least 70% identity, at least 75% identity, at least 80% identity, at least 85% identity, at least 90% identity or at least 95% identity to SEQ ID NO: 1-16.

In some embodiments, the engineered 5' UTR includes a Hairpin 1 structure, or a component thereof. In some embodiments, the engineered 5' UTR includes a Hairpin 2 structure, or a component thereof. In some embodiments, the engineered 5' UTR includes a Hairpin 3 structure, or a component thereof. In some embodiments, the engineered 5' UTR includes a Hairpin 4 structure, or a component thereof. In some embodiments, the engineered 5' UTR includes a Hairpin 5 structure, or a component thereof. In some embodiments, the engineered 5' UTR includes a Hairpin 6 structure, or a component thereof. In some embodiments, the engineered 5' UTR includes a Hairpin 7 structure, or a component thereof. In some embodiments, the engineered 5' UTR includes a Hairpin 8 structure, or a component thereof. In some embodiments, the engineered 5' UTR includes a Hairpin 10 structure, or a component thereof. In some embodiments, the engineered 5' UTR includes a Hairpin 11 structure, or a component thereof. In some embodiments, the engineered 5' UTR includes a Hairpin 13 structure, or a component thereof. In some embodiments, the engineered 5' UTR includes a Hairpin 14 structure, or a component thereof. In some embodiments, the engineered 5' UTR includes a Hairpin 15 structure, or a component thereof. In some embodiments, the engineered 5' UTR includes a Hairpin 16 structure, or a component thereof.

In some embodiments, the engineered 5' UTR includes a Hairpin 9 structure, or a component thereof. In some embodiments, the engineered 5' UTR includes a hairpin structure, or a component thereof, which is encoded by a hairpin nucleotide sequence comprising SEQ ID NO: 9.

In some embodiments, the engineered 5' UTR includes a Hairpin 12 structure, or a component thereof. In some embodiments, the engineered 5' UTR includes a hairpin structure, or a component thereof, which is encoded by a hairpin nucleotide sequence comprising SEQ ID NO: 12.

In some embodiments, the engineered 5' UTR includes a hairpin structure, or one or more components thereof, selected from the structures and regions presented in Table 2. The disclosure in Table 2 includes: the hairpin number (e.g., HP1) the hairpin sequence (start codon is bolded and loop is underlined) for certain hairpin structures, the upstream region sequences (Region A in FIG. 1) for certain hairpin structures, the stem region sequences (Region C in FIG. 1) for certain hairpin structures, the loop sequences (Region A in FIG. 1) for certain hairpin structures, the stem complement sequences for certain hairpin structures, the downstream region sequences (Region B in FIG. 1) for certain hairpin structures, and the lead sequences for certain hairpin structures.

TABLE 2

| HP # | Hairpin sequence | Upstream Region (A) | Stem Region (C) | Loop | Stem Complement | Downstream Region (B) | Leader Sequence |
|------|------------------|---------------------|-----------------|------|-----------------|----------------------|-----------------|
| 1 | atacgactcga<br>cgaagacttga<br>tcaaccgtcgg | atacgactcga<br>cgaagacttga<br>tc | aaccgtcggc<br>SEQ ID<br>NO: 21 | tttatggct | | | Atacgactcg<br>acgaagacttg<br>atcaaccgtcg |

TABLE 2-continued

| HP # | Hairpin sequence | Upstream Region (A) | Stem Region (C) | Loop | Stem Complement | Downstream Region (B) | Leader Sequence |
|---|---|---|---|---|---|---|---|
| | ctttatggct SEQ ID NO: 1 | SEQ ID NO: 17 | | | | | gcttt SEQ ID NO: 36 |
| 2 | atacgactcga cgaagacttga tcaaccAtcgg ctttatggct SEQ ID NO: 2 | atacgactcga cgaagacttga tc SEQ ID NO: 17 | aaccAtcggc SEQ ID NO: 22 | tttatggct | | | atacgactcga cgaagacttga tcaaccAtcg gcttt SEQ ID NO: 37 |
| 3 | atacgactcga cgaagacttga tcaaccgtAg gctttatggct SEQ ID NO: 3 | atacgactcga cgaagacttga tc SEQ ID NO: 17 | aaccgtAggc SEQ ID NO: 23 | tttatggct | | | atacgactcga cgaagacttga tcaaccgtAg gcttt SEQ ID NO: 38 |
| 4 | atacgactcga cgaagacttga tcctgactcgg ctttatggct SEQ ID NO: 4 | atacgactcga cgaagacttga tcctgact SEQ ID NO: 18 | cggc | tttatggct | | | atacgactcga cgaagacttga tcctgactcgg cttt SEQ ID NO: 39 |
| 5 | atacgactcga cgaagacttag Ttaaccgtcgg ctttatggct SEQ ID NO: 5 | atacgactcga cgaagacttt SEQ ID NO: 19 | agTtaaccgtc ggc SEQ ID NO: 24 | tttatggct | | | atacgactcga cgaagacttag Ttaaccgtcg gcttt SEQ ID NO: 40 |
| 6 | atacgactcga cgaagacttag TtaaccgtcC gctttatggct SEQ ID NO: 6 | atacgactcga cgaagacttt SEQ ID NO: 19 | agTtaaccgtc Cgc SEQ ID NO: 25 | tttatggct | | | atacgactcga cgaagacttag TtaaccgtcC gcttt SEQ ID NO: 41 |
| 7 | atacgactcga cgaagacttag TtaacTgtcC gctttatggct SEQ ID NO: 7 | atacgactcga cgaagacttt SEQ ID NO: 19 | agTtaacTgt cCgc SEQ ID NO: 26 | tttatggct | | | atacgactcga cgaagacttag TtaacTgtcC gcttt SEQ ID NO: 42 |
| 8 | atacgactcga cgaagacctgc catctaaggca gtttatggct SEQ ID NO: 8 | atacgactcga cgaagac SEQ ID NO: 20 | ctgcc | atctaa | ggcag | tttatggct | atacgactcga cgaagacctg ccatctaaggc agttt SEQ ID NO: 43 |
| 9 | atacgactctgc cagctcatctaa gagctggcagt ttatggct SEQ ID NO: 9 | atacgact | ctgccagctc SEQ ID NO: 27 | atctaa | gagctggcag SEQ ID NO: 32 | tttatggct | atacgactctg ccagctcatct aagagctggc agttt SEQ ID NO: 44 |
| 10 | atacgactctgc cTgctcatcta agagctggca gtttatggct SEQ ID NO: 10 | atacgact | ctgccTgctc SEQ ID NO: 28 | atctaa | gagctggcag SEQ ID NO: 32 | tttatggct | atacgactctg ccTgctcatct aagagctggc agttt SEQ ID NO: 45 |
| 11 | atacctgccag ctcttcgatcta acgaagagctg gcagtttatgg ct SEQ ID NO: 11 | atac | ctgccagctctt cg SEQ ID NO: 29 | atctaa | cgaagagctgg ag SEQ ID NO: 33 | tttatggct | atacctgccag ctcttcgatcta acgaagagct ggcagttt SEQ ID NO: 46 |

TABLE 2-continued

| HP # | Hairpin sequence | Upstream Region (A) | Stem Region (C) | Loop | Stem Complement | Downstream Region (B) | Leader Sequence |
|---|---|---|---|---|---|---|---|
| 12 | atacctgccTg ctcttcgatcta acgaagagctg gcagtttatgg ct SEQ ID NO: 12 | atac | ctgccTgctctt cg SEQ ID NO: 30 | atctaa | cgaagagctggc ag SEQ ID NO: 33 | tttatggct | atacctgccT gctcttcgatct aacgaagagc tggcagttt SEQ ID NO: 47 |
| 13 | atacctgccTg ctcAtcgatct aacgaagagct ggcagtttatg gct SEQ ID NO: 13 | atac | ctgccTgctc Atcg SEQ ID NO: 31 | atctaa | cgaagagctggc ag SEQ ID NO: 33 | tttatggct | atacctgccT gctcAtcgat ctaacgaaga gctggcagttt SEQ ID NO: 48 |
| 14 | atacctgccatc taaggcaggac tcgacgaagac tttatggct SEQ ID NO: 14 | atac | ctgcc | atctaa | ggcag | gactcgacgaag actttatggct SEQ ID NO: 34 | atacctgccat ctaaggcagg actcgacgaa gacttt SEQ ID NO: 49 |
| 15 | atacctgccag ctcatctaagag ctggcaggact tttatggct SEQ ID NO: 15 | atac | ctgccagctc SEQ ID NO: 27 | atctaa | gagctggcag SEQ ID NO: 32 | gactttatggct SEQ ID NO: 35 | atacctgccag ctcatctaaga gctggcagga ctttt SEQ ID NO: 50 |
| 16 | atacctgccTg ctcatctaagag ctggcaggact tttatggct SEQ ID NO: 16 | atac | ctgccTgctc SEQ ID NO: 28 | atctaa | gagctggcag SEQ ID NO: 32 | gactttatggct SEQ ID NO: 35 | atacctgccT gctcatctaag agctggcagg actttt SEQ ID NO: 51 |

In some embodiments, the engineered 5' UTR includes a hairpin structure which includes an upstream region encoded by a nucleotide sequence selected from atacgact, atac, and SEQ ID NO: 17-20. In some embodiments, the engineered 5' UTR includes a hairpin structure which includes an upstream region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from atacgact, atac, and SEQ ID NO: 17-20. The upstream region may be of any length, including (but not limited to) between 4-30 nucleotides, between 4-20 nucleotides, between 4-15 nucleotides, between 5-15 nucleotides, between 6-12 nucleotides, 6 nucleotides, 7, nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides or 20 nucleotides.

In some embodiments, the engineered 5' UTR includes a hairpin structure which includes a downstream region encoded by a nucleotide sequence selected from tttatggct, attatggct, tatatggct, ttaatggct, taaatggct, ataatggct, and SEQ ID NO: 34-35. In some embodiments, the engineered 5' UTR includes a hairpin structure which includes an downstream region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from tttatggct, attatggct, tatatggct, ttaatggct, taaatggct, ataatggct, and SEQ ID NO: 34-35. The upstream region may be of any length, including (but not limited to) between 0-30 nucleotides, between 0-20 nucleotides, between 0-15 nucleotides, between 4-15 nucleotides, between 6-12 nucleotides, 0 nucleotides, 1, nucleotide, 2 nucleotides, 3 nucleotides, 4 nucleotides, 5, nucleotides, 6 nucleotides, 7, nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides or 20 nucleotides.

In some embodiments, the engineered 5' UTR includes a hairpin structure which includes a stem region encoded by a nucleotide sequence selected from cggc, ctgcc and SEQ ID NO: 21-31. In some embodiments, the engineered 5' UTR includes a hairpin structure which includes an stem region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from cggc, ctgcc and SEQ ID NO: 21-31. The stem region may be of any length, including (but not limited to) between 4-30 nucleotides, between 4-20 nucleotides, between 4-15 nucleotides, between 5-15 nucleotides, between 6-12 nucleotides, 4 nucleotides, 5, nucleotides, 6 nucleotides, 7, nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides or 20 nucleotides.

In some embodiments, the engineered 5' UTR includes a hairpin structure which includes a stem complement region encoded by a nucleotide sequence selected from ggcag and SEQ ID NO: 32-33. In some embodiments, the engineered 5' UTR includes a hairpin structure which includes an stem complement region encoded by a nucleotide sequence having at least 60% identity, at least 65% identity, at least 70% identity, at least 75% identity, at least 80% identity, at least 85% identity, at least 90% identity or at least 95% identity to a nucleotide sequence selected from ggcag and SEQ ID NO: 32-33. The stem complement region may be of any length, including (but not limited to) between 0-30 nucleotides, between 0-20 nucleotides, between 0-15 nucleotides, between 4-15 nucleotides, between 6-12 nucleotides, 0 nucleotides, 1, nucleotide, 2 nucleotides, 3 nucleotides, 4 nucleotides, 5, nucleotides, 6 nucleotides, 7, nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides or 20 nucleotides.

In some embodiments, the engineered 5' UTR includes a hairpin structure which includes a loop region encoded by a nucleotide sequence selected from tttatggct and atctaa. In some embodiments, the engineered 5' UTR includes a hairpin structure which includes a loop region encoded by a nucleotide sequence having at least 60% identity, at least 65% identity, at least 70% identity, at least 75% identity, at least 80% identity, at least 85% identity, at least 90;% identity or at least 95% identity to a nucleotide sequence selected from tttatggct and atctaa. The upstream region may be of any length, including (but not limited to) between 4-30 nucleotides, between 4-20 nucleotides, between 4-15 nucleotides, between 5-15 nucleotides, between 6-12 nucleotides, 4, nucleotides, 5 nucleotides, 6 nucleotides, 7, nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides or 20 nucleotides.

In some embodiments, the engineered 5' UTR includes a hairpin structure which includes a leader sequence selected from SEQ ID NO: 36-51. In some embodiments, the engineered 5' UTR includes a hairpin structure which includes a leader sequence selected from SEQ ID NO: 59-63. In some embodiments, the engineered 5' UTR includes a hairpin structure which includes a leader sequence having at least 60% identity, at least 65% identity, at least 70% identity, at least 75% identity, at least 80% identity, at least 85% identity, at least 90% identity or at least 95% identity to a nucleotide sequence selected from SEQ ID NO: 36-51. In some embodiments, the engineered 5' UTR includes a hairpin structure which includes a leader sequence having at least 60% identity, at least 65% identity, at least 70% identity, at least 75% identity, at least 80% identity, at least 85% identity, at least 90% identity or at least 95% identity to a nucleotide sequence selected from SEQ ID NO: 59-63.

As used herein a "5' UTR scaffold" is a framework or starting polynucleotide that forms the sequence or structural basis against which to design or make a subsequent engineered polynucleotide.

In some embodiments, an engineering 5' UTR is engineered according to one or more of the following parameters: length of 5' flanking region, length of 5' stem arm, length of loop, length of 3' stem arm, length of 3' flanking region, G:C % in hairpin sequence, and the number of stem mismatches.

The 5' and 3' arms of the stem may be completely complementary across a substantial portion of their length. In other embodiments, the 5' and 3' arms of the stem may be at least 70, 80, 90, 95 or 99% complementary across independently at least 50, 60, 70, 80, 85, 90, 95, or 99% of the length.

Separating the 5' and 3' arms of the stem of the stem loop structure is a loop (also known as a loop motif). The loop may be of any length, between 4-30 nucleotides, between 4-20 nucleotides, between 4-15 nucleotides, between 5-15 nucleotides, between 6-12 nucleotides, 6 nucleotides, 7, nucleotides, 8 nucleotides, 9 nucleotides, 10 nucleotides, 11 nucleotides, and/or 12 nucleotides.

In some embodiments, the loop includes the start codon of the AAV protein.

Spacer regions may be present in the engineered 5' UTRs to separate one or more features from one another. There may be one or more such spacer regions present.

In some embodiments, a spacer region of between 8-20. i.e., 8, 9, 10, 11, 12, 13, 14, 15, 16, 17, 18, 19, or 20 nucleotides may be present between any two or more features.

In some embodiments, the engineered 5' UTR includes in the 5' to 3' direction, a 5' flanking sequence, a 5' arm, a loop motif, a 3' arm and a 3' flanking sequence.

In some embodiments, the 5' arm, loop motif and/or 3' arm sequence may be altered (e.g., substituting 1 or more nucleotides, adding nucleotides and/or deleting nucleotides). The alteration may cause a beneficial change in the function of the construct.

In some embodiments, the modulatory polynucleotide is designed using at least one of the following properties: loop variant, mismatch/bulge/wobble variant, stem mismatch, loop variant, stem mismatch variant or a stem sequence variant.

Figure 2A:
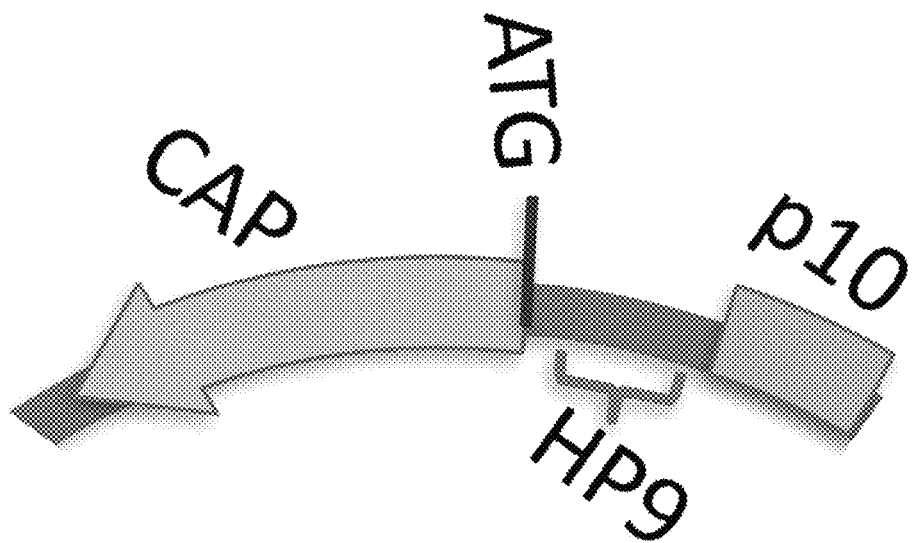
FIG. 2A shows one embodiment of a viral expression construct of the present disclosure which includes a VP-coding region and an expression control sequence which includes a promoter and a hairpin structure.

One embodiment of a viral expression construct of the present disclosure is shown in FIG. 2A. The expression control sequence of the viral expression construct includes a p10 promoter (SEQ ID NO: 52) and an engineered 5' UTR which includes an ATG start codon within AAV2-HP9 (SEQ ID NO: 9). The viral expression construct also includes an AAV2-CAP sequence coding for VP proteins (SEQ ID NO: 53). The viral expression construct is encoded by SEQ ID NO: 54.

Figure 2B:
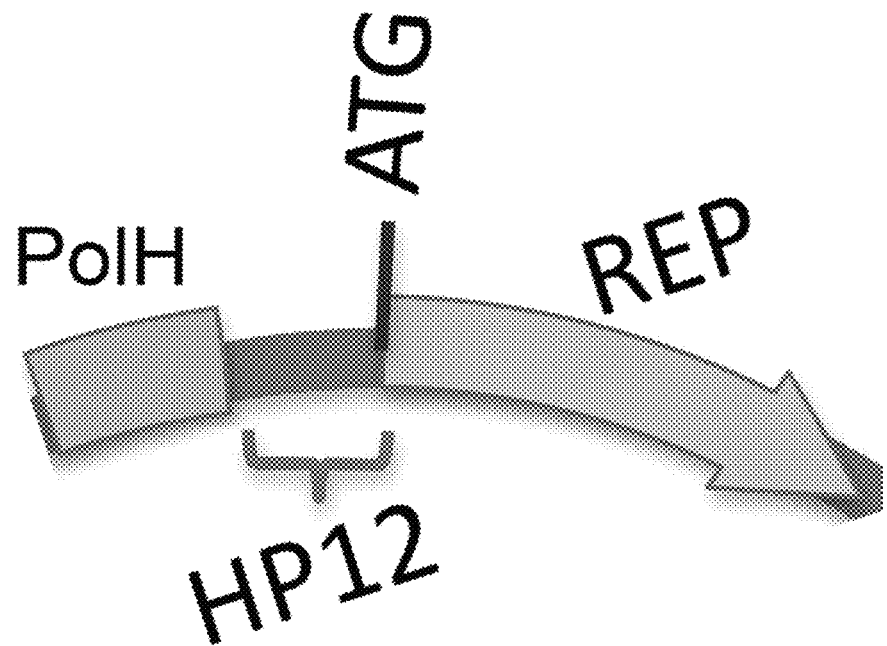
FIG. 2B shows one embodiment of a viral expression construct of the present disclosure which include a Rep-coding region and an expression control sequence which includes a promoter and a hairpin structure.

One embodiment of a viral expression construct of the present disclosure is shown in FIG. 2B. The expression control sequence of the viral expression construct includes a polH promoter (SEQ ID NO: 55) and an engineered 5' UTR which includes an ATG start codon within AAV2-HP9 (SEQ ID NO: 9) or a modified AAV2-HP9 (SEQ ID NO: 56). The viral expression construct also includes a REP sequence coding for Rep proteins (SEQ ID NO: 57). The viral expression construct is encoded by SEQ ID NO: 58.

Figure 2C:
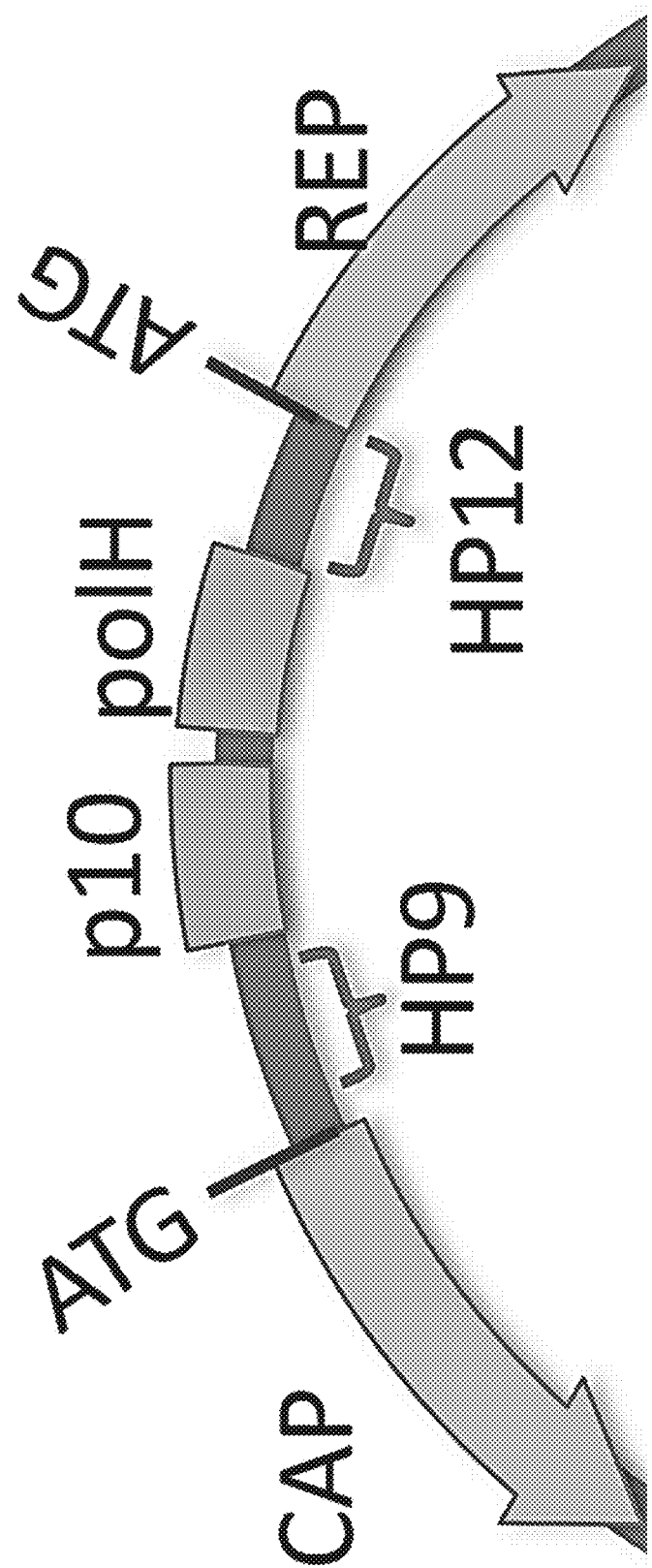
FIG. 2C shows one embodiment of a viral expression construct of the present disclosure which includes both a Rep-coding region (with corresponding hairpin structure and promoter) and a VP-coding region (with corresponding hairpin structure and promoter).

One embodiment of a viral expression construct of the present disclosure is shown in FIG. 2C, which includes both the CAP viral expression construct from FIG. 2A (SEQ ID NO: 54) and the REP viral expression construct from FIG. 2B (SEQ ID NO: 58).

Viral Production Cells and Vectors
Mammalian-Production System

Viral production of the present disclosure disclosed herein describes processes and methods for producing AAV particles or viral vector that contacts a target cell to deliver a payload construct, e.g. a recombinant AAV particle or viral construct, which includes a nucleotide encoding a payload molecule. The viral production cell may be selected from any biological organism, including prokaryotic (e.g., bacterial) cells, and eukaryotic cells, including, insect cells, yeast cells and mammalian cells.

In certain embodiments, the AAV particles of the present disclosure may be produced in a viral production cell that includes a mammalian cell. Viral production cells may comprise mammalian cells such as A549, WEH1, 3T3, IOT1/2, BHK, MDCK, COS 1, COS 7, BSC 1, BSC 40, BMT 10, VERO, W138, HeLa, HEK293, HEK293T (293T), Saos, C2C12, L cells, HT1080, HepG2 and primary fibroblast, hepatocyte and myoblast cells derived from mammals. Viral production cells can include cells derived from mammalian species including, but not limited to, human, monkey, mouse, rat, rabbit, and hamster or cell type, including but not limited to fibroblast, hepatocyte, tumor cell, cell line transformed cell, etc.

AAV viral production cells commonly used for production of recombinant AAV particles include, but is not limited to HEK293 cells, COS cells, C127, 3T3, CHO, HeLa cells, KB cells, BHK, and other mammalian cell lines as described in U.S. Pat. Nos. 6,156,303, 5,387,484, 5,741,683, 5,691,176, 6,428,988 and 5,688,676; U.S. patent application 2002/0081721, and International Patent Publication Nos. WO 00/47757, WO 00/24916, and WO 96/17947, the contents of each of which are herein incorporated by reference in their entireties. In certain embodiments, the AAV viral production cells are trans-complementing packaging cell lines that provide functions deleted from a replication-defective helper virus, e.g., HEK293 cells or other Ea trans-complementing cells.

In certain embodiments, the packaging cell line 293-10-3 (ATCC Accession No. PTA-2361) may be used to produce the AAV particles, as described in U.S. Pat. No. 6,281,010, the contents of which are herein incorporated by reference in its entirety.

In certain embodiments, of the present disclosure a cell line, such as a HeLA cell line, for trans-complementing E1 deleted adenoviral vectors, which encoding adenovirus E1a and adenovirus E1b under the control of a phosphoglycerate kinase (PGK) promoter can be used for AAV particle production as described in U.S. Pat. No. 6,365,394, the contents of which are incorporated herein by reference in their entirety.

In certain embodiments, AAV particles are produced in mammalian cells using a triple transfection method wherein a payload construct, parvoviral Rep and parvoviral Cap and a helper construct are comprised within three different constructs. The triple transfection method of the three components of AAV particle production may be utilized to produce small lots of virus for assays including transduction efficiency, target tissue (tropism) evaluation, and stability.

AAV particles to be formulated may be produced by triple transfection or baculovirus mediated virus production, or any other method known in the art. Any suitable permissive or packaging cell known in the art may be employed to produce the vectors. In certain embodiments, trans-complementing packaging cell lines are used that provide functions deleted from a replication-defective helper virus, e.g., 293 cells or other E1a trans-complementing cells.

The gene cassette may contain some or all of the parvovirus (e.g., AAV) cap and rep genes. In certain embodiments, some or all of the cap and rep functions are provided in trans by introducing a packaging vector(s) encoding the capsid and/or Rep proteins into the cell. In certain embodiments, the gene cassette does not encode the capsid or Rep proteins. Alternatively, a packaging cell line is used that is stably transformed to express the cap and/or rep genes.

Recombinant AAV virus particles are, in certain embodiments, produced and purified from culture supernatants according to the procedure as described in US2016/0032254, the contents of which are incorporated by reference. Production may also involve methods known in the art including those using 293T cells, triple transfection or any suitable production method.

In certain embodiments, mammalian viral production cells (e.g 293T cells) can be in an adhesion/adherent state (e.g. with calcium phosphate) or a suspension state (e.g with polyethylenimine (PEI)). The mammalian viral production cell is transfected with plasmids required for production of AAV, (i.e., AAV rep/cap construct, an adenoviral helper construct, and/or ITR flanked payload construct). In certain embodiments, the transfection process can include optional medium changes (e.g. medium changes for cells in adhesion form, no medium changes for cells in suspension form, medium changes for cells in suspension form if desired). In certain embodiments, the transfection process can include transfection mediums such as DMEM or F17. In certain embodiments, the transfection medium can include serum or can be serum-free (e.g. cells in adhesion state with calcium phosphate and with serum, cells in suspension state with PEI and without serum).

Cells can subsequently be collected by scraping (adherent form) and/or pelleting (suspension form and scraped adherent form) and transferred into a receptacle. Collection steps can be repeated as necessary for full collection of produced cells. Next, cell lysis can be achieved by consecutive freeze-thaw cycles (−80 C to 37 C), chemical lysis (such as adding detergent triton), mechanical lysis, or by allowing the cell culture to degrade after reaching ~0% viability. Cellular debris is removed by centrifugation and/or depth filtration. The samples are quantified for AAV particles by DNase resistant genome titration by DNA qPCR.

AAV particle titers are measured according to genome copy number (genome particles per milliliter). Genome particle concentrations are based on DNA qPCR of the vector DNA as previously reported (Clark et al. (1999) Hum. Gene Ther., 10:1031-1039; Veldwijk et al. (2002) Mol. Ther., 6:272-278).

Insect Cells

Viral production of the present disclosure includes processes and methods for producing AAV particles or viral vectors that contact a target cell to deliver a payload construct, e.g. a recombinant viral construct, which includes a nucleotide encoding a payload molecule. In certain embodiments, the AAV particles or viral vectors of the present disclosure may be produced in a viral production cell that includes an insect cell.

Growing conditions for insect cells in culture, and production of heterologous products in insect cells in culture are well-known in the art, see U.S. Pat. No. 6,204,059, the contents of which are herein incorporated by reference in their entirety.

Any insect cell which allows for replication of parvovirus and which can be maintained in culture can be used in accordance with the present disclosure. AAV viral production cells commonly used for production of recombinant AAV particles include, but is not limited to, *Spodoptera frugiperda*, including, but not limited to the Sf9 or Sf21 cell lines, *Drosophila* cell lines, or mosquito cell lines, such as *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, Methods In Molecular Biology, ed. Richard, Humana Press, NJ (1995); O'Reilly et al., Baculovirus Expression Vectors, A Laboratory Manual, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir. 219:37-44 (1996); Zhao et al., Vir. 272:382-93

(2000); and Samulski et al., U.S. Pat. No. 6,204,059, the contents of each of which are herein incorporated by reference in their entirety.

In one embodiment, the AAV particles are made using the methods described in WO2015/191508, the contents of which are herein incorporated by reference in their entirety.

In certain embodiments, insect host cell systems, in combination with baculoviral systems (e.g., as described by Luckow et al., Bio/Technology 6: 47 (1988)) may be used. In certain embodiments, an expression system for preparing chimeric peptide is *Trichoplusia ni*, Tn 5B1-4 insect cells/baculoviral system, which can be used for high levels of proteins, as described in U.S. Pat. No. 6,660,521, the contents of which are herein incorporated by reference in their entirety.

Expansion, culturing, transfection, infection and storage of insect cells can be carried out in any cell culture media, cell transfection media or storage media known in the art, including Hyclone SFX Insect Cell Culture Media, Expression System ESF AF Insect Cell Culture Medium, ThermoFisher Sf90011 media, ThermoFisher Sf900111 media, or ThermoFisher Grace's Insect Media. Insect cell mixtures of the present disclosure can also include any of the formulation additives or elements described in the present disclosure, including (but not limited to) salts, acids, bases, buffers, surfactants (such as Poloxamer 188/Pluronic F-68), and other known culture media elements. Formulation additives can be incorporated gradually or as "spikes" (incorporation of large volumes in a short time).

Baculovirus-Production System

In certain embodiments, processes of the present disclosure can include production of AAV particles or viral vectors in a baculoviral system using a viral expression construct and a payload construct vector. In certain embodiments, the baculoviral system includes Baculovirus expression vectors (BEVs) and/or baculovirus infected insect cells (BIICs). In certain embodiments, a viral expression construct or a payload construct of the present disclosure can be a bacmid, also known as a baculovirus plasmid. In certain embodiments, a viral expression construct or a payload construct of the present disclosure can be polynucleotide incorporated by homologous recombination (transposon donor/acceptor system) into a bacmid by standard molecular biology techniques known and performed by a person skilled in the art. Transfection of separate viral replication cell populations produces two or more groups (e.g. two, three) of baculoviruses (BEVs), one or more group that includes the viral expression construct (Expression BEV), and one or more group that includes the payload construct (Payload BEV). The baculoviruses may be used to infect a viral production cell for production of AAV particles or viral vector.

In certain embodiments, the process includes transfection of a single viral replication cell population to produce a single baculovirus (BEV) group which includes both the viral expression construct and the payload construct. These baculoviruses may be used to infect a viral production cell for production of AAV particles or viral vector.

In certain embodiments, BEVs are produced using a Bacmid Transfection agent, such as Promega FuGENE HD, WFI water, or ThermoFisher Cellfectin II Reagent. In certain embodiments, BEVs are produced and expanded in viral production cells, such as an insect cell.

In certain embodiments, the method utilizes seed cultures of viral production cells that include one or more BEVs, including baculovirus infected insect cells (BIICs). The seed BIICs have been transfected/transduced/infected with an Expression BEV which includes a viral expression construct, and also a Payload BEV which includes a payload construct. In certain embodiments, the seed cultures are harvested, divided into aliquots and frozen, and may be used at a later time to initiate transfection/transduction/infection of a naïve population of production cells. In certain embodiments, a bank of seed BIICs is stored at −80° C. or in $LN_2$ vapor.

Baculoviruses are made of several essential proteins which are essential for the function and replication of the Baculovirus, such as replication proteins, envelope proteins and capsid proteins. The Baculovirus genome thus includes several essential-gene nucleotide sequences encoding the essential proteins. As a non-limiting example, the genome can include an essential-gene region which includes an essential-gene nucleotide sequence encoding an essential protein for the Baculovirus construct. The essential protein can include: GP64 baculovirus envelope protein, VP39 baculovirus capsid protein, or other similar essential proteins for the Baculovirus construct.

Baculovirus expression vectors (BEV) for producing AAV particles in insect cells, including but not limited to *Spodoptera frugiperda* (Sf9) cells, provide high titers of viral vector product. Recombinant baculovirus encoding the viral expression construct and payload construct initiates a productive infection of viral vector replicating cells. Infectious baculovirus particles released from the primary infection secondarily infect additional cells in the culture, exponentially infecting the entire cell culture population in a number of infection cycles that is a function of the initial multiplicity of infection, see Urabe, M. et al. J Virol. 2006 February; 80(4):1874-85, the contents of which are herein incorporated by reference in their entirety.

Production of AAV particles with baculovirus in an insect cell system may address known baculovirus genetic and physical instability.

In certain embodiments, the production system of the present disclosure addresses baculovirus instability over multiple passages by utilizing a titerless infected-cells preservation and scale-up system. Small scale seed cultures of viral producing cells are transfected with viral expression constructs encoding the structural and/or non-structural components of the AAV particles. Baculovirus-infected viral producing cells are harvested into aliquots that may be cryopreserved in liquid nitrogen; the aliquots retain viability and infectivity for infection of large scale viral producing cell culture Wasilko D J et al. Protein Expr Purif. 2009 June; 65(2):122-32, the contents of which are herein incorporated by reference in their entirety.

A genetically stable baculovirus may be used to produce a source of the one or more of the components for producing AAV particles in invertebrate cells. In certain embodiments, defective baculovirus expression vectors may be maintained episomally in insect cells. In such an embodiment the bacmid vector is engineered with replication control elements, including but not limited to promoters, enhancers, and/or cell-cycle regulated replication elements.

In certain embodiments, baculoviruses may be engineered with a (non-) selectable marker for recombination into the chitinase/cathepsin locus. The chia/v-cath locus is non-essential for propagating baculovirus in tissue culture, and the V-cath (EC 3.4.22.50) is a cysteine endoprotease that is most active on Arg-Arg dipeptide containing substrates. The Arg-Arg dipeptide is present in densovirus and parvovirus capsid structural proteins but infrequently occurs in dependovirus VP1.

In certain embodiments, stable viral producing cells permissive for baculovirus infection are engineered with at least one stable integrated copy of any of the elements necessary for AAV replication and vector production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

In certain embodiments, the Baculovirus expression vectors (BEV) are based on the AcMNPV baculovirus or BmNPV baculovirus BmNPV.

In certain embodiments, the Baculovirus expression vectors (BEV) is a BEV in which the baculoviral v-cath gene has been deleted ("v-cath deleted BEV") or mutated.

Other

In certain embodiments expression hosts include, but are not limited to, bacterial species within the genera *Escherichia, Bacillus, Pseudomonas, Salmonella*.

In certain embodiments, a host cell which includes AAV rep and cap genes stably integrated within the cell's chromosomes, may be used for AAV particle production. In a non-limiting example, a host cell which has stably integrated in its chromosome at least two copies of an AAV rep gene and AAV cap gene may be used to produce the AAV particle according to the methods and constructs described in U.S. Pat. No. 7,238,526, the contents of which are incorporated herein by reference in their entirety.

In certain embodiments, the AAV particle can be produced in a host cell stably transformed with a molecule comprising the nucleic acid sequences which permit the regulated expression of a rare restriction enzyme in the host cell, as described in US20030092161 and EP1183380, the contents of which are herein incorporated by reference in their entirety.

In certain embodiments, production methods and cell lines to produce the AAV particle may include, but are not limited to those taught in PCT/US1996/010245, PCT/US1997/015716, PCT/US1997/015691, PCT/US1998/019479, PCT/US1998/019463, PCT/US2000/000415, PCT/US2000/040872, PCT/US2004/016614, PCT/US2007/010055, PCT/US1999/005870, PCT/US2000/004755, U.S. patent application Ser. Nos. 08/549,489, 08/462,014, 09/659203, 10/246,447, 10/465,302, U.S. Pat. Nos. 6,281,010, 6,270,996, 6,261,551, 5,756,283 (Assigned to NIH), U.S. Pat. Nos. 6,428,988, 6,274,354, 6,943,019, 6,482,634, (Assigned to NIH: U.S. Pat. Nos. 7,238,526, 6,475,769), U.S. Pat. Nos. 6,365,394 (Assigned to NIH), U.S. Pat. Nos. 7,491,508, 7,291,498, 7,022,519, 6,485,966, 6,953,690, 6,258,595, EP2018421, EP1064393, EP1163354, EP835321, EP931158, EP950111, EP1015619, EP1183380, EP2018421, EP1226264, EP1636370, EP1163354, EP1064393, US20030032613, US20020102714, US20030073232, US20030040101 (Assigned to NIH), US20060003451, US20020090717, US20030092161, US20070231303, US20060211115, US20090275107, US2007004042, US20030119191, US20020019050, the contents of each of which are incorporated herein by reference in their entirety.

III. Definitions

At various places in the present disclosure, substituents or properties of compounds of the present disclosure are disclosed in groups or in ranges. It is specifically intended that the present disclosure include each and every individual or subcombination of the members of such groups and ranges.

Unless stated otherwise, the following terms and phrases have the meanings described below. The definitions are not meant to be limiting in nature and serve to provide a clearer understanding of certain aspects of the present disclosure.

About: As used herein, the term "about" means +/−10% of the recited value.

Adeno-associated virus: The term "adeno-associated virus" or "AAV" as used herein refers to members of the dependovirus genus comprising any particle, sequence, gene, protein, or component derived therefrom.

AAV Particle: As used herein, an "AAV particle" is a virus which includes a capsid and a viral genome with at least one payload region and at least one ITR region. AAV particles of the present disclosure may be produced recombinantly and may be based on adeno-associated virus (AAV) parent or reference sequences. AAV particle may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Activity: As used herein, the term "activity" refers to the condition in which things are happening or being done. Compositions of the present disclosure may have activity and this activity may involve one or more biological events.

Administering: As used herein, the term "administering" refers to providing a pharmaceutical agent or composition to a subject.

Administered in combination: As used herein, the term "administered in combination" or "combined administration" means that two or more agents are administered to a subject at the same time or within an interval such that there may be an overlap of an effect of each agent on the patient. In certain embodiments, they are administered within about 60, 30, 15, 10, 5, or 1 minute of one another. In certain embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In certain embodiments, "animal" refers to humans at any stage of development. In certain embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In certain embodiments, animals include, but are not limited to, mammals, birds, reptiles, amphibians, fish, and worms. In certain embodiments, the animal is a transgenic animal, genetically-engineered animal, or a clone.

Antisense strand: As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

Approximately: As used herein, the term "approximately" or "about," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

Baculoviral expression vector (BEV): As used herein a BEV is a baculoviral expression vector, i.e., a polynucleotide vector of baculoviral origin. Systems using BEVs are known as baculoviral expression vector systems (BEVSs).

mBEV or modified BEV: As used herein, a modified BEV is an expression vector of baculoviral origin which has been altered from a starting BEV (whether wild type or artificial) by the addition and/or deletion and/or duplication and/or inversion of one or more: genes; gene fragments; cleavage sites; restriction sites; sequence regions; sequence(s) encoding a payload or gene of interest; or combinations of the foregoing.

Bifunctional: As used herein, the term "bifunctional" refers to any substance, molecule or moiety which is capable of or maintains at least two functions. The functions may affect the same outcome or a different outcome. The structure that produces the function may be the same or different.

BIIC: As used herein a BIIC is a baculoviral infected insect cell.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, an AAV particle of the present disclosure may be considered biologically active if even a portion of the encoded payload is biologically active or mimics an activity considered biologically relevant.

Capsid: As used herein, the term "capsid" refers to the protein shell of a virus particle.

Codon optimized: As used herein, the terms "codon optimized" or "codon optimization" refers to a modified nucleic acid sequence which encodes the same amino acid sequence as a parent/reference sequence, but which has been altered such that the codons of the modified nucleic acid sequence are optimized or improved for expression in a particular system (such as a particular species or group of species). As a non-limiting example, a nucleic acid sequence which includes an AAV capsid protein can be codon optimized for expression in insect cells or in a particular insect cell such *Spodoptera frugiperda* cells. Codon optimization can be completed using methods and databases known to those in the art.

Complementary and substantially complementary: As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present disclosure, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity. As used herein, the term "substantially complementary" means that the siRNA has a sequence (e.g., in the antisense strand) which is sufficient to bind the desired target mRNA, and to trigger the RNA silencing of the target mRNA.

Compound: Compounds of the present disclosure include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conditionally active: As used herein, the term "conditionally active" refers to a mutant or variant of a wild-type polypeptide, wherein the mutant or variant is more or less active at physiological conditions than the parent polypeptide. Further, the conditionally active polypeptide may have increased or decreased activity at aberrant conditions as compared to the parent polypeptide. A conditionally active polypeptide may be reversibly or irreversibly inactivated at normal physiological conditions or aberrant conditions.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In certain embodiments, two or more sequences are said to be "completely conserved" if they are 100% identical to one another. In certain embodiments, two or more sequences are said to be "highly conserved" if they are at least 70% identical, at least 80% identical, at least 90% identical, or at least 95% identical to one another. In certain embodiments, two or more sequences are said to be "highly conserved" if they are about 70% identical, about 80% identical, about 90% identical, about 95%, about 98%, or about 99% identical to one another. In certain embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In certain embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an polynucleotide or polypeptide or may apply to a portion, region or feature thereof.

Control Elements: As used herein, "control elements", "regulatory control elements" or "regulatory sequences" refers to promoter regions, polyadenylation signals, transcription termination sequences, upstream regulatory domains, origins of replication, internal ribosome entry sites ("IRES"), enhancers, and the like, which provide for the replication, transcription and translation of a coding sequence in a recipient cell. Not all of these control elements need always be present as long as the selected coding sequence is capable of being replicated, transcribed and/or translated in an appropriate host cell.

Controlled Release: As used herein, the term "controlled release" refers to a pharmaceutical composition or compound release profile that conforms to a particular pattern of release to effect a therapeutic outcome.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering an AAV particle, a compound, substance, entity, moiety, cargo or payload.

Delivery Agent: As used herein, "delivery agent" refers to any substance which facilitates, at least in part, the in vivo delivery of an AAV particle to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Dosing regimen: As used herein, a "dosing regimen" is a schedule of administration or physician determined regimen of treatment, prophylaxis, or palliative care.

Encapsulate: As used herein, the term "encapsulate" means to enclose, surround or encase.

Engineered: As used herein, embodiments of the present disclosure are "engineered" when they are designed to have a feature or property, whether structural or chemical, that varies from a starting point, wild type or native molecule.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least one AAV particle and a delivery agent or excipient.

Fragment: A "fragment," as used herein, refers to a portion. For example, fragments of proteins may include polypeptides obtained by digesting full-length protein isolated from cultured cells.

Functional: As used herein, a "functional" biological molecule is a biological molecule in a form in which it exhibits a property and/or activity by which it is characterized.

Gene expression: The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Homology: As used herein, the term "homology" refers to the overall relatedness between polymeric molecules, e.g. between polynucleotide molecules (e.g. DNA molecules and/or RNA molecules) and/or between polypeptide molecules. In certain embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the present disclosure, two polynucleotide sequences are considered to be homologous if the polypeptides they encode are at least about 50%, 60%, 70%, 80%, 90%, 95%, or even 99% for at least one stretch of at least about 20 amino acids. In certain embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the present disclosure, two protein sequences are considered to be homologous if the proteins are at least about 50%, 60%, 70%, 80%, or 90% identical for at least one stretch of at least about 20 amino acids.

Heterologous Region: As used herein the term "heterologous region" refers to a region which would not be considered a homologous region.

Homologous Region: As used herein the term "homologous region" refers to a region which is similar in position, structure, evolution origin, character, form or function.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer. Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Altschul, S. F. et al., J. Molec. Biol., 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In certain embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that a substance is substantially separated from the environment in which it was formed or detected. Partial separation can include, for example, a composition enriched in the substance or AAV particles of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein "linker" refers to a molecule or group of molecules which connects two molecules. A linker may be a nucleic acid sequence connecting two nucleic acid sequences encoding two different polypeptides. The linker may or may not be translated. The linker may be a cleavable linker.

MicroRNA (miRNA) binding site: As used herein, a microRNA (miRNA) binding site represents a nucleotide location or region of a nucleic acid transcript to which at least the "seed" region of a miRNA binds.

Modified: As used herein "modified" refers to a changed state or structure of a molecule of the present disclosure. Molecules may be modified in many ways including chemically, structurally, and functionally. As used herein, embodiments of the disclosure are "modified" when they have or possess a feature or property, whether structural or chemical, that varies from a starting point, wild type or native molecule.

Mutation: As used herein, the term "mutation" refers to any changing of the structure of a gene, resulting in a variant (also called "mutant") form that may be transmitted to subsequent generations. Mutations in a gene may be caused by the alternation of single base in DNA, or the deletion, insertion, or rearrangement of larger sections of genes or chromosomes.

Naturally Occurring: As used herein, "naturally occurring" or "Wild-type" means existing in nature without artificial aid, or involvement of the hand of man.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Open reading frame: As used herein, "open reading frame" or "ORF" refers to a sequence which does not contain a stop codon within the given reading frame, other than at the end of the reading frame.

Operably linked: As used herein, the phrase "operably linked" refers to a functional connection between two or more molecules, constructs, transcripts, entities, moieties or the like.

Patient: As used herein, "patient" refers to a subject who may seek or be in need of treatment, requires treatment, is receiving treatment, will receive treatment, or a subject who is under care by a trained professional for a particular disease or condition.

Payload: As used herein, "payload" or "payload region" refers to one or more polynucleotides or polynucleotide regions encoded by or within a viral genome or an expression product of such polynucleotide or polynucleotide region. e.g., a transgene, a polynucleotide encoding a polypeptide or multi-polypeptide, or a modulatory nucleic acid or regulatory nucleic acid.

Payload construct: As used herein, "payload construct" is one or more vector production construct which includes a polynucleotide region encoding or comprising a payload that is flanked on one or both sides by an inverted terminal repeat (ITR) sequence. The payload construct presents a template that is replicated in a viral production cell to produce a therapeutic viral genome within a viral particle.

Payload construct vector: As used herein, "payload construct vector" is a vector encoding or comprising a payload construct, and regulatory regions for replication and expression of the payload construct in bacterial cells.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile can be used.

Lists of suitable salts are found in *Remington's Pharmaceutical Sciences*, 17th ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the present disclosure wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" or "prevention" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified," "purification" means to make substantially pure or clear from unwanted components, material defilement, admixture or imperfection. "Purified" refers to the state of being pure. "Purification" refers to the process of making pure.

Region: As used herein, the term "region" refers to a zone or general area. In certain embodiments, when referring to a protein or protein module, a region may include a linear sequence of amino acids along the protein or protein module or may include a three-dimensional area, an epitope and/or a cluster of epitopes. In certain embodiments, regions include terminal regions. As used herein, the term "terminal region" refers to regions located at the ends or termini of a given agent. When referring to proteins, terminal regions may include N- and/or C-termini. N-termini refer to the end of a protein comprising an amino acid with a free amino group. C-termini refer to the end of a protein comprising an amino acid with a free carboxyl group. N- and/or C-terminal regions may there for include the N- and/or C-termini as well as surrounding amino acids. In certain embodiments, N- and/or C-terminal regions include from about 3 amino acid to about 30 amino acids, from about 5 amino acids to about 40 amino acids, from about 10 amino acids to about 50 amino acids, from about 20 amino acids to about 100 amino acids and/or at least 100 amino acids. In certain embodiments, N-terminal regions may include any length of amino acids that includes the N-terminus but does not include the C-terminus. In certain embodiments, C-terminal regions may include any length of amino acids, which include the C-terminus, but do not include the N-terminus.

In certain embodiments, when referring to a polynucleotide, a region may include a linear sequence of nucleic acids along the polynucleotide or may include a three-dimensional area, secondary structure, or tertiary structure. In certain embodiments, regions include terminal regions. As used herein, the term "terminal region" refers to regions located at the ends or termini of a given agent. When referring to polynucleotides, terminal regions may include 5' and 3' termini. 5' termini refer to the end of a polynucleotide comprising a nucleic acid with a free phosphate group. 3' termini refer to the end of a polynucleotide comprising a nucleic acid with a free hydroxyl group. 5' and 3' regions may there for include the 5' and 3' termini as well as surrounding nucleic acids. In certain embodiments, 5' and 3' terminal regions include from about 9 nucleic acids to about 90 nucleic acids, from about 15 nucleic acids to about 120 nucleic acids, from about 30 nucleic acids to about 150 nucleic acids, from about 60 nucleic acids to about 300 nucleic acids and/or at least 300 nucleic acids. In certain embodiments, 5' regions may include any length of nucleic acids that includes the 5' terminus but does not include the 3' terminus. In certain embodiments, 3' regions may include any length of nucleic acids, which include the 3' terminus, but does not include the 5' terminus.

RNA or RNA molecule: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

RNA interfering or RNAi: As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

ample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Self-complementary viral particle: As used herein, a "self-complementary viral particle" is a particle included of at least two components, a protein capsid and a polynucleotide sequence encoding a self-complementary genome enclosed within the capsid.

Sense Strand: As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the other siRNA strand.

Short interfering RNA or siRNA: As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. In certain embodiments, a siRNA molecule includes between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, such as 21 nucleotides (or nucleotide analogs), for example, 19, 20, 21 or 22 nucleotides. The term "long" siRNA refers to a siRNA comprising 24-60 nucleotides, such as about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event. In certain embodiments, a single unit dose is provided as a discrete dosage form (e.g., a tablet, capsule, patch, loaded syringe, vial, etc.).

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and in certain embodiments, capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In certain embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In certain embodiments, an individual who is susceptible to a disease, disorder, and/or condition will develop the disease, disorder, and/or condition. In certain embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present disclosure may be chemical or enzymatic.

Targeting: As used herein, "targeting" means the process of design and selection of nucleic acid sequence that will hybridize to a target nucleic acid and induce a desired effect.

Targeted Cells: As used herein, "targeted cells" refers to any one or more cells of interest. The cells may be found in vitro, in vivo, in situ or in the tissue or organ of an organism. The organism may be an animal, such as a mammal, a human, or a human patient.

Terminal region: As used herein, the term "terminal region" refers to a region on the 5' or 3' end of a region of linked nucleosides or amino acids (polynucleotide or polypeptide, respectively).

Terminally optimized: The term "terminally optimized" when referring to nucleic acids means the terminal regions of the nucleic acid are improved in some way, e.g., codon optimized, over the native or wild type terminal regions.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In certain embodiments, a therapeutically effective amount is provided in a single dose. In certain embodiments, a therapeutically effective amount is administered in a dosage regimen comprising a plurality of doses. Those skilled in the art will appreciate that in certain embodiments, a unit dosage form may be considered to include a therapeutically effective amount of a particular agent or entity if it includes an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24-hour period. It may be administered as a single unit dose.

Transfection: As used herein, the term "transfection" refers to methods to introduce exogenous nucleic acids into a cell. Methods of transfection include, but are not limited to, chemical methods, physical treatments and cationic lipids or mixtures.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Vector: As used herein, a "vector" is any molecule or moiety which transports, transduces or otherwise acts as a carrier of a heterologous molecule. Vectors of the present disclosure may be produced recombinantly and may be based on and/or may include adeno-associated virus (AAV) parent or reference sequence. Such parent or reference AAV sequences may serve as an original, second, third or subsequent sequence for engineering vectors. In non-limiting examples, such parent or reference AAV sequences may include any one or more of the following sequences: a polynucleotide sequence encoding a polypeptide or multi-polypeptide, which sequence may be wild-type or modified from wild-type and which sequence may encode full-length or partial sequence of a protein, protein domain, or one or more subunits of a protein; a polynucleotide comprising a modulatory or regulatory nucleic acid which sequence may be wild-type or modified from wild-type; and a transgene that may or may not be modified from wild-type sequence. These AAV sequences may serve as either the "donor" sequence of one or more codons (at the nucleic acid level) or amino acids (at the polypeptide level) or "acceptor" sequences of one or more codons (at the nucleic acid level) or amino acids (at the polypeptide level).

Viral genome: As used herein, a "viral genome" or "vector genome" refers to the nucleic acid sequence(s) encapsulated in an AAV particle.

IV. Equivalents and Scope

Those skilled in the art will recognize or be able to ascertain using no more than routine experimentation, many equivalents to the specific embodiments in accordance with the present disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the present disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the present disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the present disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the present disclosure.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

EXAMPLES

Example 1. Random Sequences with Altered G:C Content

To evaluate the effects of capsid incorporation ratios of GC content of the leader sequence of the 5' UTR, a series of 5' UTRs were designed from the parental gene leader sequences, Leader10 (AAV.rh10) and LeaderB (AAV.PRP.B). The leader sequences are given in Table 3, including the size of the sequence ahead of the ATG start codon and the G:C content of the leader sequence in percentage.

TABLE 3

| NAME | LEADER SEQUENCE (5'-3') |
|---|---|
| Leader10-8 (GC25% 99 bp-ATG) | TTAACACTTTAACCTTATAATACACATGCTGAGAATACTAATTATCGTAATGATGAT AGTATCCTATAGGAATTAATCTTATATAATGATTAGAAGCTT (SEQ ID NO: 59) |
| Leader10-10 (GC62% 24 bp-ATG) | ACACACCGGTGGAGGCACGTCCTT (SEQ ID NO: 60) |
| Leader10-16 (GC34% 99 bp-ATG) | TGAGCACGGTAACCTTATAATACACCTGCCGAGAATACTAATTATCGTAATGATGAT AGTATCCTCTCGGAAGTAATCTTATATAATGTTTAGAAGCTT (SEQ ID NO: 61) |
| Leader10-18 (GC50% 99 bp-ATG) | TGAGCACGGTGACCTTAGAATACACCTGCCGAGTAAGCTCATTGTCGTAATGATGAT AGTATCCTCTCGGCATCAGTCTAGCCTGAGGCTTAGCCGCTT (SEQ ID NO: 62) |
| Leader10-20 (GC58% 99 bp-ATG) | TGAGCACGGTGACCTTAGAAGGCACCTGCCGAGTAGGCTCATTGTCGTCCTGATGAT AGTAGCCTCTCGGCATGAGTCTCGCCTGCTGCGGAGCCGCTT (SEQ ID NO: 63) |

TABLE 3-continued

| NAME | LEADER SEQUENCE (5'-3') |
|---|---|
| Leader10-2 (AcNPV-CTG) | Sequence of Leader10 parental serotype having CTG start codon and baculovirus AcNPV |
| Leader10-12 (L21-CTG) | Sequence of Leader10 parental serotype having leader sequence and CTG start codon |
| Leader10-6 (ACNPV-CTG-no optimization) | Sequence of Leader10 parental serotype having CTG start codon and baculovirus AcNPV. Sequence not codon optimized |
| Leader10-22 (AAV2LS-wk3-ATG) | Sequence of Leader10 parental serotype having the AAV2 leader sequence and Kozak sequence ATG-wk3 and ATG start codon. |
| LeaderB-2 (AAV2LS, codon optimized, CTG, no ACG for VP2 | Sequence of LeaderB parental serotype having the AAV2 leader sequence, CTG start codon and no ACG start codon for VP2. Sequence is codon optimized. |

Figure 3:
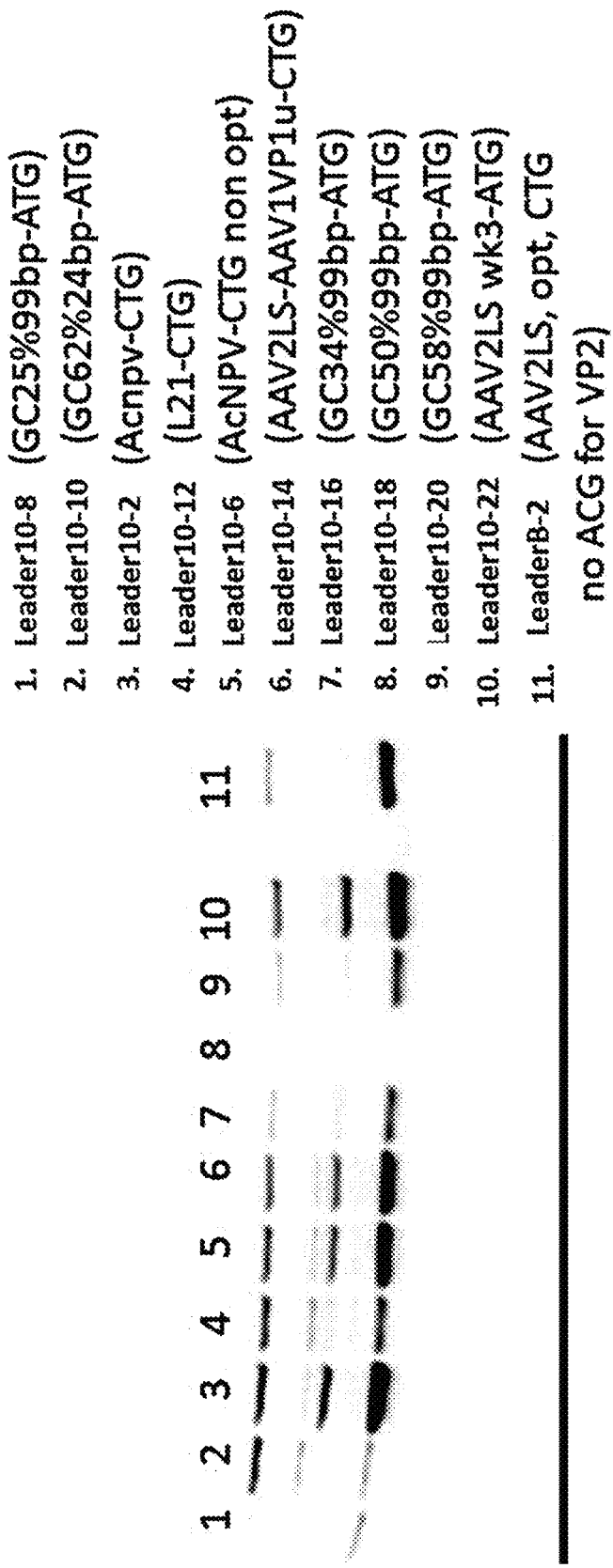
FIG. 3 is a Western blot analysis showing VP1, VP2 and VP3 expression corresponding with GC content in certain engineered UTRs of the present disclosure.

Each of the random leader sequences were inserted in the 5' UTR of the Leader10 capsid gene ahead of the ATG start codon of VP11 to form the constructs in Table 2. Western blot analysis was used to determine VP1, VP2 and VP3 expression. Results are shown in FIG. 3.

For Leader10-8 (GC25%99 bp-ATG), all capsid proteins were reduced. For Leader10-10 (GC62%24 bp-ATG), the expression of VP1 was too strong relative to VP3. For Leader10-16 (GC34%99 bp-ATG), all capsid proteins were decreased but maintained a ratio close to 1:1:10 (VP1:VP2:VP3). For Leader10-18 (GC50%99 bp-ATG), no results were obtained. For Leader10-20 (GC58%99 bp-ATG), the overall yield was decreased and the levels were altered such that VP2<VP1<<VP3.

Folding studies of the random leader sequences (SEQ ID No: 59-63) using mFold software revealed the formation of a hairpin structure upstream (i.e., 5') of the VP1 ATG start codon.

Example 2. Alteration of the Kozak Sequence

To explore the affect of the Kozak sequence strength on the capsid protein expression ratio, various Kozak sequences were engineered into the 5' UTR of VP1 in two different AAV serotypes.

Figure 4:
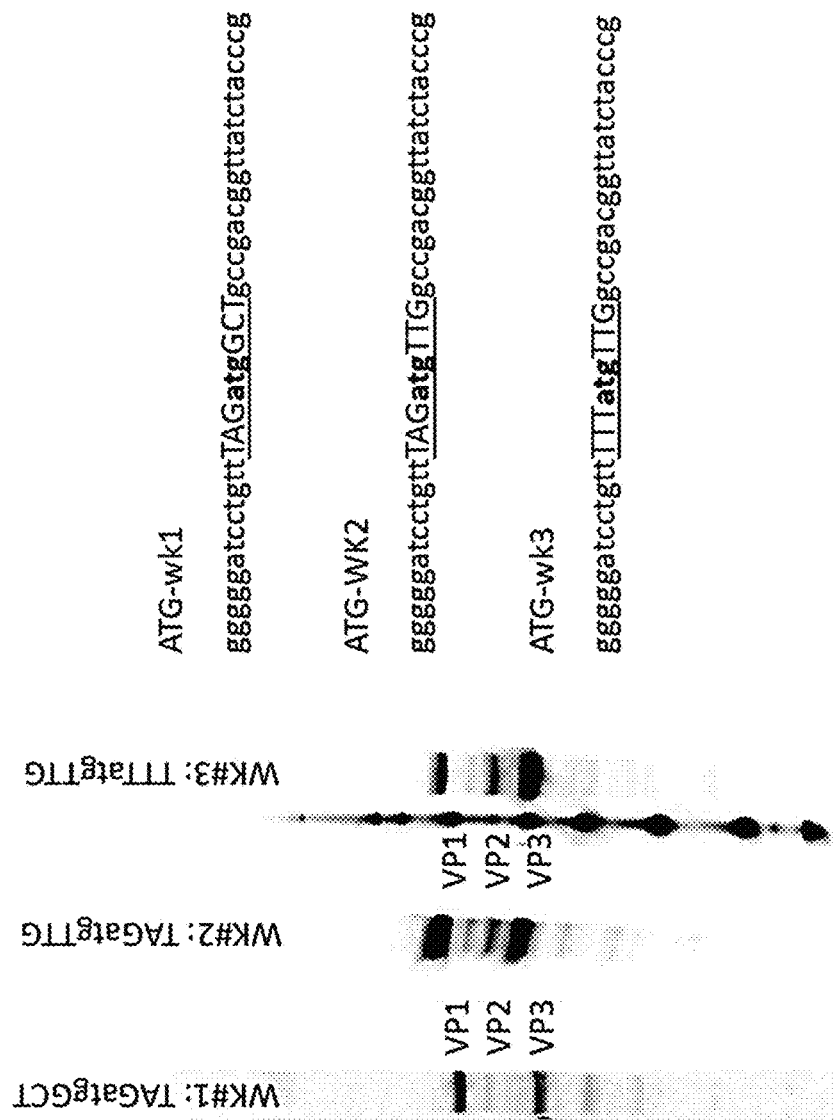
FIG. 4 is a Western blot analysis showing VP1, VP2 and VP3 expression corresponding with Weak Kozak sequences in certain engineered UTRs of the present disclosure. Weak Kozak sequences are underlined and ATG start codon is in bold.

Three sequences were designed for the parental serotype, AAV2. These were "ATG-wk1" (gggggatcctgttTA-GatgGCTgccgacggttatctacccg; SEQ ID NO: 64); "ATG-wk2" (gggggatectgttTAGatgTTGgccgacggttatctacccg; SEQ ID NO: 65) and "ATG-wk3" (gggggatcctgttTT-TatgTTGgccgacggttatctacccg; SEQ ID NO: 66). The start codons are identified in bold. The expressions of the capsid proteins were determined by Western blot, with results shown in FIG. 4.

ATG-wk1 showed low expression of all capsid proteins, with minimal VP2 expression and an unfavorable VP1:VP3 ratio of about 1:1. ATG-wk2 showed strong over-expression of VP1, resulting in unfavorable VP1:VP3 ratios above 1:1. ATG-wk3 showed the best expression results, with VP1: VP2:VP3 closest to 1:1:10.

Figure 5:
FIG. 5 is a Western blot analysis showing VP1, VP2 and VP3 expression corresponding with certain engineered UTRs of the present disclosure.

The construct "Leader10-16 (AAV2WK3-ATG)" was then designed from ATG-wk3 using Leader10 (AAV.rh10), having a sequence ACTCGACGAAGACTTGAT-CACCCGGGGGATCCTGTTTTTatgTTG (SEQ ID NO: 67; AAV2 leader sequence, ATG start codon in bold, Kozak sequence is underlined). The Western blot for the construct is shown in FIG. 5. The figure shows both the full and empty capsids.

Example 3. Investigations of Hairpin (HP) Structure. Length and Arrangement

Design characteristics which could lead to the ability to regulate capsid protein expression, ratios and levels were evaluated, including the presence of mismatches, the size of the hairpin loop, the nature of the flanking sequences and the arrangement of certain features relative to the start codon. The study involved the introduction of a hairpin into the 5' UTR of a capsid gene, engineering the 5' UTR size, alteration (e.g., weakening) the strength of the Kozak sequence, and de-optimization of the VP1 unique region.

Figure 6A:
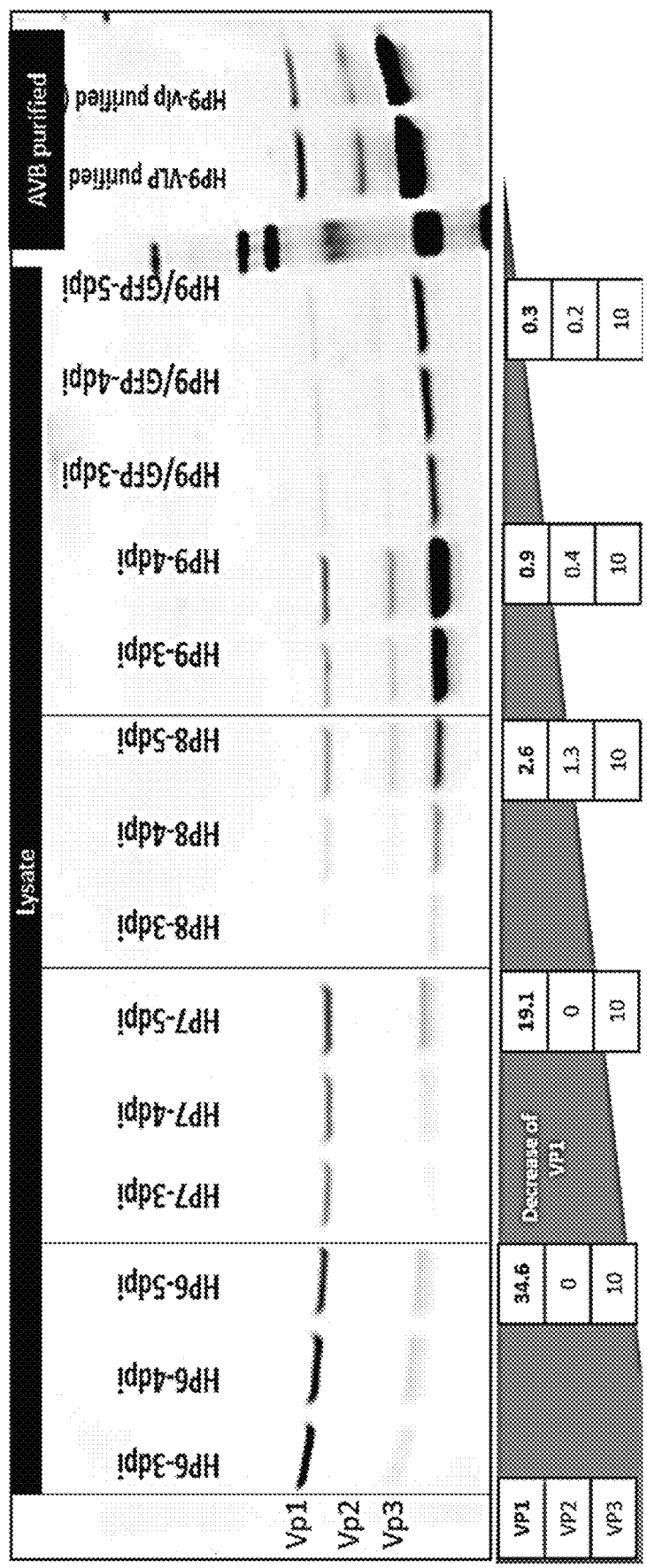
FIG. 6A is a Western blot analysis showing VP1, VP2 and VP3 expression corresponding with HP (hairpin) 6, 7, 8, and 9 at 3, 4, and 5 days post infection.
Figure 6B:
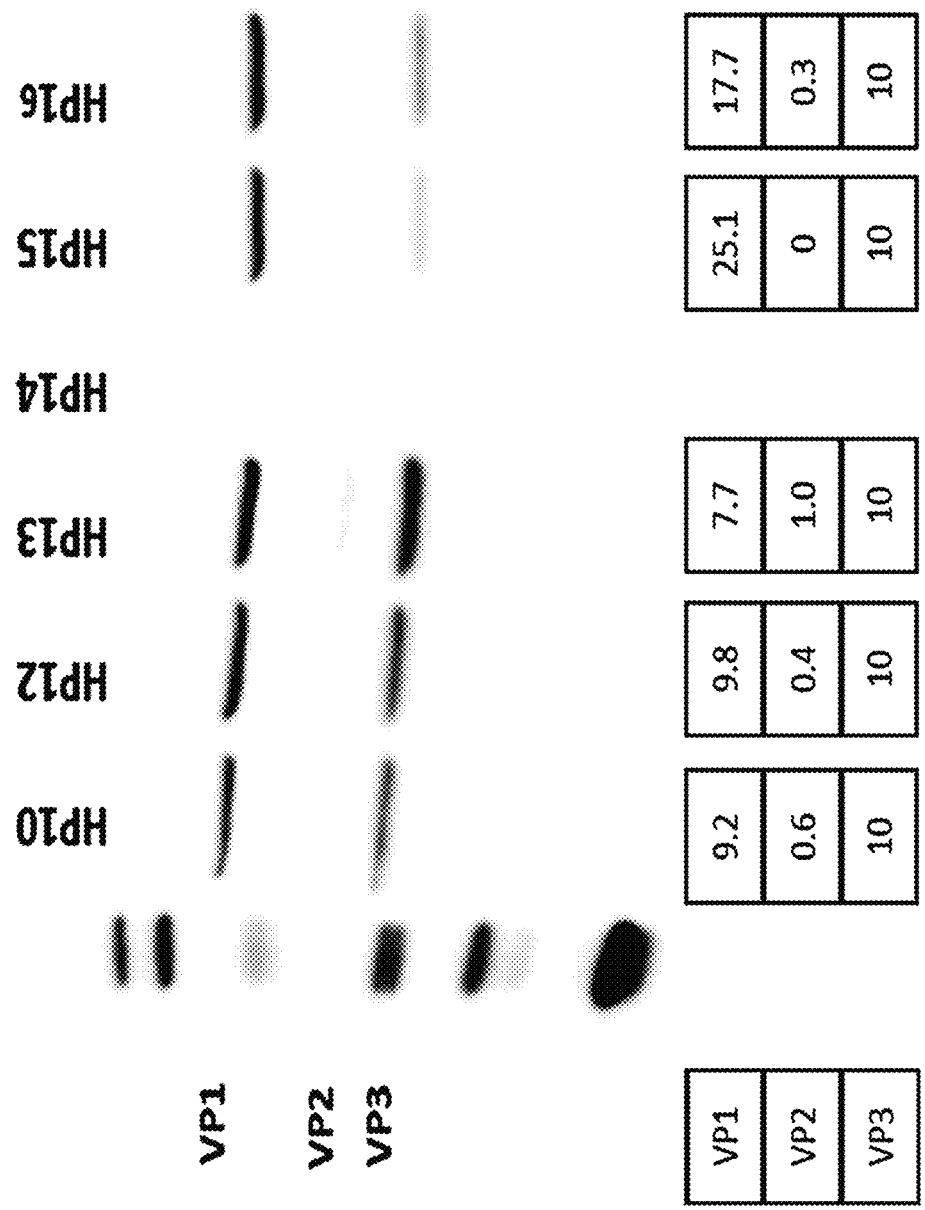
FIG. 6B is a Western blot analysis showing VP1, VP2 and VP3 expression corresponding with HP (hairpin) 10, 12, 13, 14, 15, and 16.
Figure 7A:
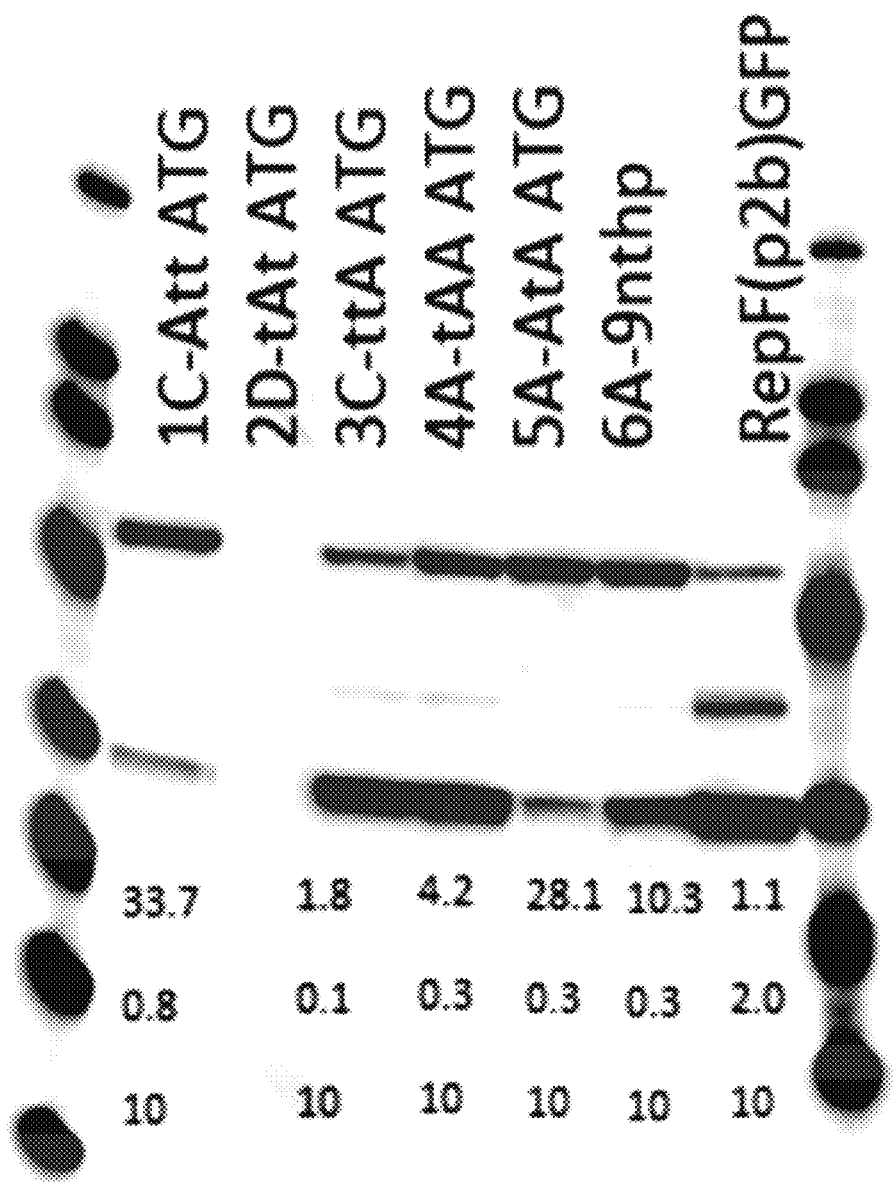
FIG. 7A is a Western blot analysis showing VP1, VP2 and VP3 expression corresponding with various Kozak sequences in certain engineered UTRs of the present disclosure.
Figure 7B:
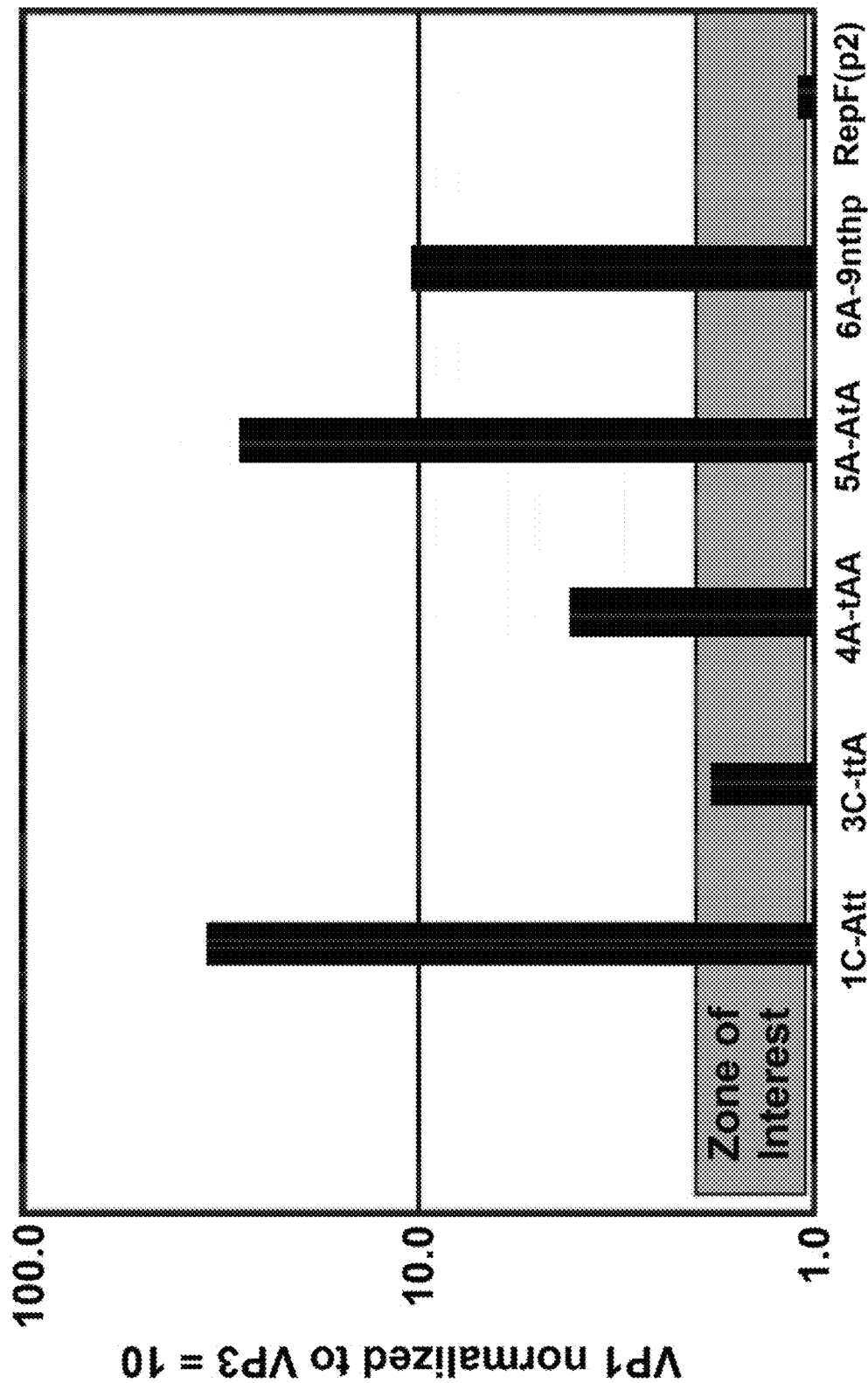
FIG. 7B is a histogram of the Western blot analysis shown in FIG. 7A.
Figure 8A:
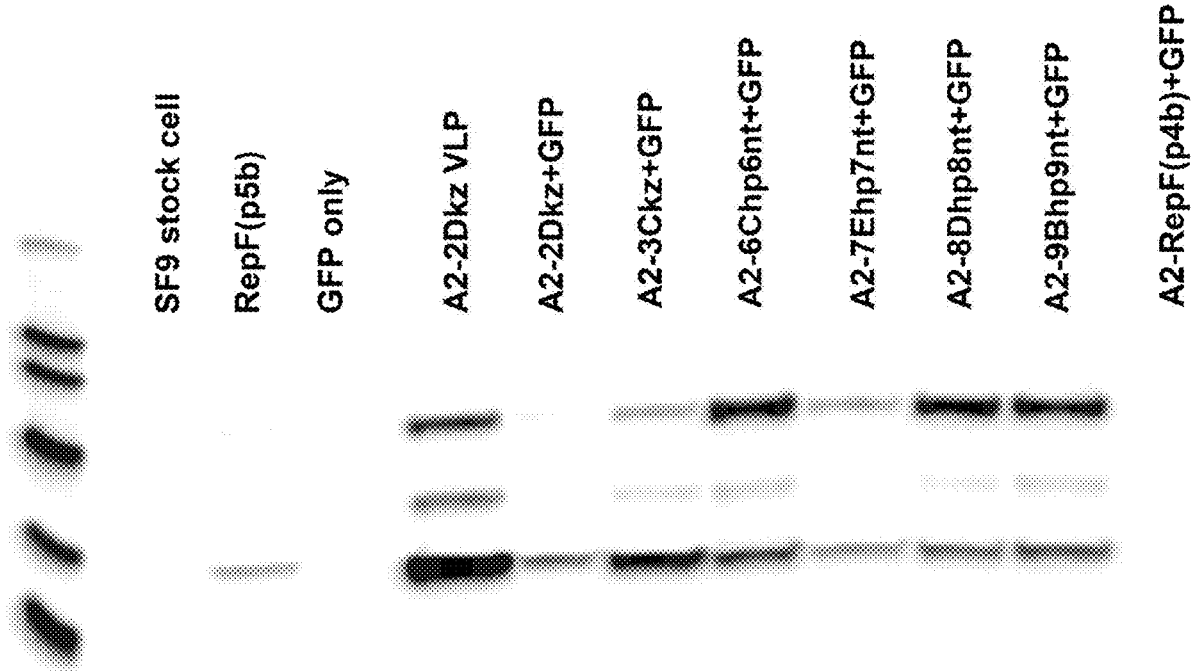
FIG. 8A is a Western blot analysis showing VP1, VP2 and VP3 expression corresponding with various Kozak sequences in certain engineered UTRs of the present disclosure.
Figure 8B:
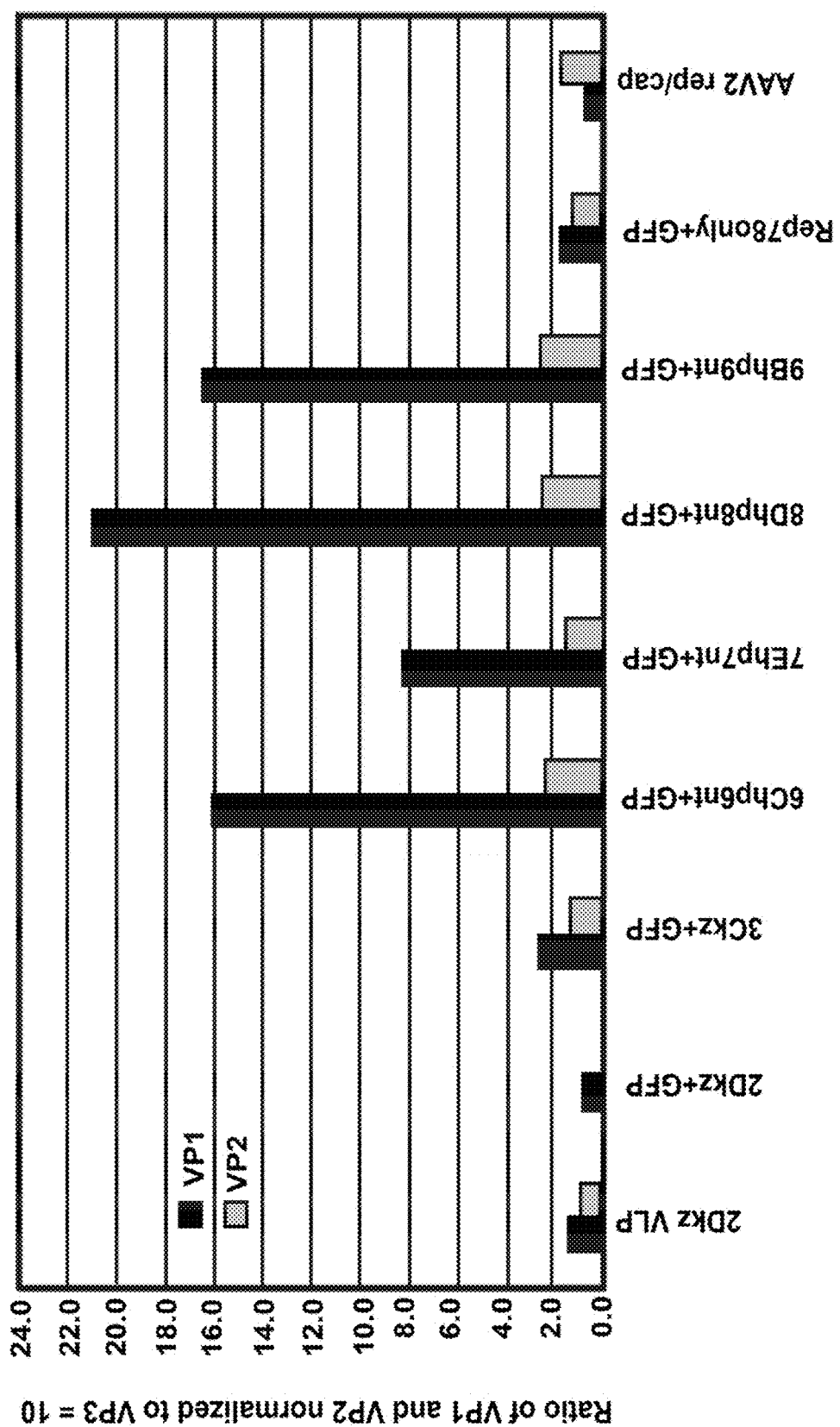
FIG. 8B is a histogram of the Western blot analysis shown in FIG. 8A.
Figure 8C:
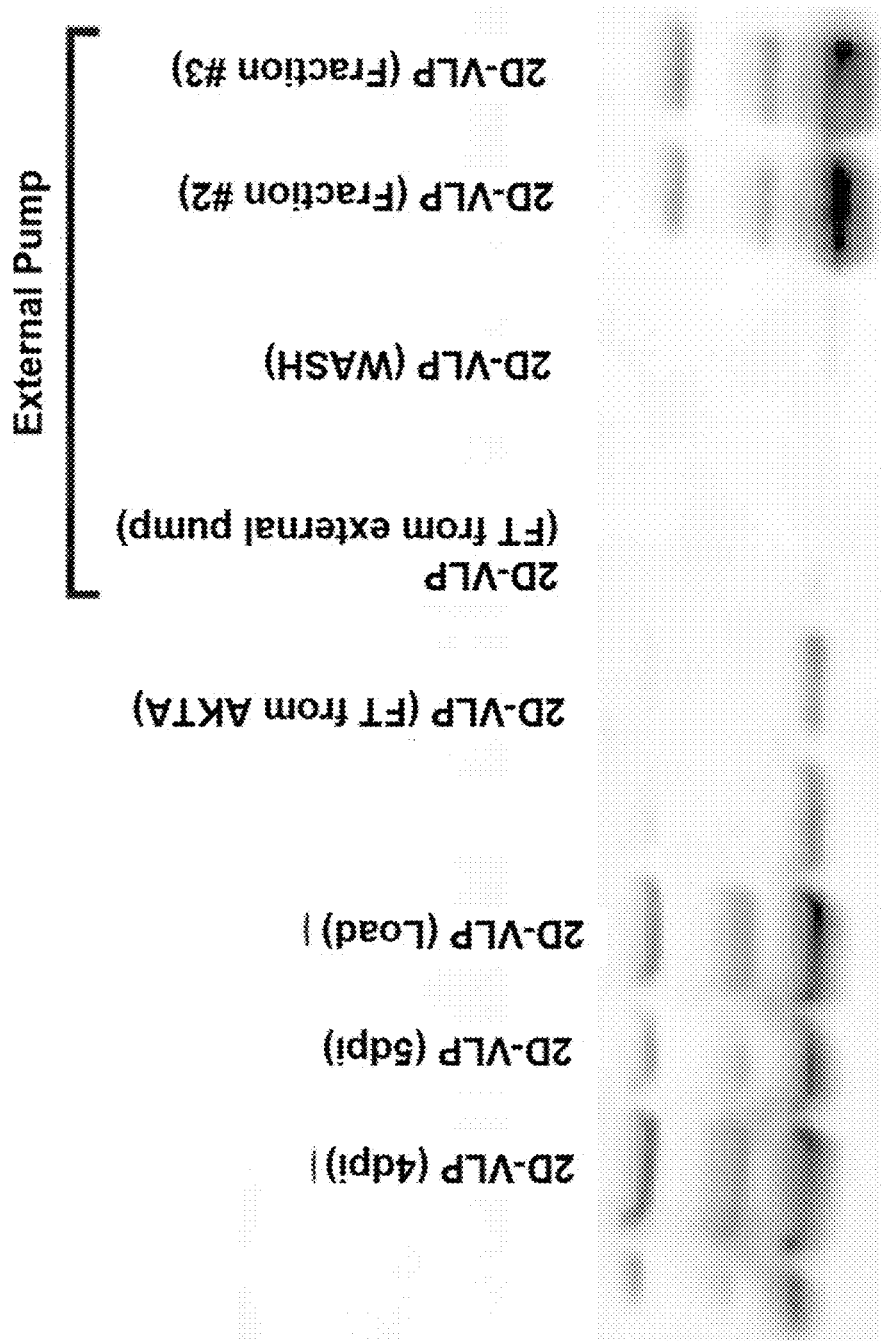
FIG. 8C shows the expression levels and production of VP1, VP2 and VP3 for HP9-2D.

The constructs designed and tested are given in Table 1. These constructs were based on the parental AAV2 serotype. The ratio of VP1:VP2:VP3 expression was determined, with results shown in FIG. 6A and FIG. 6B. FIG. 6A shows the expression levels of VP1, VP2 and VP3 for HP (hairpin) 6, 7, 8, and 9 at 3, 4, and 5 days post infection. FIG. 6B shows the expression levels of VP1, VP2 and VP3 for HP (hairpin) 10, 12, 13, 14, 15, and 16.

HP6 provided a VP1:VP3 ratio after 5 days of about 3.5:1, with no VP2. HP7 provided a VP1:VP3 ratio after 5 days of about 2:1, with no VP2. HP8 provided a VP1:VP2:VP3 ratio after 5 days of about 2.6:1.3:10. HP9 provided favorable results with a VP1:VP2:VP3 ratio after 4 days of about 1:0.5:10.

HP10 provided VP1:VP2:VP3 ratio of about 9.2:0.6:10. HP12 provided VP1:VP2:VP3 ratio of about 9.8:0.4:10. HP13 provided VP1:VP2:VP3 ratio of about 7.7:1:10. HP14 showed no expression. HP15 provided VP1:VP3 ratio of about 2.5:1, with no VP2. HP16 provided VP1:VP2:VP3 ratio of about 17.7:0.3:10.

Example 4. Alternative Kozak Sequences

Studies involving the use of alternative Kozak sequences in 5' UTR hairpins were performed to determine corresponding VP1, VP2 and VP3 ratios.

Hairpin 9 from Table 1 was selected using an AAV2 parent serotype. The Kozak sequences tested are given in Table 4, as well as corresponding VP1:VP2:VP3 ratios.

TABLE 4

| Name | Concentration ng/ul | Kozak Sequence | VP1:VP2:VP3 ratio |
|---|---|---|---|
| Original: HP#9 | | TTT ATG GCT | |
| 1C-Att | 92 | ATT ATG GCT | 33.7/0.8/10 |
| 2D-tAt | 30 | TAT ATG GCT | No Results |
| 3C-ttA | 25 | TTA ATG GCT | 1.8/0.1/10 |
| 4A-tAA | 60 | TAA ATG GCT | 4.2/0.3/10 |
| 5A-AtA | 81 | ATA ATG GCT | 28.1/0.3/10 |

FIGS. 7A, 7B, 8A, 8B and 8C illustrate the VP protein expression levels for the different engineered polynucleotides of Table 4. These data show that AAV2HP9-3C demonstrates a favorable expression level VP1 relative to VP3, and that AAV2HP9-2D demonstrated a favorable VP1:VP2:VP3 expression level.

We claim:

1. An expression control sequence comprising a start codon and an engineered 5' UTR polynucleotide, wherein the engineered 5' UTR polynucleotide encodes a hairpin structure which comprises, from 5' to 3':
   (i) a 5' flanking region which is 4-30 nucleotides in length, and
   (ii) a stem-loop structure comprising a stem region which is 4-30 nucleotides in length, and a loop region which is 3' of the stem region and which is 4-15 nucleotides in length, wherein the loop region of the stem-loop structure is encoded by a nucleotide sequence selected from tttatggct and atctaa, or a nucleotide sequence which is at least 60% identical to a nucleotide sequence selected from tttatggct and atctaa.

2. The expression control sequence of claim 1, wherein the start codon is ATG or ACG.

3. The expression control sequence of claim 2, wherein the expression control sequence comprises a Kozak sequence or modified Kozak sequence, and wherein the Kozak sequence or modified Kozak sequence comprises the start codon.

4. The expression control sequence of claim 1, wherein the 5' flanking region is encoded by a nucleotide sequence selected from atacgact, atac, and SEQ ID NOs: 17-20, or a nucleotide sequence which is at least 60% identical to a nucleotide sequence selected from atacgact, atac, and SEQ ID NOs: 17-20.

5. The expression control sequence of claim 1, wherein the stem region of the stem-loop structure is encoded by a nucleotide sequence selected from cggc, ctgcc and SEQ ID NOs: 21-31, or a nucleotide sequence which is at least 60% identical to a nucleotide sequence selected from cggc, ctgcc and SEQ ID NOs: 21-31.

6. The expression control sequence of claim 1, wherein the stem-loop structure comprises a stem-complement region which is 3' of the stem region and which is 4-20 nucleotides in length.

7. The expression control sequence of claim 6, wherein the stem-complement region of the stem-loop structure is encoded by a nucleotide sequence selected from ggcag, SEQ ID NO: 32, and SEQ ID NO: 33, or a nucleotide sequence which is at least 60% identical to a nucleotide sequence selected from ggcag, SEQ ID NO: 32, and SEQ ID NO: 33.

8. The expression control sequence of claim 6, wherein the nucleotide sequence encoding the stem-complement region is 100% complementary to the nucleotide sequence encoding the stem region, or wherein the nucleotide sequence encoding the stem-complement region and the nucleotide sequence encoding the stem region are complementary and include only one mismatch, only two mismatches, only three mismatches, only four mismatches or only five mismatches.

9. The expression control sequence of claim 6, wherein the distance between the 3' end of the loop region and the start codon is from 1-10 nucleotides, and/or the distance between the 3' end of the stem-complement region and the start codon is from 1-30 nucleotides.

10. The expression control sequence of claim 1, wherein the hairpin structure comprises a 3' flanking region which is 3' of the stem-loop structure and is 4-30 nucleotides in length.

11. The expression control sequence of claim 1, wherein the hairpin structure comprises the start codon, and wherein the start codon is within (a) the loop region of the stem-loop structure, (b) the stem-complement region of the stem-loop structure, or (c) the 3' flanking region of the hairpin structure.

12. The expression control sequence of claim 1, wherein the expression control sequence comprises a promoter.

13. The expression control sequence of claim 12, wherein the promoter is a p10 promoter or a polH promoter.

14. A viral expression construct comprising a protein-coding nucleotide sequence and the expression control sequence of claim 1, wherein the expression control sequence is operably linked to the protein-coding nucleotide sequence.

15. The viral expression construct of claim 14, wherein the protein-coding nucleotide sequence encodes a structural AAV capsid protein selected from VP1, VP2, VP3, or a combination thereof, and/or a non-structural AAV replication protein selected from Rep78, Rep52, or a combination thereof.

16. A method of producing proteins encoded by a protein-coding nucleotide sequence, the method comprising:
   (i) introducing the viral expression construct of claim 14 into a viral production cell, and
   (ii) placing the viral production cell under conditions in which the cellular machinery of the viral production cell expresses the proteins encoded by the protein-coding nucleotide sequence in the viral expression construct.

17. An expression control sequence comprising a start codon and an engineered 5' UTR polynucleotide, wherein the engineered 5' UTR polynucleotide encodes a hairpin structure which comprises, from 5' to 3':
   (i) a 5' flanking region which is 4-30 nucleotides in length,
   (ii) a stem-loop structure comprising a stem region which is 4-30 nucleotides in length, and a loop region which is 3' of the stem region and which is 4-15 nucleotides in length, and
   (iii) a 3' flanking region which is 3' of the stem-loop structure and is 4-30 nucleotides in length, wherein the 3' flanking region is encoded by a nucleotide sequence selected from tttatggct, attatggct, tatatggct, ttaatggct, taaatggct, ataatggct, and SEQ ID NO: 34-35, or a nucleotide sequence which is at least 60% identical to a nucleotide sequence selected from tttatggct, attatggct, tatatggct, ttaatggct, taaatggct, ataatggct, and SEQ ID NOs: 34-35.

18. A viral expression construct comprising a protein-coding nucleotide sequence and the expression control sequence of claim 17, wherein the expression control sequence is operably linked to the protein-coding nucleotide sequence.

19. An expression control sequence comprising a start codon and an engineered 5' UTR polynucleotide, wherein the engineered 5' UTR polynucleotide encodes a hairpin structure which comprises, from 5' to 3':
   (i) a 5' flanking region which is 4-30 nucleotides in length,
   (ii) a stem-loop structure comprising a stem region which is 4-30 nucleotides in length, and a loop region which is 3' of the stem region and which is 4-15 nucleotides in length, wherein the hairpin structure is encoded by a nucleotide sequence selected from SEQ ID NO: 1-16.

20. A viral expression construct comprising a protein-coding nucleotide sequence and the expression control sequence of claim 19, wherein the expression control sequence is operably linked to the protein-coding nucleotide sequence.

* * * * *